US012205688B2

(12) United States Patent
Sanchez, Jr. et al.

(10) Patent No.: US 12,205,688 B2
(45) Date of Patent: Jan. 21, 2025

(54) MEDICAL RECORD DIGEST

(71) Applicant: ZOLL Medical Corporation, Chelmsford, MA (US)

(72) Inventors: Mario Sanchez, Jr., Longmont, CO (US); Gary A. Freeman, Waltham, MA (US); Peter G. Goutmann, Gibsonia, PA (US); Gregory G. Howard, Pittsburgh, PA (US); Robert W. Krier, Boulder, CO (US); Gregory D. Mears, Carolina Beach, NC (US); Frederick W. Forester, Encinitas, CA (US); Kevin M. Zahora, Liberty Township, OH (US)

(73) Assignee: ZOLL Medical Corporation, Chelmsford, MA (US)

( * ) Notice: Subject to any disclaimer, the term of this patent is extended or adjusted under 35 U.S.C. 154(b) by 210 days.

(21) Appl. No.: 17/703,838

(22) Filed: Mar. 24, 2022

(65) Prior Publication Data

US 2022/0310219 A1 Sep. 29, 2022

Related U.S. Application Data

(60) Provisional application No. 63/165,350, filed on Mar. 24, 2021.

(51) Int. Cl.
*G06Q 20/00* (2012.01)
*G06F 16/93* (2019.01)
*G16H 10/60* (2018.01)

(52) U.S. Cl.
CPC ............. *G16H 10/60* (2018.01); *G06F 16/93* (2019.01)

(58) Field of Classification Search
CPC ................................ G16H 10/60; G06F 16/93
(Continued)

(56) References Cited

U.S. PATENT DOCUMENTS 6,747,561 B1 6/2004 Reeves
8,169,315 B2 5/2012 Smith
(Continued)

FOREIGN PATENT DOCUMENTS

JP 2002-032475 A 1/2002
JP 4393112 B2 1/2010
(Continued)

OTHER PUBLICATIONS

Wikipedia. "Health Level 7". Retrieved from the Wayback Machine as of Nov. 13, 2008. Accessed Dec. 9, 2019. (Year: 2008).
(Continued)

*Primary Examiner* — Dante Ravetti
(74) *Attorney, Agent, or Firm* — Finch & Maloney PLLC

(57) ABSTRACT

An EMS medical record acquisition system is provided. The system is configured to provide medical record information to an EMS rescuer in a mobile EMS environment. The system includes a user device, a patient identification data source, and a medical record digest system. The digest system is coupled to the user device and to the patient identification source. The digest system receives identification data from the patient identification source, queries a medical record repository using the identification data, receives a medical record for the patient from the medical record repository, generates a reference code based on the identification data, stores the medical record with the reference code, transmits the reference code to the user device, receives a query including the reference code from the user device, generates a digest at least a portion of the medical record, and provides the digest to the user device.

26 Claims, 23 Drawing Sheets

(58) Field of Classification Search
USPC .............. 705/16, 21, 59; 380/44, 262, 278
See application file for complete search history.

(56) References Cited

U.S. PATENT DOCUMENTS

| | | | |
|---|---|---|---|
| 8,554,170 | B2 | 10/2013 | Franz |
| 8,712,793 | B2 | 4/2014 | Jones et al. |
| 9,729,480 | B2 | 8/2017 | Bell |
| 10,574,606 | B2 | 2/2020 | Bell |
| 2003/0052788 | A1 | 3/2003 | Kwong-Tai Chung |
| 2003/0105649 | A1 | 6/2003 | Sheiner et al. |
| 2003/0195567 | A1 | 10/2003 | Jayne et al. |
| 2006/0229909 | A1* | 10/2006 | Kaila ............... G16H 10/60 705/2 |
| 2007/0083392 | A1 | 4/2007 | Zaleski |
| 2008/0133572 | A1 | 6/2008 | Verhey-Henke et al. |
| 2009/0037225 | A1 | 2/2009 | Burchianti, II et al. |
| 2010/0227585 | A1 | 9/2010 | Carroll et al. |
| 2011/0119088 | A1 | 5/2011 | Gunn |
| 2011/0295078 | A1 | 12/2011 | Reid et al. |
| 2012/0158074 | A1 | 6/2012 | Hall |
| 2012/0191476 | A1 | 7/2012 | Reid et al. |
| 2013/0096649 | A1 | 4/2013 | Martin et al. |
| 2013/0275151 | A1 | 10/2013 | Moore et al. |
| 2014/0019159 | A1 | 1/2014 | Singh et al. |
| 2014/0046940 | A1 | 2/2014 | Thomson et al. |
| 2014/0249854 | A1 | 9/2014 | Moore et al. |
| 2014/0337047 | A1 | 11/2014 | Mears et al. |
| 2014/0365241 | A1 | 12/2014 | Dillie |
| 2015/0120794 | A1 | 4/2015 | Phelan et al. |
| 2015/0127379 | A1 | 5/2015 | Sorenson |
| 2015/0242574 | A1 | 8/2015 | Antony |
| 2016/0070864 | A1 | 3/2016 | Dotan et al. |
| 2016/0162643 | A1 | 6/2016 | Newbold et al. |
| 2016/0180044 | A1 | 6/2016 | Delisle et al. |
| 2017/0296107 | A1 | 10/2017 | Reid |
| 2019/0214115 | A1 | 7/2019 | Bell |

FOREIGN PATENT DOCUMENTS

| | | |
|---|---|---|
| WO | 2014/144846 A1 | 9/2014 |
| WO | 2015/066650 A1 | 5/2015 |

OTHER PUBLICATIONS

ZOLL Data Systems, "RescueNet ePCR 5.4.3 Defect Release Notes," Jan. 26, 2014, 1 page.
ZOLL Data Systems, "RescueNet Dispatch—Billing 4.6 Services Install Guide," Oct. 23, 2015, 34 pages.
ZOLL Data Systems, RescueNet Dispatch—Billing Administration Guide, Release 4.6.1, Oct. 22, 2015, 740 pages.
ZOLL Data Systems, RescueNet Eligibility Services Installation Guide, Software Release 4.6, 2015, 7 pages.
ZOLL Data Systems, "RescueNet ePCR 5.4.3 Feature Release Notes," Jan. 26, 2014, 1 page.
ZOLL Data Systems, RescueNet TabletPCR and WebPCR User Guide, Software Version 5.4.3, 2015, 205 pages.
ZOLL Data Systems, RescueNet Billing User's Guide, Softwarex Version 4.5, 2015, 450 pages.
ZOLL Data Systems, RescueNet Billing—Dispatch Release Notes, Software Version 4.6.1, Dec. 8, 2015, 5 pages.
ZOLL Data Systems, "RescueNet ePCR Suite Administrator Guide," Software Version 5.4.3, 2015, 389 pages.
ZOLL Data Systems, "RescueNet Dispatch—Billing Upgrade for Administrators," Oct. 21, 2015, 16 pages.
Remoteoperations, SecureFlow Pro HL7 Specification ADS, MDM and ACK Message Types, Document Version 1.2, updated Nov. 3, 2005 (21 pages).
Smiley et al, "Implementation of EMS Access to Patient History" https://www.jems.com/operations/orange-county-calif-begins-field-implementation-of-ems-access-to-patient-history-via-hie/ May 1, 2017 (9 pages).
Kno2, ImageTrend Enable Broad-based Interoperability for EMS, Oct. 16, 2019 (7 pages).
www.imagetrend.com, Website know to of been captured as early as Jul. 25, 2002 (3 pages).
www.imagetrend.com/ems/, Website know to of been captured as early as Nov. 19, 2002 (33 pages).
ZOLL Data Systems, EMS and Hospital Partners: Transform the Way You Collaborate with ZOLL Care Exchange, Copyright 2021 (8 pages).

* cited by examiner

| Patient Details | | | GP Details | | | | |
|---|---|---|---|---|---|---|---|
| Gender | Female | | Name | Seth Jones | | | |
| DOB | 1/1/1970 | | Phone | 555-908-5309 | | | |
| Next of Kin | Ralph Smith | | Address | Frozen Lake, Florida, 89392 | | | |
| Phone | 555-434-1212 | | Other providers | | | | |
| Address | Zion Forest | | Name | Dorcus Hatfield | | | |
| | Anywhere, USA 41175 | | Specialty | Cardiology | | | |
| Alerts | | | Next Encounter | | | | |
| Allergies | Sulfa Drugs | | Medications | | | | |
| Stress Test Due | | | Glyburide 5mg | daily | | | |
| Diagnosis | State | Status | Encounter History | | | | |
| Diabetes | | 1-Aug-07 Ongoing | Date | Facility | Specialty | Clinical | Reason |
| Hypertension | | 1-Aug-09 Ongoing | 1-Aug-09 | GP | | Jones, S. | Headaches |
| | | | 1-Aug-07 | GP | | Jones, S. | Tired |
| | | | 5-Apr-06 | GP | | Jones, S. | Physical |
| | | | 5-Apr-05 | GP | | Jones, S. | Physical |
| | | | Immunizations | | | Diabetic Indices | |
| | | | Type | Most Recent | Number Received | Index | Value | Date | Type |
| | | | Influenza | 1-Aug-10 | 4 | LDL | 2.41 | 1-Aug-10 | |

MEDICAL RECORD DIGEST

CROSS-REFERENCE TO RELATED APPLICATIONS

This application claims the benefit under 35 U.S.C. § 119(e) of U.S. Provisional Patent Application 63/165,350, titled "MEDICAL RECORD DIGEST", filed 24 Mar. 2021. The entire disclosure of this related application is hereby incorporated herein by reference in its entirety.

BACKGROUND

The present disclosure is directed to systems and methods for provision of patient data to emergency medical care providers.

Emergency medical care organizations may utilize a wide array of information systems to support their operations. Such information systems may include computer-aided dispatch (CAD) systems, electronic patient charting systems, electronic health record (EHR) systems, medical billing systems, and health information exchange (HIE) systems, to name a few. CAD systems enable communication of emergency incident information to emergency medical services (EMS) agencies and centralized dispatch of, and communication with, field vehicles and personnel to service incidents. The functionality implemented within CAD systems may include authentication of dispatchers and field personnel to the system, creation of call records, assignment of calls to field personnel by dispatchers, and closure and storage of call records.

Electronic patient charting systems enable medical and/or emergency care providers to document patient encounters in the field. For example, an EMS crew may document a patient encounter via an electronic patient care record (ePCR). The functionality implemented within patient charting systems includes creation of ePCRs for patient encounters and closure and storage of ePCRs. The ePCRs may include data collected and entered by a care provider via a computer implemented user interface provided at an endpoint device. The patient data included in ePCRs may include patient identification, demographic, clinical impression information, and the like.

EHR systems and databases enable medical care providers to access a patient's medical history and document patient encounters within a hospital, a hospital system, or other healthcare facility. The functionality implemented within EHR systems includes authentication of medical providers to the system, creation of EHRs for patient treatment episodes, and closure and storage of EHRs. EHRs can include a variety of patient data, such as immunization status, demographics, medications and allergies, laboratory test results, patient physiological data, patient diagnosis, and the like. EHR systems and databases are used by many hospitals and other organizations to access and maintain a patient's medical history, which can assist care providers in accurately diagnosing and treating the patient.

Medical billing systems help medical organizations to bill for services rendered to patients. The functionality implemented within medical billings systems includes generation of claim records, submission of claim records to payers, tracking of and following up on processing of claims by payers, and claim record closure and storage. The claim records can include patient information such as patient, service, and payer identifiers, dates of service, billing codes, and the like. Medical billing systems increase the efficiency of a medical organization's collection processes.

HIE systems enable the exchange of patient data across organizational boundaries. HIEs are implemented using centralized, decentralized, and hybrid (partially centralized and partially decentralized) models. The patient data available through and exchanged via HIEs includes ePCRs, EHRs, and the like. HIE systems enable care providers to access an increasingly complete medical record for each patient.

SUMMARY

In one example, an emergency medical services (EMS) medical record acquisition system is provided. The system is configured to provide medical record information to an EMS rescuer in a mobile EMS environment. The system includes a user interface device associated with the mobile EMS environment and configured to provide a user interface; one or more patient identification data sources; an incident data exchange system configured to communicatively couple to the one or more patient identification data sources, an incident data exchange system, and a medical record digest system. The incident data exchange system includes exchange system memory, and one or more processors coupled to the exchange system memory. The one or more processors are configured to receive patient identification data from the one or more patient identification data sources for an EMS call for a patient, query at least one medical record repository using the patient identification data, receive a medical record for the patient from the at least one medical record repository, generate a patient reference code based on at least a portion of the patient identification data, store the medical record with the patient reference code in the exchange system memory, and transmit the medical record and the patient reference code to the medical record digest system. The medical record digest system is configured to communicatively couple to the user interface device and the incident data exchange system. The medical record digest system includes a digest system memory, and at least one processor coupled to the digest system memory. The at least one processor is configured to receive the medical record and the patient reference code from the incident data exchange system, store the medical record with the patient reference code in the digest system memory, transmit the patient reference code to the user interface device, receive a medical data query including the patient reference code from the user interface device, generate a medical record digest in response to the medical data query, the medical record digest including at least a portion of the medical record, and provide the medical record digest to the user interface.

Some examples of the system can include one or more of the following features. In the system, the one or more patient identification sources can include one or more of a computer-aided dispatch system or a patient charting system. The exchange system memory can include a predetermined patient identification criterion; and the one or more processors can be configured to determine whether the patient identification data from the one or more patient identification data sources satisfies the predetermined patient identification criterion. The predetermined patient identification criterion can include a list of identification data items necessary to include in the query to distinguish between multiple patients represented in the at least one medical record repository. The list of identification data items can include patient demographic data. The patient demographic data can include one or more of a first name of the patient, a last name of the patient, a date of birth of the patient, a government issued identifier of the patient, a telephone number of the patient, or a gender of the patient. The predetermined patient identification criterion can be configurable based on user input to one or more of the incident data exchange system and the medical record digest system.

In the system, the one or more processors can be configured to request supplemental patient identification data from one or more supplemental patient identification data sources in response to a determination that the predetermined patient identification criterion is unsatisfied by the patient identification data from the one or more patient identification data sources; and to generate combined patient identification data including the supplemental patient identification data from the one or more supplemental patient identification data sources and the patient identification data from the one or more patient identification data sources. The predetermined patient identification criterion can be satisfied by the combined patient identification data. The one or more supplemental patient identification data sources can include a medical billing system including a demographic discovery tool. The demographic discovery tool can be configured to retrieve the supplemental patient identification data from a plurality of disparate databases communicatively coupled to the medical billing system. The one or more patient identification data sources can include a computer-aided dispatch (CAD) system; the one or more supplemental patient identification data sources can include an EMS patient charting system; the patient identification data can include one or more of patient medical data or patient demographic data from the CAD system; and the supplemental patient identification data can include one or more of patient medical data or patient demographic data from the EMS patient charting system.

In the system, the one or more patient identification data sources, the one or more supplemental patient identification data sources, the incident data exchange system, and the medical record digest system can form a cloud-based platform. The one or more supplemental patient identification data sources can include a medical billing system; and the one or more processors can be configured to receive the supplemental patient identification data including medical billing data from the medical billing system. The medical billing data can include one or more of medical insurance information of the patient, a healthcare provider information of the patient, one or more billing codes from previous EMS encounters with the patient, supplemental demographic data for the patient, confidence scores associated with initial and/or supplemental demographic data for the patient, or indications of erroneous demographic data for the patient. The one or more supplemental patient identification data sources can include an EMS patient charting system; and the one or more processors can be configured to receive the supplemental patient identification data including one or more of patient medical data or patient demographic data from the EMS patient charting system. The one or more supplemental patient identification data sources can include an EMS navigation system; and the one or more processors can be configured to receive the supplemental patient identification data including at least one item of location data from the EMS navigation system. The at least one item of location data can include one or more of an emergency scene location or an EMS transport destination location. The one or more supplemental patient identification data sources can include the user interface device. The at least one processor can be configured to provide a prompt at the user interface device for a user-entered confirmation of the patient identification data; receive the user-entered confirmation of the patient identification data; and query the incident data exchange system in response to receipt of the user-entered confirmation.

In the system, the one or more supplemental patient identification data sources can include one or more medical devices configured to communicatively couple to the incident data exchange system. The supplemental patient identification data can include patient medical information gathered by the one or more medical devices. The one or more processors can be configured to generate the patient reference code based on a hash and/or encryption of the at least the portion of the patient identification data. The at least one medical record repository can include one or more of a health information exchange, a hospital records database, or a health system database. The at least one processor can be configured to receive at least one medical condition of the patient; and generate the medical record digest based at least in part on the at least one medical condition of the patient, wherein the medical record digest includes patient medical information that is clinically relevant to the at least one medical condition of the patient. The at least one processor can receive the at least one medical condition of the patient in the medical data query. The medical data query can be an automatically generated query from a patient charting system. The medical data query can be a user-entered query captured by the user interface. The at least one processor can receive the at least one medical condition of the patient from the one or more patient identification data sources via the incident data exchange system.

The system can include at least one medical device configured to communicatively couple to the medical record digest system. The at least one processor can be configured to receive one or more physiological signals from the at least one medical device; and generate the medical record digest based on the one or more physiological signals.

In the system, the at least one processor can be configured to serve a user interface to the user interface device; and provide the medical record digest at the user interface. The user interface can be one or more of a visual user interface, an audio user interface, or an augmented reality user interface. The mobile EMS environment can include at least one emergency medical vehicle. The at least one emergency medical vehicle can include one or more of an ambulance, a fire engine, an EMS crew transport vehicle, or a helicopter. The digest system memory and the at least one processor can be disposed in the user interface device. The digest system memory and the at least one processor can be disposed in a cloud server configured to communicatively couple to the user interface device. The medical record digest system can provide a medical record digest application at the user interface device. The patient identification data sources can include one or more of a hospital information system, a medical billing system, a case data store, a charting system, a computer-aided dispatch system, a navigation system, a medical device, and a medical digest system. The one or more processors can maintain, within the exchange system memory, a cross-reference that relates the patient reference code with patient identifiers generated by one or more of the hospital information system, the medical billing system, the case data store, the charting system, the computer-aided dispatch system, the navigation system, the medical device, the medical digest system, and the demographic verifier. The patient identification data from the one or more patient identification data sources for an EMS call can identify a patient involved in an ongoing patient encounter. The one or more processors can be configured to determine at least one format supported by the medical record digest system; and generate the medical record to comply with the at least one format. The one or more processors can be configured to identify at least one subscription to receive the medical record of the patient, the at least one subscription identifying the medical record digest system. The one or more processors can be configured to identify the at least one subscription prior to transmission of the medical record. The at least one subscription can be at least one data structure including fields storing at least one identifier of the at least one subscription and at least one identifier of the medical record digest system.

In one example, an emergency medical services (EMS) medical record acquisition system is provided. The system is configured to provide medical record information to an EMS rescuer in a mobile EMS environment. The system includes a user interface device associated with the mobile EMS environment; at least one patient identification data source; an incident data exchange system configured to communicatively couple to the at least one patient identification data source, and a medical record digest system configured to communicatively couple to the user interface device. The incident data exchange system includes exchange system memory, and one or more processors coupled to the exchange system memory. The one or more processors are configured to receive patient identification data from the at least one patient identification data source for an EMS call for a patient, query at least one medical record repository using the patient identification data, and receive a medical record for the patient from the at least one medical record repository, and transmit the medical record to a medical record digest system. The medical record digest system includes a digest system memory, and at least one processor coupled to the digest system memory. The at least one processor configured to receive the medical record for the patient from the incident data exchange system, organize the received medical record according to a plurality of categories of medical data, store the organized medical record in the digest system memory with the patient identification data, receive a medical data query including the patient identification data and at least one category of medical data from the user interface device, generate a medical record digest based on the medical data query, the medical record digest including at least a portion of the organized medical record corresponding to the at least one category, and provide the medical record digest to the user interface device.

Examples of the system can include one or more of the following features. In the system, to organize the medical record can include to convert the medical record to an indexed medical record according to a plurality of categories of medical data. The at least one processor can be configured to identify the at least the portion of the indexed medical record based on a predetermined list. The predetermined list can be a configurable list specific to an EMS agency. The predetermined list can be statistically derived from cumulative records of an EMS agency. In the system, to convert the medical record to create the indexed medical record can include to assign a plurality of tags within the medical record, wherein each tag associates one or more items of medical data with at least one category from the plurality of categories of medical data.

In the system, the at least one patient identification data source can include a computer-aided dispatch (CAD) service configured to communicatively couple to the incident data exchange system; the plurality of categories of medical data can include a plurality of EMS call types; and the at least one processor can be configured to receive a first medical data query including the patient identification data and a particular EMS call type from the CAD service, query the incident data exchange system using the patient identification data from the CAD service, receive the medical record for the patient from the incident data exchange system, convert the medical record to create an indexed medical record according to a plurality of patient presentations associated with the particular EMS call type, receive a second medical data query including the patient identification data and a particular patient presentation from the user interface device, generate the medical record digest from the indexed medical record based on the second medical data query, and provide the medical record digest to the user interface device. The plurality of categories can include EMS call types. The EMS call types can correspond to patient presentations. The patient presentations can include one or more of cardiac arrest, trauma, sepsis, drug overdose, or lacerations. The EMS call types can include types of emergency incidents. The EMS call types can include types of prescheduled EMS transports.

In the system, the plurality of categories can include types of medical information. The types of medical information can include potential health threats to the EMS rescuer. The types of medical information can include one or more of existing patient conditions, patient allergies, or patient medications. The types of medical information can include one or more of transmittable diseases or chronic conditions. The types of medical information can include one or more field names for an electronic patient chart. The at least one processor can be configured to apply one or more of a rule set or a machine learning process to the medical record to associate the plurality of tags with information in the medical record.

In the system, the at least one processor can be configured to receive the medical data query from the user interface device. The medical data query can be based on user input to the user interface device. The medical data query can be automatically generated by a patient charting application of the user interface device. The patient charting application can be configured to receive one or more physiological signals from at least one medical device; and automatically generate the medical data query based on the one or more physiological signals.

In the system, to transmit the medical record digest to the user interface device can include to serve a graphical user interface to the user interface device, the graphical user interface including at least one control configured to render the medical record digest. The at least one control can be configured to render the medical record digest within a problems, allergies, and medications structure. The at least one control can be configured to render the medical record digest chronologically. The at least one control can be configured to render the medical record digest according to a relative severity of clinical impact. The user interface device can be one or more of a display screen, a microphone and speaker device, or an augmented reality interface device.

In the system, the mobile EMS environment can include at least one emergency medical vehicle. The at least one emergency medical vehicle can include an ambulance, a fire engine, an EMS crew transport vehicle, or a helicopter.

In the system, the at least one medical record repository can include one or more of a health information exchange, a hospital records database, or a health system database. The digest system memory and the at least one processor can be disposed in the user interface device. The digest system memory and the at least one processor can be disposed in a cloud server configured to communicatively couple to the user interface device. The medical record digest system can provide a medical record digest application at the user interface device. The at least one patient identification data source can include one or more of a hospital information system, a medical billing system, a case data store, a charting system, a computer-aided dispatch system, a navigation system, a medical device, and a medical digest system. The at least one patient identification data source for the EMS call can identify a patient involved in an ongoing patient encounter. The one or more processors can be configured to determine at least one format supported by the medical record digest system; and generate the medical record to comply with the at least one format.

In the system, the one or more processors can be configured to identify at least one subscription to receive the medical record of the patient, the at least one subscription identifying the medical record digest system. The one or more processors can be configured to identify the at least one subscription prior to transmission of the medical record. The at least one subscription can be at least one data structure including fields storing at least one identifier of the at least one subscription and at least one identifier of the medical record digest system.

In one example, a cloud-based platform for emergency medical services (EMS) medical record acquisition in a mobile EMS environment is provided. The platform includes a computer-aided dispatch (CAD) system; a medical billing system; an EMS charting system; an incident data exchange system configured to communicatively couple to the CAD system, the medical billing system, the EMS charting system, a medical record digest system, and an EMS navigation system via a network; and the medical digest system. The incident data exchange system includes exchange system memory and one or more processors coupled to the exchange system memory. The one or more processors are configured to receive first patient identification data and EMS call type data from the CAD system, wherein the EMS call type data is associated with an EMS call for a patient, provide the first patient identification data to the medical billing system, receive supplemental patient identification data from the medical billing system, request a medical record for the patient from at least one medical record repository using the first patient identification data and the supplemental patient identification data, receive the medical record for the patient from the at least one medical record repository, and transmit the medical record to the medical record digest system. The medical record digest system is configured to communicatively couple to the CAD system, the medical billing system, the EMS charting system, the incident data exchange system, and the EMS navigation system via a network. The medical record digest system includes a digest system memory and at least one processor coupled to the digest system memory. The at least one processor is configured to receive the medical record for the patient from the incident data exchange system, convert the medical record to create an indexed medical record according to at least one taxonomy, receive a medical data query from one or more of the CAD system or the EMS charting system, generate a medical record digest from the indexed medical record based on the medical data query, the medical record digest including a portion of the indexed medical record that is clinically relevant to the EMS call type data, and transmit the medical record digest to the one or more of the CAD system or the EMS charting system.

Examples of the platform can include one or more of the following features. In the platform, the at least one medical record repository can include one or more of a health information exchange, a hospital records database, or a health system database. The supplemental patient identification data from the medical billing system can include second patient identification data. The one or more processors can be configured to query the at least one medical record repository using the first and the second patient identification data. The supplemental patient identification data from the medical billing system can include patient provider and insurance information and the at least one processor is configured to merge the supplemental patient identification data from the medical billing system into the medical record digest; and transmit the medical record digest to the EMS charting system. The EMS charting system can be configured to serve a user interface to a user interface device in the mobile EMS environment; and provide the medical record digest at the user interface.

In the platform, the exchange system memory can include a predetermined patient identification criterion for the first patient identification data, the predetermined patient identification criterion including a list of identification data items to distinguish between multiple patients represented in the at least one medical record repository; and the one or more processors can be configured to determine whether the first patient identification data satisfies the predetermined patient identification criterion. The one or more processors can be configured to request the supplemental patient identification data from one or more of the EMS charting system or the medical billing system; receive the supplemental patient identification data; combine the supplemental patient identification data with the first patient identification data; and query the at least one medical record repository based on the combined supplemental patient identification data and first patient identification data.

In the platform, the supplemental patient identification data can include one or more of patient medical data, patient demographic data, patient insurance data, or patient medical provider data. The one or more processors can be configured to generate a patient reference code based on at least a portion of one or more of the first patient identification data or the supplemental patient identification data; and the at least one processor can be configured to store the indexed medical record with the patient reference code in the digest system memory. The at least one processor can be configured to provide the patient reference code to one or more of the CAD system or the EMS charting system; and receive the medical data query including the patient reference code from the one or more of the CAD system or the EMS charting system. The at least one processor can be configured to store the medical record with the patient reference code in the digest system memory.

The platform can include a medical records database configured to communicatively couple to at least the incident data exchange system. In the platform, the medical records database can be only accessible via the cloud-based platform; the medical records repository can include one or more of a health information exchange, a hospital records database, or a health system database accessible via the cloud-based platform and via third party applications outside of the cloud-based platform; and the one or more processors can be configured to store the indexed medical record in the medical records database with the patient reference code. The medical records database can be configured to communicatively couple to at least one medical device in the mobile EMS environment.

The platform can include a medical records database configured to communicatively couple to the CAD system, the medical billing system, the EMS charting system, incident data exchange system, and the medical record digest system. In the platform, the medical records database can be only accessible via the cloud-based platform. The medical records repository can include one or more of a health information exchange, a hospital records database, or a health system database accessible via the cloud-based platform and via third party applications outside of the cloud-based platform; and the one or more processors can be configured to transmit the indexed medical record to the medical records database for storage. The EMS call can be a first EMS call for the patient. The medical record digest can be a first medical record digest for the patient. The one or more processors can be configured to receive the first patient identification data and the supplemental patient identification data for a second EMS call for the patient, wherein the second EMS call is for a same patient as the first EMS call and occurs subsequent to the first EMS call, bypass the request for the medical record from the at least one medical record repository, update the medical records database based on second EMS call, and transmit an updated medical record to the medical record digest system; and the at least one processor can be configured to receive the updated medical record from the incident data exchange system, retrieve a previously stored indexed medical record from the medical records database based on the first patient identification data and the supplemental patient identification data in lieu of the medical record; and generate a second medical record digest from the previously stored indexed medical record and the updated medical record for the second EMS call for the patient. The at least one processor can be configured to request medical billing codes for the patient from the incident data exchange system for a time period between the first EMS call and the second EMS call; and update the previously stored indexed medical record based on the medical billing codes. The medical records database can be configured to communicatively couple to at least one medical device in the mobile EMS environment.

The platform can further include the EMS navigation system. The EMS navigation system can be configured to communicatively couple to the incident data exchange system. The one or more processors can be configured to receive location data for the patient from the EMS navigation system. The one or more processors can be configured to query the at least one medical record repository using the location data to supplement the first patient identification data. The location data can include an emergency scene location. The at least one processor can be configured to generate the medical record digest based on the emergency scene location. The at least one processor can be configured to include the portion of the medical record that is clinically relevant to attributes of the emergency scene location.

In the platform, at least one processor can be configured to request billing information for the patient from the incident data exchange system; and identify the portion of the indexed medical record that is clinically relevant to the EMS call type data based at least in part on the billing information. The medical record digest system can be configured to communicatively couple to at least one medical device in the mobile EMS environment. The at least one processor can be configured to receive one or more physiological signals from the at least one medical device, and identify the portion of the indexed medical record that is clinically relevant to the EMS call type data based at least in part on the physiological signals. The mobile EMS environment can include at least one emergency medical vehicle.

The platform can include a demographic verifier configured to receive initial patient demographic data from one or more of the CAD system, the EMS charting system, or the medical record digest system; search one or more databases for supplemental patient demographic data based on the initial patient demographic data; and store the supplemental patient demographic data to the medical record for the patient. The incident data exchange system can be configured to create a patient records data query based on the supplemental patient demographic data. The demographic verifier can be configured to calculate confidence scores for the initial and the supplemental patient demographic data; and provide the confidence scores to the incident data exchange system, wherein the incident data exchange system is configured to select demographic data for use in the patient records data query based on the confidence scores. The demographic verifier can be configured to flag erroneous data in the initial patient demographic data; and the incident data exchange system can be configured to exclude erroneous data from the patient records data query. The platform can further include one or more of a hospital information system, a medical billing system, a case data store, a charting system, a computer-aided dispatch system, a navigation system, a medical device, and a medical digest system. The patient identification data from the CAD can identify a patient involved in an ongoing patient encounter. The one or more processors can be configured to determine at least one format supported by the medical record digest system; and generate the medical record to comply with the at least one format.

In the platform, the one or more processors can be configured to identify at least one subscription to receive the medical record of the patient, the at least one subscription identifying the medical record digest system. The one or more processors can be configured to identify the at least one subscription prior to transmission of the medical record. The at least one subscription can be at least one data structure include fields storing at least one identifier of the at least one subscription and at least one identifier of the medical record digest system.

In one example, an incident data exchange system is provided. The incident data exchange system is adapted to communicate medical records to endpoints authorized to receive the medical records. The incident data exchange system includes a memory storing a plurality of associations between a plurality of patients and a plurality of endpoints storing medical data regarding the plurality of patients; and at least one processor coupled to the memory and configured to receive, from an endpoint, incident data identifying a patient, identify at least one subscription to receive medical records of the patient, the at least one subscription identifying at least one endpoint, identify one or more endpoints of the plurality of endpoints that are associated with the patient within the plurality of associations, the one or more endpoints including at least one health information exchange distinct from the incident data exchange system, transmit one or more application programming interface (API) calls to the one or more endpoints, each API call requesting medical data associated with the patient, receive one or more API responses to the API calls, each API response of the one or more API responses specifying the medical data associated with the patient, and transmit, to the at least one endpoint within one or more medical records, the incident data and the medical data specified by the one or more API responses.

Examples of the system can include one or more of the following features. In the system, the one or more endpoints can include one or more of a hospital records database, a medical billing system, a case data store, a charting system, a computer-aided dispatch system, a navigation system, a medical device, a medical digest system, a health information exchange, or a health system database. The incident data can describe an ongoing patient encounter. The at least one processor can be configured to determine at least one format supported by the at least one endpoint; and generate, from the incident data and the medical data, the one or more medical records to comply with the at least one format. The at least one subscription can be at least one data structure can include fields storing at least one identifier of the at least one subscription and at least one identifier of the at least one endpoint. The endpoint can be a computer-aided dispatch system.

In the system, the memory can include a predetermined patient identification criterion; and the at least one processor can be configured to determine whether patient identification data within the incident data satisfies the predetermined patient identification criterion. The predetermined patient identification criterion can include a list of identification data items necessary to include in a query to distinguish between multiple patients represented in the one or more endpoints. The list of identification data items can include patient demographic data. The patient demographic data can include one or more of a first name of the patient, a last name of the patient, a date of birth of the patient, a government issued identifier of the patient, a telephone number of the patient, or a gender of the patient. The predetermined patient identification criterion can be configurable based on user input to one or more of the incident data exchange system. The at least one processor can be configured to request supplemental patient identification data from the one or more endpoints in response to a determination that the patient identification data within the incident data does not satisfy the predetermined patient identification criterion; and generate combined patient identification data including the supplemental patient identification data and the patient identification data within the incident data. The predetermined patient identification criterion may be unsatisfied by the patient identification data within the incident data but satisfied by the combined patient identification data.

In the system, the one or more endpoints and the incident data exchange system can form a cloud-based platform. The one or more endpoints can include a medical billing system; and the at least one processor can be configured to receive the supplemental patient identification data including medical billing data from the medical billing system. The medical billing data can include one or more of insurance information of the patient, a healthcare provider of the patient, one or more billing codes from previous EMS encounters with the patient, supplemental patient demographic data for the patient, confidence scores associated with initial and/or supplemental patient demographic data for the patient, or indications of erroneous patient demographic data for the patient. The one or more endpoints can include an EMS patient charting system; and the at least one processor can be configured to receive the supplemental patient identification data including one or more of patient medical data or patient demographic data from the EMS patient charting system. The one or more endpoints can include an EMS navigation system; and the at least one processor can be configured to receive the supplemental patient identification data including at least one item of location data from the EMS navigation system. The at least one item of location data can include one or more of an emergency scene location or an EMS transport destination location.

In the system, the one or more endpoints can include a user interface device. The one or more endpoints can include one or more medical devices configured to communicatively couple to the incident data exchange system. The supplemental patient identification data can include patient medical information gathered by the one or more medical devices. The at least one processor can be configured to generate a patient reference code based on a hash and/or encryption of the at least a portion of patient identification data.

BRIEF DESCRIPTION OF THE DRAWINGS

Various aspects of the disclosure are discussed below with reference to the accompanying figures, which are not intended to be drawn to scale. The figures are included to provide an illustration and a further understanding of various examples and are incorporated in and constitute a part of this specification but are not intended to limit the scope of the disclosure. The drawings, together with the remainder of the specification, serve to explain principles and operations of the described and claimed aspects and examples. In the figures, each identical or nearly identical component that is illustrated in various figures is represented by a like numeral. For purposes of clarity, not every component may be labeled in every figure. A quantity of each component in a particular figure is an example only and other quantities of each, or any, component could be used.

FIG. 5A is a record diagram illustrating a medical record in accordance with at least one example disclosed herein.

DETAILED DESCRIPTION

Figure 1:
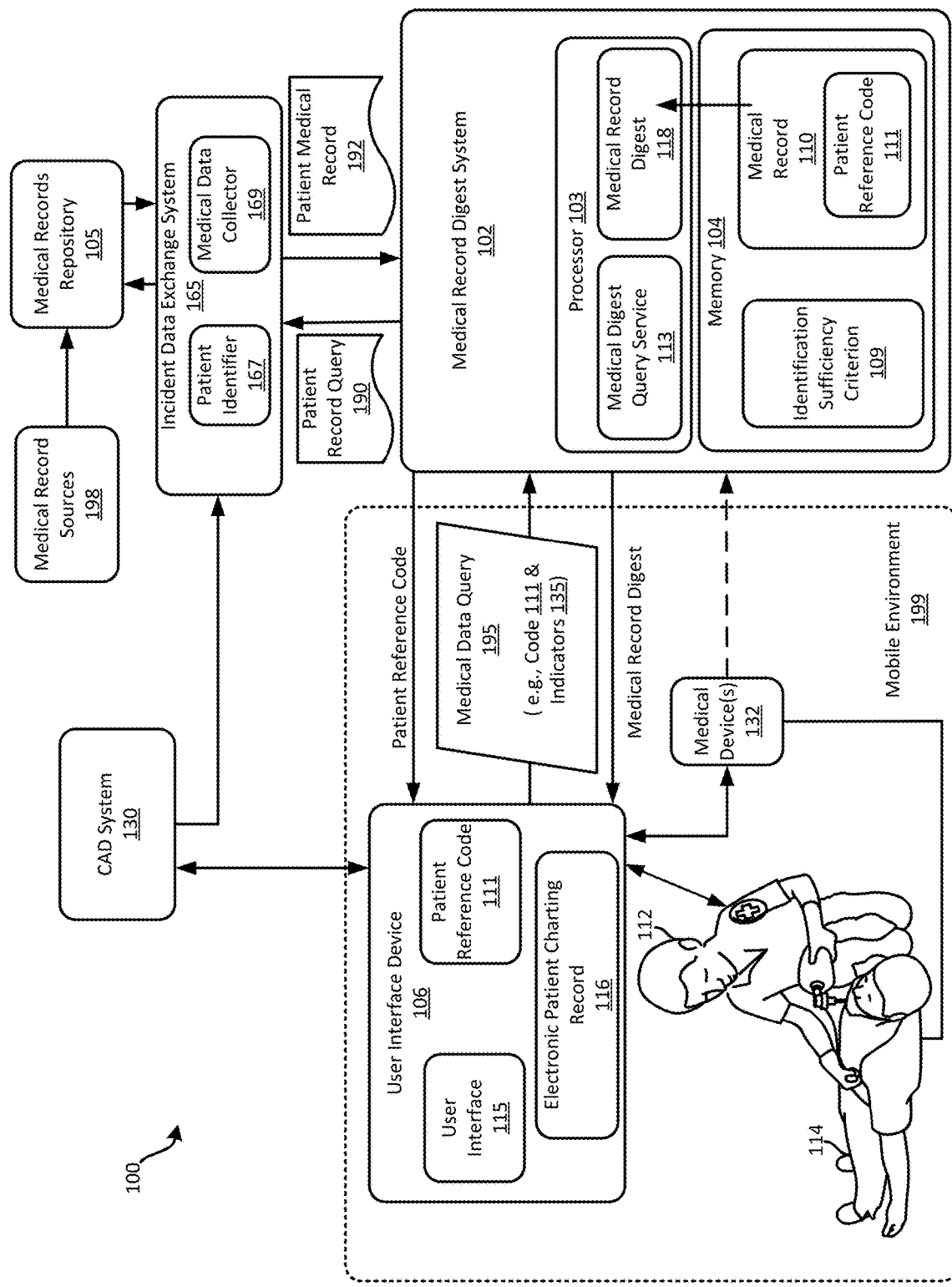
FIG. 1 is a schematic block diagram of a medical record digest system interoperating with an incident data exchange system to exchange patient data with a CAD system and a medical records repository in accordance with at least one example disclosed herein.

When a patient is treated by EMS, particularly in an emergent situation, access to the health history of the patient can improve the efficacy of care and increase the likelihood of a positive outcome. Moreover, access to the patient's health history can also help care providers avoid threats to their own health and safety. However, practical constraints on the availability and usefulness of a patient's health history to EMS exist at present.

For example, consider an illustrative scenario of a crew of EMS care providers in an ambulance being called upon to treat a patient suffering from an emergency medical condition (e.g., cardiac arrest, trauma, respiratory distress, drug overdose, etc.) and to transport the patient to a hospital. In this situation, depending on the condition of the patient, the care providers may be unable to unambiguously determine the identity of the patient. Without a definitive identification, accessing the patient's health history records is difficult. Furthermore, even where the identity of the patient is unambiguous, reviewing the entire health record of a patient to find information relevant to the current emergent situation can be time consuming, which can prevent EMS care providers from even attempting to make use of the health record. However, the lack of this health history information may significantly reduce the efficacy of care.

Thus, and in accordance with at least some examples disclosed herein, systems and methods are provided for more effectively identifying EMS patients and for providing portions of the patient's health record that are clinically relevant to the patient encounter.

The medical record digest systems and processes described herein can aid or enable the provision of situationally dependent medical record(s) distillations that provide guidance for the care provider in a context based workflow. In EMS, the context based workflow or situational dependence of the medical record distillations may differ from clinical guidance for physician care, for example, in a doctor's office or hospital environment. The critical context or situation for EMS is the patient presentation and immediate interventions provided to the patient in response to the patient presentation.

For example, a patient presenting with respiratory distress (RD) generally requires a rapid and accurately targeted intervention. The EMS care provider may need to identify and implement the appropriate efficacious intervention within minutes in order to ensure that the patient stays alive and neurologically intact. Such an intervention includes actions that contribute directly to the care of the patient's presenting condition(s) and may determine the disposition of the patient. The intervention may or may not treat the etiology of the presenting condition(s). However, if the presenting condition(s) remain unchanged by an intervention, the patient may not live long enough for a treatment of the root cause.

For example, a patient may exhibit RD due to congestive heart failure (CHF). In this case, the RD has a cardiac etiology. An intervention to relieve the RD, such as providing oxygen to the patient to remedy hypoxemia, is necessary to keep the patient alive and neurologically intact until the cardiac etiology can be diagnosed and addressed with treatment. The treatment for the heart failure may be separate from the oxygen intervention. For example, this treatment may include angioplasty, high blood pressure medication, and/or arrhythmia medication.

In emergent care, diagnosis of the etiology of a presentation is of secondary importance to providing immediate interventions for the presentation regardless of etiology. However, knowledge of possible etiologies as determined from a patient's medical records likely improves the efficacy and efficiency of the provided interventions. For example, if a patient is in RD and EMS has access to medical records that indicate a chronic condition like asthma, EMS care provider can immediately tailor the intervention to the asthma as the cause of the RD to better enable the intervention to relieve the presenting hypoxia. However, the EMS care provider is unlikely to have the time or the opportunity to go further with any verification of asthma as the etiology or in providing long term treatments to alleviate the asthma. Additionally, the medical records may enable the EMS care provider to avoid interventions that may worsen the patient's condition due to their medical history. For example, if a patient is allergic to latex, use of latex gloves by EMS may compound the patient's RD presentation.

The distillation of the patient's medical records for use by EMS in this context is directed at highlighting information relevant to the patient's presentation. In contrast, where the ultimate goal of the physician is to diagnose and treat the etiology of a patient's presentation, the goal of a review of a patient's medical history for diagnostic purposes is to gather information about all conditions that may enable the physician to diagnose a root cause. For example, the etiology of the patient in RD may be lung cancer and the oncologist may look to the medical records to guide clinical decisions about tests that will confirm the presence of lung cancer and guide decisions about the particular treatments to address and cure the lung cancer (e.g., surgery, chemotherapy, radiation, etc.). The EMS care for this same patient will entail providing enough oxygen through proper delivery means to get the patient in RD to the oncologist as opposed to having the patient die at home or en route to the oncologist. EMS will not be concerned with the origins or specific details about the lung cancer causing the RD. Thus the medical digest system for EMS differs from a medical record summary system for physicians at least in terms of the type and extent of information that is needed to achieve the different goals of these two types of care providers.

The medical digest system for EMS also differs from a medical record summary system for physicians given that EMS is working with the patient over a significantly shorter and rapidly evolving time frame (e.g., a period of minutes or 1-2 hours for EMS as opposed to days, weeks, or months for a physician). The rapidly evolving time frame may require time adaptive information from medical records. In other words, the information of use to EMS may change over a period of minutes as they triage and identify patient presentations and emergent medical needs. Additionally, EMS may be caring for multiple patients at one time (e.g., a scene of a car accident or fire). Further, EMS is often encountering a patient for the first time and is not limited to a specific area of medical inquiry. In contrast, a physician usually has an ongoing relationship with a patient and can review a medical record in light of this relationship. Further a physician is generally working in a specialty area and may request or need a summary of medical record information relevant to that specialty area. For example, an obstetrician is specifically looking for medical record summary information related to obstetrics or obstetrical causes of a patient presentation. Similarly, a cardiologist is looking for medical record summary information related to cardiac etiologies. The problem of identifying the summary information needed for EMS is complicated by the fact that EMS does not have an ongoing relationship and is looking for information organized according to patient presentation rather than according to etiology.

At least some examples described herein are directed to an EMS medical record acquisition system that is built upon a platform comprising several medical information systems. FIG. 1 illustrates a platform 100, for example a SaaS platform, in accordance with these examples. As shown in FIG. 1, the platform 100 includes and implements a medical record digest system 102 in accordance with some examples. The digest system 102 can, according to examples of the present disclosure, track responses to emergency medical events as they unfold to determine the identity of patients in need of care and to provide care providers with clinically relevant and actionable medical information at the point of care. This clinically relevant and actionable medical information is drawn from the patient's medical records and is specific to the emergency medical event encountered by the patient. As such, the information may determine, change, or adjust treatments and/or interventions provided to the patient. For instance, protocol followed within standard procedures may be changed or adjusted in light of the information, thereby altering the course of action from standard procedures. Moreover, clinically relevant and actionable medical information may include medical information that affects later procedures, interventions, and/or treatments. As such, this information may cause a change from a first protocol to a second protocol or an adjustment based on options within a protocol. Alternatively or additionally, the information may cause a change to procedures, interventions, and/or treatments that involves medical options that are outside of a protocol. Clinically relevant and actionable medical information may include information that indicates a possible cause, or etiology, of a patient presentation. For example, if a patient who presents with respiratory distress (RD) has a medical history of asthma, then asthma is a likely etiology of the RD. With this knowledge, interventions can be tailored to the likely etiology. As another example, a penicillin or latex allergy may contraindicate the use of penicillin or latex. Additionally or alternatively, the clinically relevant and actionable information may determine, change, or adjust procedures, actions, and/or precautions taken by the EMS care providers or other EMS personnel. For instance, the clinically relevant and actionable information may include information regarding contagious conditions, blood borne diseases, psychiatric issues, etc. that may affect an EMS care provider's approach to self-care in providing treatments or interventions to the patient. Some examples of clinically actionable and relevant information follow. A medication history of Viagra may contraindicate the use of nitroglycerin in treating a cardiac condition. A recent COVID positive test may require EMS care providers to wear additional personal protective equipment. An HIV/AIDS condition may require additional blood handling caution for EMS. A patient history that indicates Alzheimer's disease may result in additional preparation by EMS care providers for possible cognitive issues.

Continuing with the example of FIG. 1, in an implementation, the digest system 102 may interoperate with several medical information systems within the platform 100 to uniquely identify a patient as early as possible within each emergency response. In some examples, the digest system 102 incrementally collects patient identification data from these medical information systems until the patient identification data is sufficient to uniquely identify the patient. The digest system 102 may, in some examples, use the patient identification data to uniquely identify the patient through execution of processes internal to the digest system 102 and/or through execution of processes that interoperate with an incident data exchange system 165. In an implementation, once the patient is uniquely identified, the digest system 102 gathers, either directly or via the exchange system 165, the patient's medical records from other subsystems within the platform and from systems external to the platform. The digest system 102 indexes the medical record(s) according to a taxonomy to enable rapid segmentation of the record(s) by medical data indicator (e.g., medical data categories). In this way, as details regarding the patient's medical condition emerge over the course of a patient encounter, the digest system 102 can quickly provide portions of the medical record(s) that are pertinent to the emerging details. For example, a CAD may receive an emergency call for an automobile accident with information that a victim has suffered a broken bone. Thus, the initial patient medical status based on the information from the CAD may be trauma and the digest system 102 may provide the medic with a distillation, or digest, of the patient's health history that is clinically relevant to trauma. Once the medic is on scene and providing interventions for trauma, the victim may present with cardiac or respiratory distress. For example, the stress of the accident and/or fumes from a car fire might cause these presentations. Thus, the medic may benefit from a refreshed digest of the patient's health record(s) that is clinically relevant to cardiac or respiratory distress. As another example, the medical history of the victim may include indications of cardiac disease (e.g., a pacemaker, a wearable defibrillator, or medications for treating cardiac disease). Thus the original digest targeted to trauma may also include warnings of chronic conditions, like cardiac disease, that may require interventions during the patient encounter. By providing such a digest of the patient's medical record(s) to the care provider at the point of care, the quality of treatment provided to the patient, and the likelihood of a positive outcome, are increased.

As shown in FIG. 1, the platform 100 includes, in addition to the digest system 102 and the exchange system 165, a CAD system 130, a medical records repository 105, and a mobile environment 199. The CAD system 130, the digest system 102, the medical records repository 105, the exchange system 165, and the mobile environment 199 may be in data communication with one another via one or more networks. In some examples, the CAD system 130 is configured to receive data regarding emergency calls from a dispatcher and, in response thereto, create a call record. This call record can include, for example, data specifying a type of call, persons involved in the call, and actions taken by the dispatcher to address the call. Where the call is a medical emergency, the dispatcher may enter or verify patient identification data within the call record. This patient identification data may identify a patient in need of medical attention. Such information can include, for example, primary identification data such as a patient's name, gender, date of birth, a patient reference code (e.g., the patient reference code 111 described further below) or a government issued identification number (e.g., social security number, driver's license number, etc.). Patient identification data can also include secondary identification data that identifies the patient less directly but that is still relevant to determining the identity of the patient. Examples of secondary identification data include address, telephone number, vehicle identification data, primary identification data of close relatives, and the like.

In one example illustrated by FIG. 1, a patient 114 may be found unconscious in a public location by a bystander. The bystander may call a local emergency response telephone number (e.g., 911) to report the patient's situation and request help. The dispatcher answering the call may request that the bystander provide whatever information is readily available regarding the patient's location and identity. The bystander may respond with the street address of her present location. After searching the patient 114 for some form of identification, the bystander may further respond with the patient's first and last name, date of birth, height, weight, eye color, residence address, and driver's license number as shown on the patient's driver's license. The dispatcher can enter this information into the CAD system 130 to make it part of the call record. The dispatcher can further interact with the CAD system 130 to execute a dispatch order requesting that an emergency care provider, such as the care provider 112, travel to the street address provided by the bystander to render assistance. In some examples, the CAD system 130 is configured to autonomously route the care provider 112 to the street address in response to the dispatch order. In addition, in some examples, the CAD system 130 is also configured to autonomously transmit a message to the exchange system 165 in response to execution of a dispatch order, as shown in FIG. 1. This message can include patient identification data for the patient 114 from the call record as well as information descriptive of a medical condition of the patient 114 (e.g., that the patient 114 was found unconscious).

As shown in FIG. 1, the exchange system 165 may receive the message from the CAD system 130 and create an incident record that associates the data included in the message with the CAD system 130. In some examples, the exchange system 165 may mark a status of the incident record as open and attempt to uniquely identify the patient (e.g., through execution of a patient identifier 167) to generate an identification confidence score. The exchange system 165 may store, within the incident record, an association between the CAD system 130, a patient reference code that uniquely identifies the patient, the confidence score, and the data included in the message. Further, based on the open status of such an incident record, the exchange system 165 may interoperate (e.g., through execution of a medical data collector 169) with other systems (e.g., the medical records repository 105) to gather medical data regarding the patient from the other systems and to notify the other systems of the open incident record.

Upon arrival at the street address, the care provider 112 may quickly setup the mobile environment 199 and begin assessing and treating the patient 114. As shown in FIG. 1, the mobile environment 199 includes one or more medical device(s) 132 and a user interface device 106 in data communication (e.g., via a local network) with the medical device(s) 132. The user interface device 106 can be a tablet, smartphone, wearable device, and/or other mobile computing device and/or a combination of mobile devices. In an implementation, the local network within the mobile environment 199 includes a short range wired or wireless connection and can be established in an ad hoc manner. The wireless connection may include, for example, WiFi®, Bluetooth®, and/or near-field communications.

Further, as shown in FIG. 1, optionally both the user interface device 106 and the medical device(s) 132 may be in data communication with the digest system 102. The digest system 102, in turn, may be in data communication with the exchange system 165. The digest system 102 may, using processes described further below, construct a medical record digest using the medical data of the patient gathered by the exchange system 165.

After or during setup of the mobile environment, the care provider 112 may attempt to elicit a response from the patient, take the patient's pulse, and the like. In this example, being unable to elicit a response or detect a pulse, the care provider 112 fits the patient 114 with the medical device(s) 132 including a defibrillator, powers on the defibrillator, and quickly reviews a user interface 115 of the user interface device 106 for information regarding the defibrillator and the patient. In this example, the user interface 115 presents the medical record digest. The medical record digest includes a history of cardiac events from which the patient 114 has suffered and a notification that a pacemaker was implanted in the patient 114 seven years ago. This notification can be rendered via, for example, a text message, email, or more specialized application (e.g., a medical digest application described below with reference to FIG. 3B). The care provider 112 is thus provided with a portion of the patient's medical record(s) that is pertinent to the medical event encountered by the patient 114.

Several features of the platform 100 interoperate to provide the care provider 112 visibility to the medical record digest described above. One of these features is the exchange system 165. As shown in FIG. 1, the exchange system 165 interoperates with the CAD system 130 and/or the repository 105 to identify the patient and/or gather medical data regarding the patient. In at least one example, to support such interoperation, the exchange system 165 is configured to expose one or more application programming interfaces (APIs) that support health data exchange standards, such as state-wide health data exchange standards, regional health data exchange standards, HL7 message standards, and National Council for Prescription Drug Programs (NCPDP) script standards.

In some examples, the exchange system 165 is configured to operate in an ad-hoc mode. When operating in the ad-hoc mode, the exchange system 165 receives and responds to requests (queries) for medical data regarding patients. In these examples, the exchange system 165 receives, for example, patient record queries 190, collects medical data responsive to the patient record queries (based on internally stored medical data or medical data acquired from other systems), and communicates patient medical records 192 in response to the patient record queries 190. Alternatively or additionally, some implementations of the exchange system 165 are configured to operate in a subscription/publication mode. When operating in the subscription/publication mode, the exchange system 165 receives incident information from previous registered source endpoints (e.g., from the CAD system 130), identifies registered destination endpoints (e.g., the digest system 102) that are subscribed to receive patient medical records 192 regarding patients involved in the incidents, identifies/gathers medical data for the patients, and communicates patient medical records 192 to the subscribed endpoints. An introductory discussion of two processes implemented within the exchange system 165 follows. More details regarding the exchange system 165 are provided with reference to FIG. 2C below.

In some implementations, the patient identifier 167 of the exchange system 165 extracts patient identification data from messages received from the CAD system 130 and executes a patient identification process in an attempt to uniquely identify a patient using the patient identification data. In these implementations, the patient identification process outputs an identification confidence score that indicates a likelihood that the patient identification process uniquely identified the patient. One example of such a patient identification process is described further below with reference to FIG. 2B. Further, in some implementations, the patient identifier 167 identifies a patient reference code previously generated for the patient (e.g., the patient reference code 111 described further below) or generates a new patient reference code for the patient. In some examples, the patient identifier 167 identifies or generates the patient reference code upon determining that the patient identification data is sufficient to uniquely identify the patient 114, although this is not a requirement. Patient reference codes uniquely identify individual patients within the system and can be utilized by other systems for the same purpose. In some examples, the patient identifier 167 is configured to generate new patient reference codes based on a hash and/or encrypted value of at least the portion of the patient identification data. For instance, in at least one example, the patient identifier 167 generates the patient reference code by calculating a hash value of a concatenation of the patient's first name, last name, and government issued identification number and storing the calculated hash value as a patient reference code for the patient. Other combinations of data items within patient identification data are possible. For instance, in at least one implementation, the combinations of data items used to generate patient reference codes are the same combination of data items specified by the identification sufficiency criterion 109 described further below. In another example, the patient reference code is a globally unique identifier (GUID) generated without reference to any patient identification data.

In certain examples, the medical data collector 169 of the exchange system 165 is configured to receive patient identification data and to identify a medical record repository (e.g., the repository 105) that stores medical information regarding the patient identified by the patient identification data. In one implementation, the data collector 169 is configured to identify the repository 105 via a data structure that associates patient identification data with repository identifiers. In this implementation, the data collector 169 identifies the repository 105 by locating an association (e.g., a row/record) within the data structure in which a copy of the patient identification data and an identifier of the repository 105 is stored.

In some examples, the data collector 169 is also configured to generate a query for the medical records of the patient and to transmit the query to the repository 105. For instance, in some examples, the data collector 169 can be configured to generate the query to the repository 105 in a format (e.g., Health Level Seven (HL7)) supported by the repository 105 and that includes data items from the patient identification data required by the repository 105. In these examples, the data collector 169 is configured to identify the format supported by the repository 105 via a data structure that associates repository identifiers with supported formats. For instance, the data collector 169 can identify the format supported by the repository 105 by locating an association (e.g., a row/record) within the data structure in which an identifier of the repository 105 and an identifier of the supported format are is stored. The generated query can request some or all of the medical records for the patient using at least a portion of the patient identification data. The data collector 169 is also configured to transmit the query to the repository 105, receive and parse the response including the medical record, and store the medical record in a memory as a medical record in association with the patient identification data. It should be noted that the repository can be, for example, an EHR system, a HIE system, or some other source of patient data.

In certain examples, the exchange system 165 is configured to communicate a patient medical record 192 specifying the patient reference code for the patient, the confidence score, and/or other data from the incident record or gathered by the data collector 169 to subscribers registered and authorized to receive patient medical records 192 from the exchange system 165. In an example illustrated by FIG. 1, these registered and authorized subscribers include the digest system 102.

As shown in FIG. 1, the digest system 102 interoperates with the exchange system 165 to receive and distill one or more patient medical records 192. In some examples, the medical records 192 are records previously stored in the exchange system 165 or concurrently gathered by the medical data collector 169 from the repository 105. In either case, the medical records 192 may include medical data generated by one or more third party medical record sources 198. These sources 198 may include any number of EHR systems operated by healthcare facilities and/or HIE systems operated by local, state, or regional governments and/or independent/private HIEs. As such, these sources may include one or more of a physician's office, a clinic, a hospital or hospital system, an urgent care center, an EMS agency, a pharmacy or pharmacy system, a prescription medical device supplier, a medical billing service, and/or another entity that utilizes, receives and/or generates patient medical data and may be data consumers as discussed below in regard to FIG. 9. The medical records in the repository 105 may include historical medical records and data generated and stored prior to a current medical encounter and/or may include contemporaneous medical records and data generated and stored in conjunction with a current medical encounter. In this way, the medical record digest system 102 may use the medical information relevant to the patient to compile the medical record digest 118 and tailor the medical record digest 118 to a currently known or observed medical status of the patient.

The repository 105 can include records descriptive of a patient's medical history. These records can include a variety of patient medical information, such as medical history prior to an encounter, symptoms that lead to an encounter, any diagnosis identified during the encounter, treatments prescribed as a result of the encounter, and outcomes resulting from the treatments. In at least one example, the repository 105 is configured to expose one or more APIs that support health data exchange standards, such as state-wide health data exchange standards, regional health data exchange standards, HL7 message standards, and National Council for Prescription Drug Programs (NCPDP) script standards. It should be noted that the repository 105 may include data generated by one organization or by other organizations or networks or third-party sources, such as hospitals, clinics, doctors' offices, pharmacies, urgent care centers, EMS agencies, medical device sources, rehabilitation centers, mental health centers, and/or other care providers that receive and/or generate patient medical data. The repository 105 can be, for example, a HIE, a hospital records database, a health system database, a pharmacy system database, a business-to-business entity, or a combination thereof.

The digest system 102 includes a processor 103 coupled to a memory 104. The memory 104 is configured to store at least one identification sufficiency criterion 109 and a medical record 110. The medical record 110 is configured to store (and/or otherwise be associated with) a patient reference code 111. The processor 103 is configured to implement a medical digest query service 113 and other processes that culminate in the creation of a medical record digest 118.

For instance, in some examples, the processor 103 is configured to utilize the criterion 109 to determine whether the patient identification data and/or confidence score received from the exchange system 165 is sufficient to uniquely identify the patient 114 from among other patients (e.g., within a given repository). Alternatively or additionally, the processor 103 can establish the criterion 109 as a level of patient identification required to receive published patient medical records from the exchange system 165 when setting up a subscription for the same. The criterion 109 may, for example, specify one or more combinations of data items that are, when populated with values, sufficient to uniquely identify the patient. Examples of these data items can include demographic data of the patient, such as a first name of the patient, a last name of the patient, a date of birth of the patient, a government issued identifier of the patient, a telephone number of the patient, and/or a gender of the patient. For instance, in one example, the criterion 109 specifies that the patient identification data is sufficient where the patient identification data includes values for a first name, last name, date of birth, and gender of the patient. In some examples, the criterion 109 specifies a threshold value that, when met or exceeded by the value of the confidence score, indicates that the patient identification data is sufficient. Other data items and/or combinations of data items may be specified by the criterion 109. In some examples, the criterion 109 is configurable via a user interface exposed by the digest system 102. By providing this configurable, predetermined patient identification criterion, the digest system 102 enables a health care organization to implement a policy of its choosing in regards to the level of certainty required to identify a patient. Such a policy can ensure patient safety and legal compliance of the organization.

In one example, the processor 103 is configured to determine that the patient identification data is sufficient where the patient identification data includes values for the data items specified by the criterion 109. In this example, the processor 103 is also configured to determine that the patient identification data is insufficient where the patient identification data does not include values for the data items specified by the criterion 109. In some examples, the processor 103 is configured to take further actions where the patient identification data is sufficient to uniquely identify the patient. These actions can include storage and utilization of the patient reference code (e.g., the patient reference code 111) supplied by the exchange system 165. The actions can also include execution of the query service 113. In various implementations, the processor 103 may provide the patient reference code to the user interface device 106 and optionally to one or more of the exchange system 165 (e.g., within a patient record query 190) and the medical device(s) 132. The actions can also include transmission of the identified or newly generated patient reference code to a user interface device 106 that is associated with the dispatched care provider 112. This association can be established, for example, via authentication of the care provider 112 via the device 106. The transmission of the patient reference code can occur while the care provider 112 is en route to the street address reported by the bystander, upon the care provider's 112 arrival at the street address, or thereafter. In these examples, the user interface device 106 is configured to receive the patient reference code and store the same in local memory.

In some examples, the query service 113 is configured to retrieve and locally store some or all of the medical record(s) 110 for the patient 114. In these examples, the query service 113 is configured to generate a query for the medical records of the patient and to transmit the query (e.g., the patient record query 190) to the exchange system 165. For instance, in some examples, the query service 113 can be configured to generate the query to the exchange system 165 in a format (e.g., Health Level Seven (HL7) or a proprietary format) supported by the exchange system 165 and that includes data items from the patient identification data required by the exchange system 165 (e.g., the patient reference code 111). The generated query can request some or all of the medical record for the patient 114 using at least a portion of the patient identification data. The query service 113 is also configured to transmit the query to the exchange system 165, receive and parse the response including a medical record (e.g., the patient medical record 192), and store the medical record in the memory 104 as the medical record 110 in association with the patient identification data. Alternatively or additionally, if the digest system 102 has subscribed to the exchange system 165 to receive patient medical records 192, the query service 113 is configured to receive and parse patient medical records 192 received via the subscription.

In some implementations, the user interface device 106 is configured to monitor the mobile environment 199 for information indicative of the medical event encountered by the patient 114. For instance, in some examples, the user interface device 106 is configured to detect activation of the medical device(s) 132 (e.g., via a local network connection) as such activation can indicate the care provider's 112 initial impression of the medical event encountered by the patient. For instance, where the user interface device 106 detects the presence of a defibrillator in the mobile environment 199, the user interface device can prompt the care provider 112 via the user interface 115 to confirm that the patient has suffered a cardiac arrhythmia. The care provider 112 can respond to the prompt to either confirm or deny that the care provider 112 had this initial impression.

The user interface device 106 can also be configured to transmit a medical data query 195 to the digest system 102.

In an implementation, the user interface device 106 may generate the medical data query 195 automatically in response to and based on data received at the device 106 (e.g., data captured from the user interface 115 and/or data received from the medical device(s) 132). Additionally or alternatively, the user interface device 106 may automatically generate the medical data query 195 in response to and based on data entered into or recorded by an electronic patient charting record (ePCR) 116 or other application on the user interface device 106. The data captured in the ePCR may include an emergency call type received from the CAD, a chief complaint or other observation by the care provider entered into the ePCR, and/or data captured by the ePCR 116 from the medical device(s) 132. In some examples, the user interface device 106 may automatically transmit the medical data query 195 in response to detecting a particular type of medical device in the mobile environment 199. Examples of these types of medical devices include defibrillators, portable ventilators, cardiac monitors, automatic chest compressors, and the like. The user interface device 106 may detect these medical devices based on information received from the medical devices, the initiation of a communicative coupling with the medical devices, and/or entry of information to the user interface device 106 by the care provider where the information includes the identification of a medical device type and/or data corresponding to a particular device type.

In an implementation, a user of the device 106 may enter or request a medical data query at the user interface 115. In an implementation, a user may originate the medical data query 195 at the user interface 115. For example, the user interface 115 may prompt the user to request the medical record digest 118. In an implementation, the user may include medical data indicators 135 with the request for the query and/or the patient reference code 111. The user may type or dictate a query in response to the prompt.

The medical data query 195 may include the patient reference code and may include one or more medical data indicators 135. The medical data indicators 135 may specify or suggest specific items of medical information and/or categories of medical information relevant to the patient's presentation and/or relevant to the nature of the emergency event. Examples of the one or more medical categories that can be specified by the medical data indicators include EMS call types, types of medical information, and items from a predetermined, configurable list. The EMS call types may correspond, for example, to patient presentations. The patient presentations can include, for example, cardiac arrest, trauma, sepsis, drug overdose, and lacerations. The EMS call types may include, for example, types of emergency incidents (e.g., as indicated in emergency call information received by the CAD system 130). The EMS call types may include, for example, types of prescheduled EMS transports. The types of medical information may include, for example, potential health threats to an EMS rescuer. The types of medical information may include, for example, existing patient conditions, patient allergies, patient medications, and/or patient physiologic information. The types of medical information may include, for example, transmittable diseases and chronic conditions. The types of medical information may include, for example, field names from an ePCR. The predetermined list may be specific to a particular EMS agency. The predetermined list may be statistically derived from cumulative records of an EMS agency.

Other categories of medical data can include location information (e.g., where such information may provide insight in the treatment of a patient). For instance, a chemical plant location could indicate that any history of respiratory disease may be helpful, as respiratory disease could be exacerbated by inhaling fumes. A playground location could indicate that any history of environmental allergies (bees, pollen) may be helpful. A methadone clinic location could indicate that any drug abuse indicators in a patient's past may be helpful. A ski slope location could indicate that any history of spinal or bone injuries may be helpful. A concert venue or sports arena could indicate that any history relevant to intoxication may be helpful. A bar, concert venue, or sports arena location could indicate that any history relevant to trauma due to assault may be helpful. A senior home/nursing facility location could indicate that any history of Alzheimer's or dementia may be helpful. A swimming pool or beach location could indicate that conditions relevant to drowning or shark bite may be helpful. As such, in some examples, the location information may serve a predictive capability (i.e., by providing information that is clinically relevant to likely injuries and issues based on location).

In some examples, the user interface device 106 is configured to prompt the care provider 112, via a user interface 115, to provide an initial impression of the medical condition of the patient 114. In this example, the user interface device 106 is further configured to generate and transmit a medical data query to the digest system 102 upon receipt of input specifying the initial impression. The medical data query can include, for example, a category of medical data and the patient reference code. For example, entry of the initial impression of cardiac distress into an ePCR may generate a medical data query that includes this initial impression. The resulting medical record digest 118 may include medical history clinically relevant to cardiac distress.

In certain examples, the user interface device 106 is configured to operate as an EMS patient charting device. In these examples, the user interface device 106 is configured to automatically generate and transmit a medical data query at power on or in response to receiving certain ePCR data that is configured to trigger generation and transmission of a medical data query. For instance, in one example, the ePCR data specifies one or more physiological signals. In this example, the user interface device may be configured to receive the one or more physiological signals from the medical device(s) 132.

Continuing with the example illustrated in FIG. 1, the digest system 102 is configured to receive the medical data query 195 and pass the medical data query to the processor 103 for handling. To handle the medical data query, the processor 103 is configured to parse the query to extract the patient reference code and the category of medical data specified in the query. The processor 103 is further configured to identify the medical record 110 via its association with the patient reference code 111 and retrieve the portions of the medical record that are related to the category of medical data specified in the query. The processor 103 is also configured to generate the medical record digest 118 to include the retrieved portions of the medical record 110, to associate the medical record digest 118 with the patient reference code 111, and to transmit the medical record digest 118 to the user interface device 106. The user interface device 106 is configured to receive the medical record digest 118, to parse it to extract the portions of the medical record 110 stored therein and to present the portions to the care provider 112 via the user interface 115.

In an implementation, the medical record digest system 102 may be communicatively coupled to the one or more medical device(s) 132 and may generate the medical record digest without a medical data query from the user interface device 106. For example, the processor 103 may receive, from the medical devices 132, one or more physiological signal(s) from the patient 114 in real time. The processor 103 may generate the medical record digest 118 based on the physiological signals and the possible medical conditions indicated by these signals. For example, an electrocardiogram (ECG) may indicate ventricular fibrillation and the generated medical record digest 118 might be for health history information relevant to ventricular fibrillation (e.g., history of cardiac disease and/or medications and procedures related to cardiac disease). As another example, a pulse oximetry measurement may indicate respiratory distress (e.g., hypoxia) and the generated medical data query might be for health history information relevant to respiratory distress (e.g., history of smoking or asthma and/or medications and procedures related to respiratory conditions). In some examples, the medical record digest system 102 may generate the medical record digest 118 in response to detecting a particular type of medical device in the mobile environment 199. Examples of these types of medical devices include defibrillators, portable ventilators, cardiac monitors, automatic chest compressors, and the like.

In some examples, the processor 103 may generate the medical record digest 118 based on other factors, such as EMS call type and/or location of the patient. The digest system 102 may receive information indicating these other factors directly or via the medical data query 195. For example, the CAD system 130 may provide an EMS call type (e.g., based on the 911 call) to the digest system 102 via the exchange system 165 and/or to the user interface device 106. The user interface device 106 may automatically generate a medical data query that includes the EMS call type. Alternatively, the digest system 102 may receive the EMS call type from the exchange system 165 and generate the medical record digest 118 without the medical data query. For example, the call type may be drug overdose and the generated medical record digest might be for health history information relevant to drug abuse and/or medications and procedures related to drug abuse.

As another example, the medical record digest system 102 may receive an emergency location from the CAD system 130 via the exchange system 165. Alternatively, the user interface device 106 may receive the emergency location from the CAD system 130 and/or from a GPS location device coupled to or included in the user interface device 106. The user interface device 106 may include the emergency location information in the medical data query 195 (e.g., either automatically or in response to a user entered query that includes the emergency location information). The location information may provide insight into likely treatments, interventions, or patient conditions. For instance, a chemical plant location could indicate that any history of respiratory disease may be helpful, as respiratory disease could be exacerbated by inhaling fumes. A playground location could indicate that any history of environmental allergies (bees, pollen) may be helpful. A methadone clinic location could indicate that any drug abuse indicators in a patient's past may be helpful. A ski slope location could indicate that any history of spinal or bone injuries may be helpful. A concert venue or sports arena could indicate that any history relevant to intoxication may be helpful. A bar, concert venue, or sports arena location could indicate that any history relevant to trauma due to assault may be helpful. A senior home/nursing facility location could indicate that any history of Alzheimer's disease or dementia may be helpful. A swimming pool or beach location could indicate that conditions relevant to drowning or shark bite may be helpful. As such, in some examples, the location information may serve a predictive capability by enabling the digest system 102 to predict medical history information that is clinically relevant to likely injuries and issues based on location.

It should be noted that, in some examples, the user interface 115 can be a visual user interface, an audio user interface (e.g., includes a microphone and/or a speaker), and/or an augmented reality user interface. Further, while FIG. 1 illustrates the digest system 102 as a computing device distinct from the other illustrated computing devices, in at least one example, the digest system 102 is a part of the user interface device 106 and/or the medical device 132.

Figure 2A:
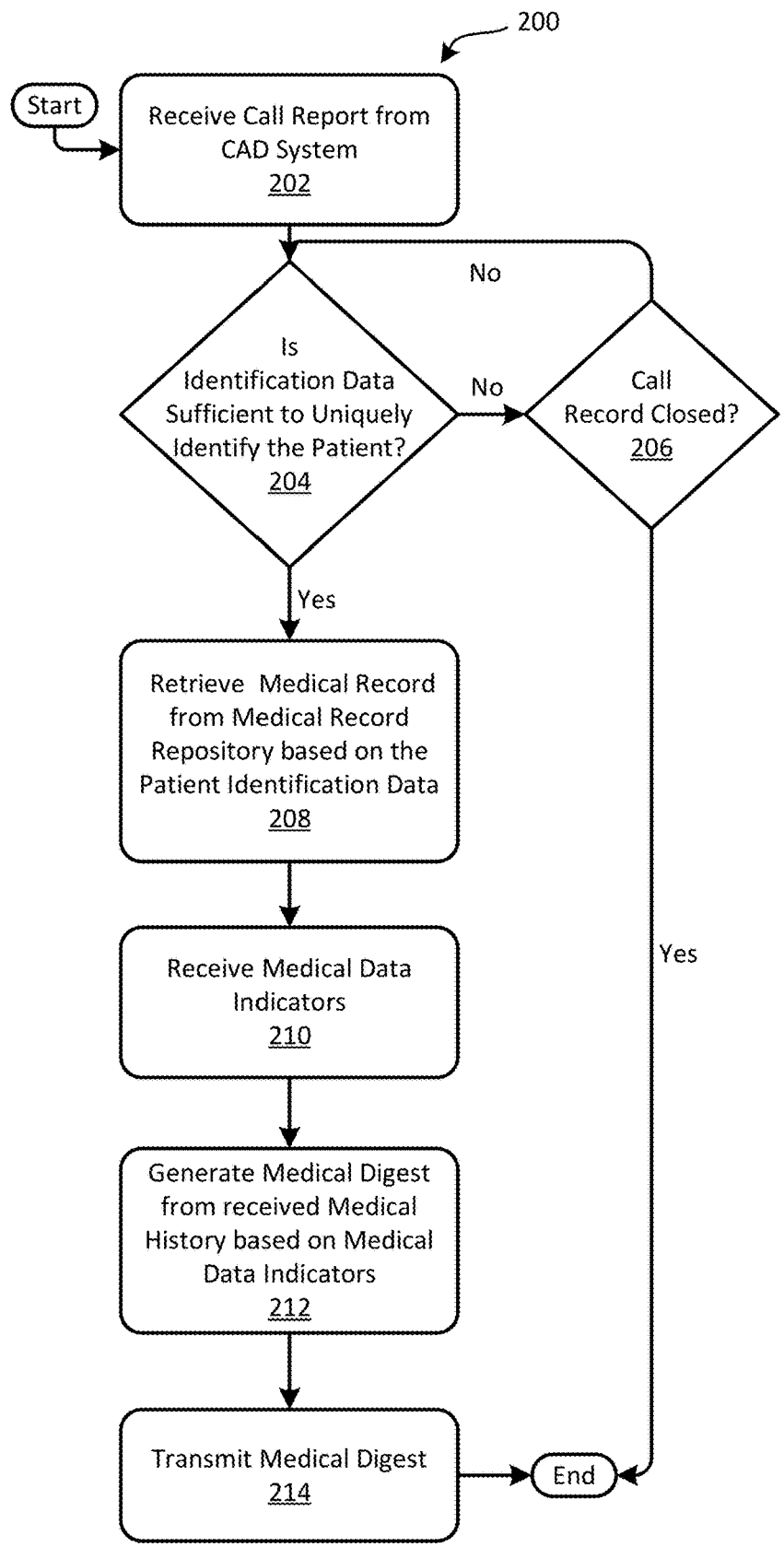
FIG. 2A is a flow diagram of a digest generation process in accordance with at least one example disclosed herein.

The system 100 can be configured to execute a variety of processes in various examples. For instance, in one implementation, the system 100 is configured to execute a digest generation process that generates a medical record digest 118 from the record 110. FIG. 2A illustrates one example of such a digest generation process, the digest generation process 200. It should be noted that, prior to execution of the digest generation process 200, the digest system 102 has successfully subscribed to receive patient medical records 192 from the exchange system 165.

As shown in FIG. 2A, the process 200 starts with an exchange system (e.g., the exchange system 165 of FIG. 1) receiving 202 a call record from a CAD system (e.g., the CAD system 130 of FIG. 1) indicating that a patient (e.g., the patient 114 of FIG. 1) has been involved in a reported call and is in need of medical assistance. This call record can specify a call type and patient identification data. Depending on the completeness of the patient identification data, the exchange system may be unable to identify the patient based solely on the patient identification data received in the call record. Moreover, even where the patient is identifiable, the completeness/confidence score of the patient identification data may be insufficient to safely (or legally) conclude that the patient has been uniquely identified.

Thus the process 200 continues with the exchange system parsing the call record, allocating and populating an incident record with information from the call record, and determining 204 whether the patient identification data in the call record is sufficient to uniquely identify the patient. In some examples, the exchange system executes a patient identification process (e.g., via the patient identifier 167) based on the patient identification data included in the call record and records the results of the patient identification process in the incident record. In some examples, the patient identification process executed by the patient identifier is the patient identification process 300 illustrated in FIG. 2B.

Figure 2B:
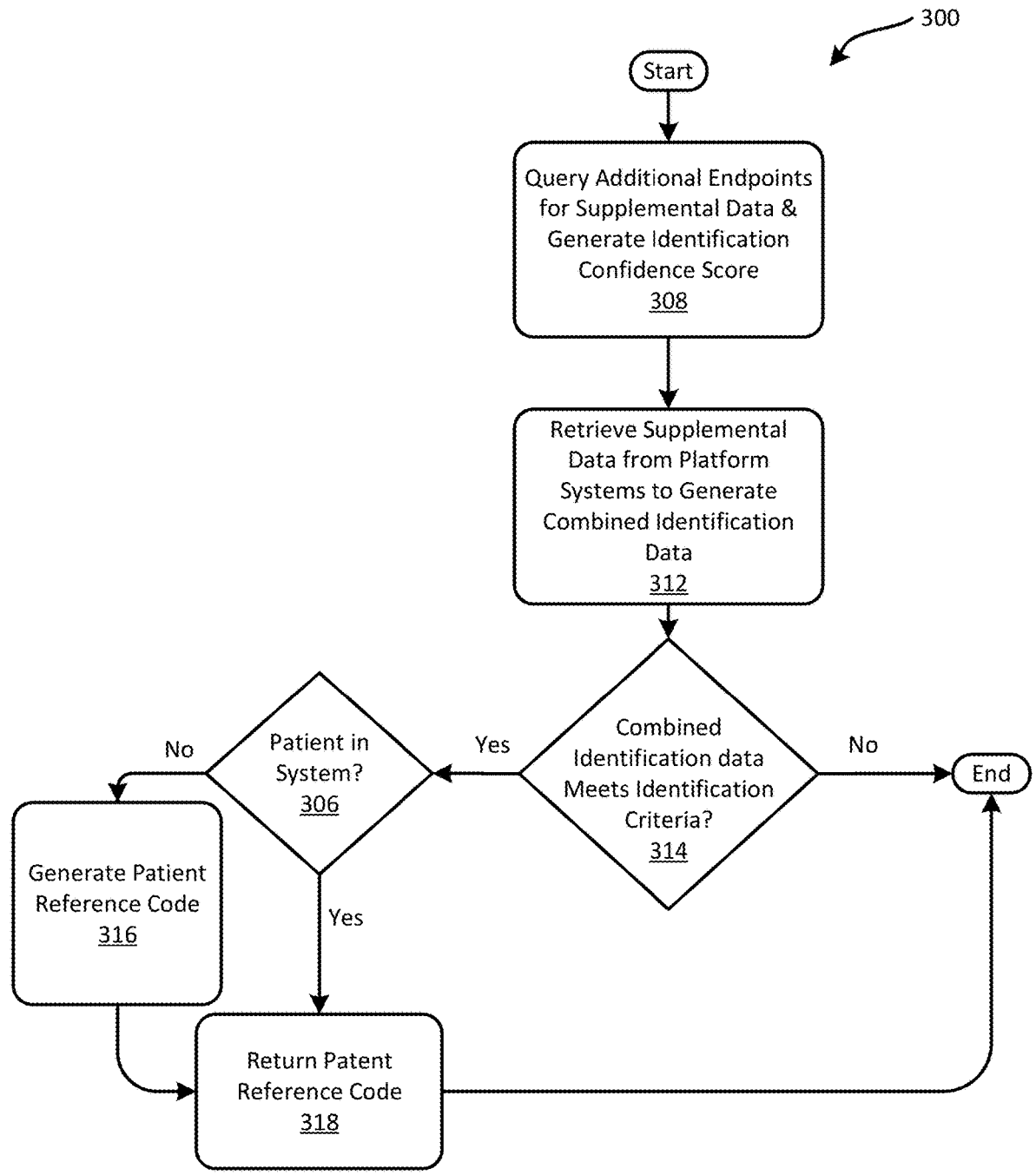
FIG. 2B is a flow diagram of a patient identification process executed by a medical record digest system in accordance with at least one example disclosed herein.
Figure 3A:
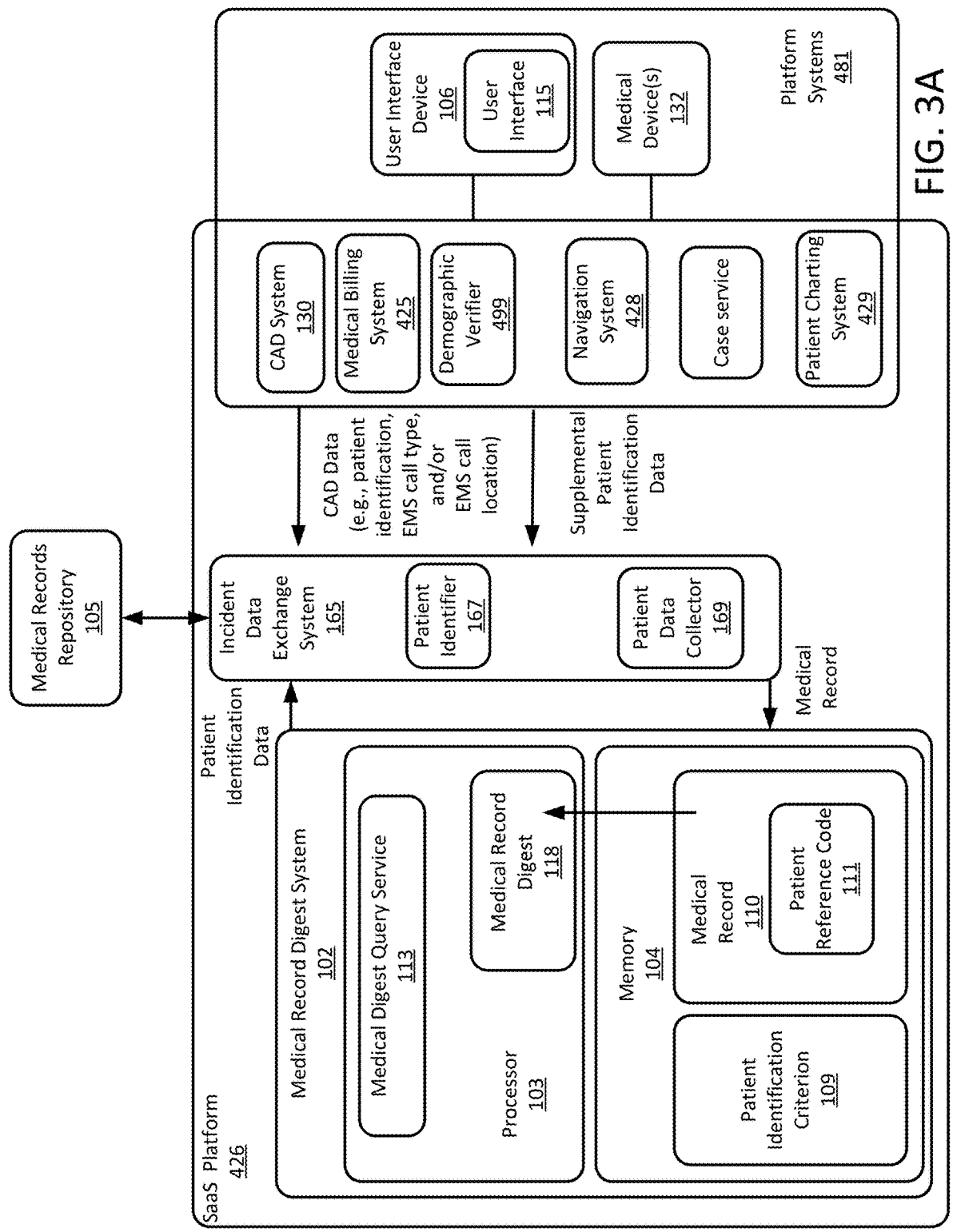
FIG. 3A is a schematic block diagram of a medical record digest system interoperating with an incident data exchange system in accordance with at least one example disclosed herein.
Figure 3B:
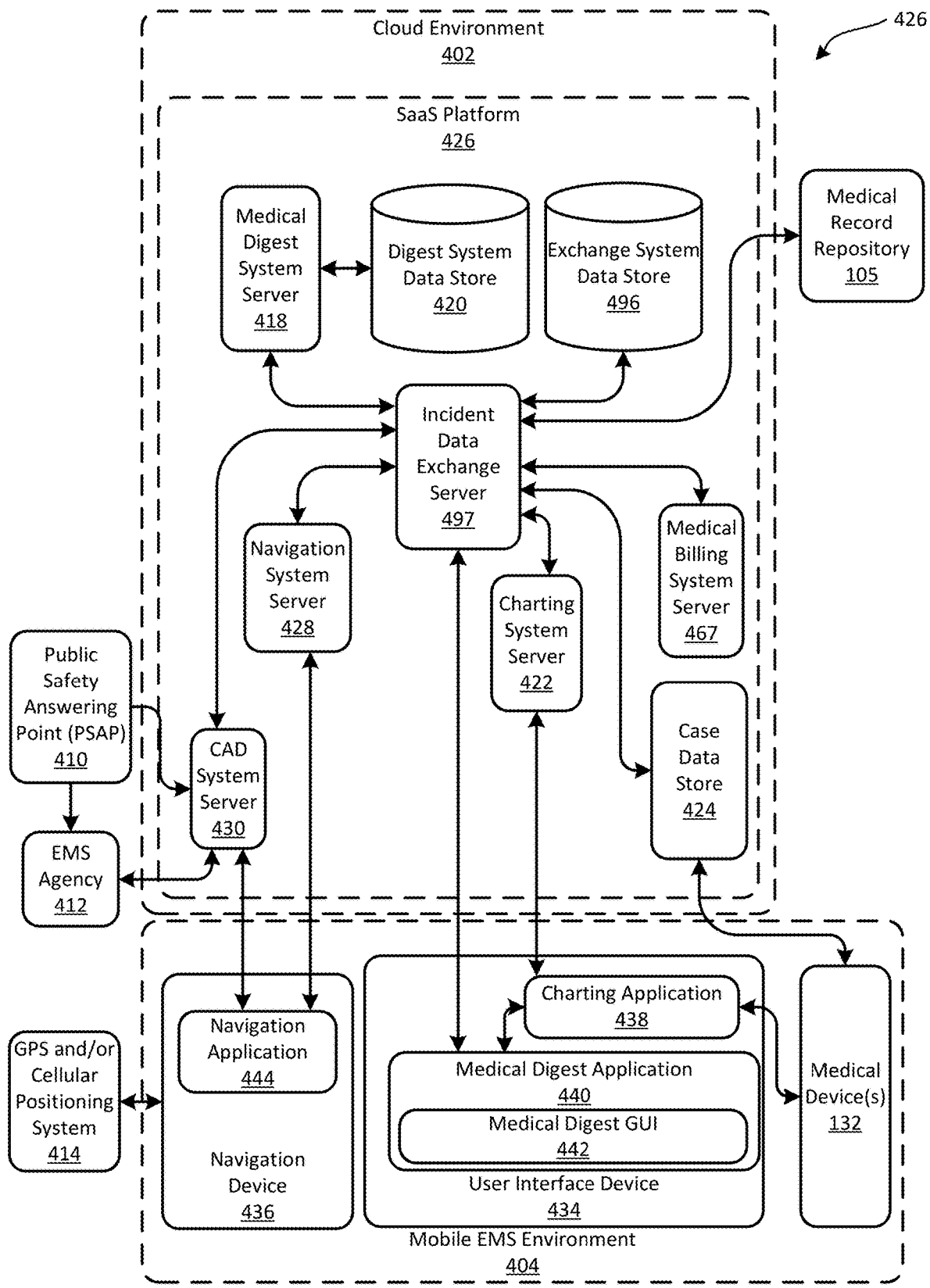
FIG. 3B is a schematic block diagram illustrating the logical and physical architecture of a medical record digest system, and other supporting systems, in accordance with at least one example disclosed herein.

As shown in FIG. 2B, the process 300 starts with a processor of the exchange system attempting to supplement the patient identification data provided to the processor by determining 308 whether other system endpoints in data communication with the exchange system have access to supplemental identification data that can be used to supplement the patient identification data. For instance, in some examples, in the operation 308 the processor generates and transmits request messages (queries) for supplemental identification data to the other system endpoints and receives responses thereto. Examples of these other system endpoints include the CAD system 130, a navigation system 428 that interoperates with the CAD system, a patient charting system 429, medical devices 132, a user interface device 106, a database system storing medical records generated by the medical devices, a demographic verifier 499, and/or a medical billing system 425. FIGS. 3A and 3B, which are described below, illustrate some of these other system endpoints.

In an implementation, the endpoints connected to and registered with the exchange system may include a demographic verifier 499. The demographic verifier 499 may utilize initial demographic data specified to the processor (e.g., by the CAD system) to search (e.g., via keywords using binary or fuzzy logic) for additional demographic data and/or to flag inconsistent and/or erroneous demographic data. The demographic verifier 499 may use the initial demographic data to access (e.g., via cross-referencing and/or linking) data from a data universe built from databases having historical patient information such as, for example, insurance coverage, insurance claims, credit records (including medical credit reports), liability insurance information, patient financial history information, employment records, etc. It should be noted that, in some implementations, the demographic verifier is a part of the medical billing system 425.

Based on this accessed data from the data universe, the demographic verifier 499 may associate additional demographic data with the initial demographic data. For example, if the initial demographic data includes a first name, a last name, and an address, the demographic verifier 499 may find a social security number, a date of birth and/or a middle name within the databases for the same first name, last name and address. The demographic verifier 499 may return this supplemental identification data to the processor of the exchange system. Alternatively or additionally, the demographic verifier 499 may provide this additional data to the medical digest system 102 and the medical record digest system 102 may use the initial data and the additional data in a medical records query (e.g., the query 190). As another example, the initial demographic data may include a first name and a last name, a date of birth, and a driver's license number. The billing system may find the first name, the last name, and the driver's license number used in one or more data sources with a different date of birth. In this case, the demographic verifier 499 may provide the exchange system with the different date of birth and flag the original date of birth as a likely error. Alternatively, the demographic verifier 499 may find the original date of birth and the different date of birth both used within the databases. In this case, the demographic verifier 499 may return both dates of birth and a confidence score for each date to the exchange system. Overall, the demographic verifier 499 may associate a confidence score with one or more items of original demographic data and/or one or more items of supplemental data. In some examples, the exchange system may pass these confidence scores to the digest system 102, and the digest system 102 may structure the patient records query 190 to utilize demographic data with a confidence score above a pre-determined threshold. The digest system 102 may provide multiple queries using demographic data with various confidence scores. In an implementation, the demographic verifier 499 may flag demographic data below a pre-determined confidence score as erroneous and the medical record digest system 102 may exclude such demographic data from the patient records query 190.

In some examples, the demographic verifier 499 derives insights from the data accessed from the data universe, for example using machine learning analysis and or other statistic data analysis techniques. The demographic verifier 499, for example, may include machine learning classifiers trained using historic data records to identify patterns in the data records of the data universe based upon initial patient identification data supplied to the process 300 (e.g., by the process 200). In another example, the demographic verifier 499 may derive insights from the data universe through cluster analysis of data records by applying techniques such as, in some examples, centroid-based clustering, density-based clustering, and/or multi-dimensional clustering. The information accessed from the data universe may be arranged in a variety of manners to apply the machine learning analysis and/or cluster analysis such as, in some examples, a convolutional neural network (CNN), deep neural network (DNN), clustering tree, and/or synaptic learning network. The arrangement of data and/or type of learning analysis applied may be based in part upon the type and depth of information accessed, the desired insights to draw from the data, storage limitations, and/or underlying hardware functionality of the demographic verifier 499.

In some examples, the confidence score generated by the demographic verifier 499 represents a degree of certainty that the patient in front of the care provider is the person represented by the demographic data. The confidence score may be calculated using any of a variety of techniques. The demographic verifier 499 may determine the confidence score for the entire set of demographic data and/or for each demographic item. The confidence score for the entire set of demographic data may be an aggregate score based on individual items of demographic data. For instance, in certain examples, the confidence score may be based on the number of occurrences of the item within the overall set of demographic data. Using a driver's license number as an example demographic item, where the demographic verifier 499 finds a driver's license number of DL1234 in two records associated with a combination of a patient's first name, last name, and date of birth and finds a driver's license number of DL1235 in five records associated with the same combination of first name, last name, and date of birth, the demographic verifier 499 scores DL1235 higher than DL1234. Alternatively or additionally, in some examples, the demographic verifier 499 determines the confidence score based on the source system of record for the demographic item. Continuing with the driver's license number example from above, where the demographic verifier 499 finds a driver's license number of DL1234 in a department of motor vehicles database and/or a liability insurance database and a driver's license number of DL1235 in a medical insurance company database, the demographic verifier 499 scores DL1234 higher than DL1235. Alternatively or additionally, in some examples, the demographic verifier 499 determines the confidence score based on combinations of data. Continuing with the driver's license number example from above, where the demographic verifier 499 finds a driver's license number of DL1234 associated with a patient's first name, last name, social security number, and date of birth and finds a driver's license number of DL1235 associated with only the patient's first name and last name, the demographic verifier 499 scores DL1234 higher than DL1235.

It should be noted that, as illustrated above, in calculating a confidence score, the demographic verifier 499 can communicate with a variety of systems and devices, such as those illustrated in FIGS. 3A and 3B, among others. In addition, the demographic verifier 499 can calculate a confidence score via a variety of processes, such as those described above, alone or in combination. As such, the demographic verifier 499 may identify discrepancies in demographic data provided by the patient and/or provided by one or more systems of record, calculate weights for these discrepancies, and combine the discrepancies and weights, if any, across multiple items of demographic data to arrive at a numerical representation of the degree of certainty that the patient is the individual represented and identified by the demographic data. In an implementation, the demographic verifier 499 may receive all or a portion of its input through an API accessed by and/or batch files provided by the source of the input data (e.g., any of the systems/servers illustrated in FIGS. 3A and 3B, among others).

In some implementations, a medical financial analysis tool may be part of and/or associated with the medical billing system 425 and hosted by the billing server 467 in some implementations. A medical financial analysis tool or system may aggregate and analyze data maintained by a wide range of distributed data sources to predict an estimate of medical claims payments. These distributed data sources include, but are not limited to, medical providers, billing companies, medical provider administration platforms, medical and liability insurance companies, credit and banking institutions, and employment databases and may add to the data universe of information described above. Historic trends and patterns within the data available from the data universe for a plurality of patients, payers, and providers enables prediction and estimation of future medical claims payments by the medical financial analysis tool. Thus, the medical financial analysis tool functions as a predictive analytics platform for medical claims and billing systems. The distributed data sources include one or more of medical insurance information of the patient, liability insurance information of the patient, a healthcare provider information of the patient, patient financial history information, patient credit information, one or more billing codes from previous EMS encounters with the patient, supplemental demographic data for the patient, confidence scores associated with initial and/or supplemental demographic data for the patient, or indications of erroneous demographic data for the patient.

The medical financial analysis tool and/or the medical billing system 425 may utilize demographic discovery or demographic verification to locate supplemental patient identification information. The medical financial analysis tool may access and leverage the distributed data sources of the data universe to enable demographic discovery. "Discovery" refers to a process of finding and identifying information relevant to patient demographic information that may be unknown and/or unavailable to the medical record acquisition system prior to the discovery process or information of which the medical record acquisition system was unaware of prior to the discovery process. The demographic discovery may also find likely errors in the patient identification information provided to the medical record acquisition system and may identify corrections to these errors.

Figure 3C:
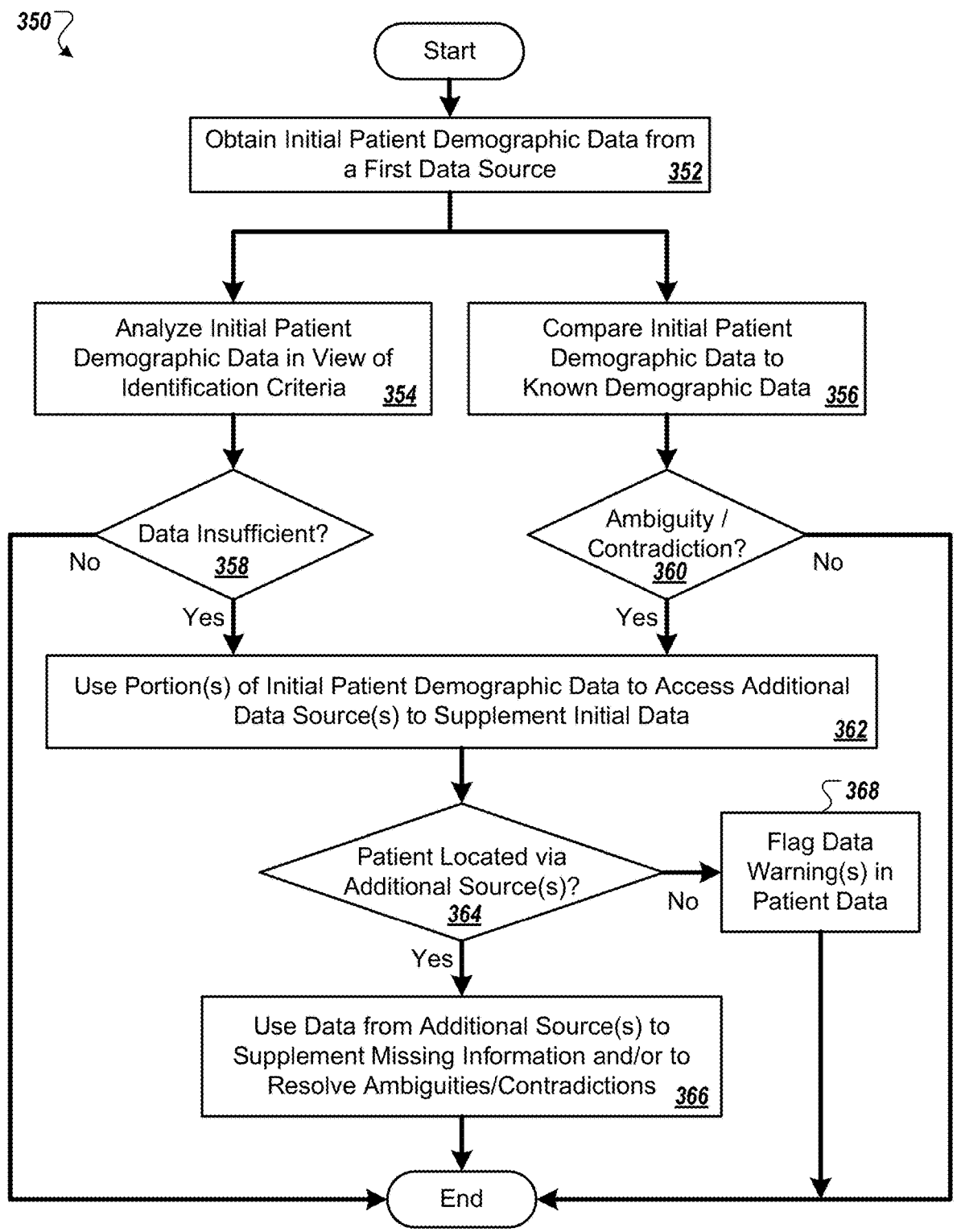
FIG. 3C is a flow diagram of process for correcting and/or updating patient demographic data in accordance with some examples.

FIG. 3C illustrates a method 350 for correcting and/or updating patient demographic data provided to, and executed by, a demographic verifier (e.g., the demographic verifier 499 of FIG. 3A) in some examples.

Turning to FIG. 3C, in some implementations, initial patient demographic data is obtained 352 from a first data source. The initial patient demographic data may be obtained, for example, as part of an initial patient assessment or an electronic medical chart. During a typical office visit, medical personnel may have the opportunity to obtain a full set of demographic information from a patient and compare that information to patient information on record to determine whether the patient is already entered in the system. However, in the circumstance of an emergency, few details may be known regarding the patient. For example, for a patient experiencing shock or other trauma, few details may be gleaned from the patient. Further, the information provided may have been misunderstood or misspelled by an EMS care provider (e.g., the EMS care provider 112 of FIG. 1).

In some implementations, the initial patient demographic data is analyzed 354 in view of identification criteria to determine whether the initial patient demographic data is sufficient for uniquely identifying the patient. The initial patient demographic data may include at least a portion of basic demographic information such as, in some examples, first and last name, at least a portion of an address, birth date, phone number, and gender. The criteria, for example, may involve a set of rules, each rule corresponding to one or more demographic fields that, alone or in combination, may be sufficient for uniquely identifying a patient. For example, social security number alone is a uniquely identifying data element, but first and last name alone are rarely a unique combination. In the circumstance of fairly common names, a name plus a birth date may also be insufficient. However, a name, birth date, and zip code may be deemed sufficient information for uniquely identifying the patient.

In some implementations, the initial patient demographic data is compared 356 to known patient demographic data. For example, the initial patient demographic data may be compared to one or more local records, to determine if there are any inconsistencies or ambiguities between the information. For example, the provided information may differ in one or more elements from the stored patient information, such as, in some examples, current address, spelling of the first name, spelling of the last name, and/or date of birth. The demographic verifier, for example, may apply fuzzy logic to identify close to but unmatched spellings in certain fields of demographic data (e.g., patient name, street name, city name, etc.).

In some implementations, if the initial patient demographic data is deemed 358 insufficient and/or there are ambiguities/contradictions 360 in the initial patient demographic data, one or more portions of the initial patient demographic data are used to access 362 at least one additional data source to supplement the initial patient demographic data. The additional data source(s), for example, may include the payer of the patient's primary coverage, a credit reporting agency, and/or a financial institution.

In some implementations, if the patient is located 364 via additional sources the data from the additional source(s) is used to supplement 366 the missing information and/or to resolve any ambiguities and/or contradictions within the initial patient demographic data. For example, the demographic verifier may update the patient data to reflect the information retrieved from the additional data source(s). The data may replace the initial patient demographic data. In other examples, the newly identified data may be added to the patient data record such that the initial patient demographic data is retained (e.g., for purposes for matching with additional information coming from the electronic patient chart which has not been updated, etc.).

If, instead, the patient is not located 364 via additional source(s), in some implementations, data warning(s) are flagged 368 in the initial patient demographic data.

Although described as a particular series of operations, in some examples, more or fewer steps may be included in the method 350. For example, rather than automatically supplementing 366 the missing information, the method 350 may first present the additional demographic data to a representative of the medical provider to receive manual confirmation prior to updating the patient data. In further examples, certain steps of the method 350 may be performed in a different order or in parallel. For example, in other examples, it is determined whether sufficient data is available 354 prior to comparing 356 for ambiguities and/or contradictions so that the comparison 356 can compare information from the additional data sources as well. Other modifications of the method 350 are possible.

Continuing with the process 300, where the responses received within the operation 308 include supplemental identification data, the processor parses the responses to retrieve the supplemental identification data and generates 312 combined identification data from the patient identification data received from the requesting process (e.g., the process 200) and the supplemental identification data received from the other system endpoints. For instance, in one example, the patient identification data includes the patient's first name, middle name, last name, and date of birth but omits the patient's social security number. Further, in this example, the supplemental identification data (e.g., retrieved from a medical billing system) includes the patient's social security number, primary care doctor, and insurance policy but omits the patient's middle name. Here, the combined identification data includes the first name, middle name, last name, date of birth, and social security number of the patient.

Continuing with the process 300, the processor determines 314 whether the combined identification data meets at least one sufficiency criterion. In some examples, the processor can search the combined patient identification data for populated data items specified by the at least one sufficiency criterion. In these examples, the processor determines that the combined patient identification data meets the at least one sufficiency criterion if the combined patient identification data includes the populated data items specified by the at least one sufficiency criterion. Conversely, in these examples, the processor determines that the combined patient identification data does not meet the at least one sufficiency criterion if the combined patient identification data does not include the populated data items specified by the at least one sufficiency criterion.

The at least one sufficiency criterion may be a default criterion or may be a criterion specified in subscriptions for patient medical records (e.g., the identification sufficiency criterion 109 of FIG. 1). Thus, in some examples, the processor determines 314 whether the combined patient identification data is sufficient to uniquely identify the patient for purposes of creating a medical record digest. For instance, in some examples, if the confidence score is high (e.g., 97% or higher) and/or at least one sufficiency criterion (e.g., the at least one sufficiency criterion 109 of FIG. 1) is otherwise met, the processor determines that the combined patient identification data is sufficient to uniquely identify the patient. In some examples, if the confidence score is low (e.g., less than 75%) and/or the at least one sufficiency criterion is not otherwise met, the processor determines that the combined patient identification data is not sufficient to uniquely identify the patient. Where the combined identification data meets the at least one sufficiency criterion, the processor proceeds to the operation 306 described above, and the process 300 continues. Where the combined identification data does not meet the at least one sufficiency criterion, the processor returns the combined patient identification data and the confidence score to the requesting process, and the process 300 ends.

Continuing with the process 300, the processor determines 306 whether the patient has been previously analyzed by the system. In some implementations, to determine 306 whether the patient has been previously analyzed by the system, the processor accesses a data structure (e.g., a patient master data store 260 of FIG. 2C) that associates stored identification data with previously generated patient reference codes. The stored identification data can include, for instance, patient identification data previously received from the CAD system and/or combined identification data previously received from a combination of sources. The patient reference codes can include, for example, the patient reference code 111 of FIG. 1. In these implementations, the processor determines 306 that the patient has been previously analyzed by the system where one association (e.g., row/record) in the data structure has stored identification data that matches (e.g., has the same items and values as) the patient identification data received in operation 202 above or the combined identification data generated by operation 312, which is described below. Further, in these implementations, the processor determines 306 that the patient has not been previously analyzed by the system where no association in the data structure has stored identification data that matches the patient identification data or the combined identification data.

Continuing with the process 300, where the processor determines 306 that the patient has been previously analyzed by the system, the processor proceeds to return 318, to the process 200, the combined patient identification data (including the patient reference code associated with the matched stored identification data and the confidence score), and the process 300 ends. Where the processor determines 306 that the patient has not been previously analyzed by the system, the processor generates 316 a patient reference code as described above with reference to FIG. 1. Upon generating 316 the patient reference code, the processor proceeds to return 318, to the process 200, the combined patient identification data (including the patient reference code associated with the matched stored identification data and the confidence score), and the process 300 ends.

Processes in accord with the process 300 enable an incident data exchange system to ensure that a patient is properly identified in the system prior to publishing information regarding the patient to registered and subscribed endpoints.

Returning to the process 200, if the processor determines 204 that the available patient identification data is insufficient to uniquely identify the patient, the processor proceeds to operation 206. Otherwise, if the processor determines 204 that the available patient identification data is sufficient to uniquely identify the patient, the processor proceeds to operation 208.

Continuing with the process 200, where the processor determines that the patient identification data was insufficient to uniquely identify the patient, the processor determines 206 whether it has received a notification from the CAD system indicating that the CAD system has closed the call record. Where the processor has received such a notification, the process 200 ends. Where the processor has not received such a notification, the processor returns to the operation 204 to determine whether available identification data is sufficient to uniquely identify the patient.

Continuing with the process 200, where the processor determines that the patient identification data was sufficient to uniquely identify the patient, the processor proceeds to retrieve 208 a medical record for the patient from a medical record repository (e.g., the medical record repository 105 of FIG. 1) and publishes the medical record to a processor of the digest system. The processor of the digest system, in turn, receives the medical record (e.g. via the query service 113 of FIG. 1) and parses the medical record. In some examples, within the operation 208 the processor of the digest system may add patient identification to the retrieved medical record where such information is omitted. This may occur, for example, when the source of the medical record has yet to be updated with recent information. For instance, in one example, the processor updates the medical record with recent treatment information (e.g., physiological parameters of the patient) included in supplemental identification data provided by a medical device 132.

In an implementation, the processor also organizes, sorts, and/or formats the medical record according to various categories of medical data within the operation 208. For example, the processor may convert the medical record to an indexed record. For instance, the processor may assign a plurality of tags to portions of the medical record. The process used to assign tags to portions of the record can vary between examples. For instance, in one example, the processor can identify a tag associated with one or more portions of the medical record by accessing a data structure that associates tags with types of data portions stored in medical records. In this example, the processor identifies the tag for each portion of a medical record by locating an association (e.g., a row/record) within the data structure in which a copy of the tag and a type identifier for the portion is stored. The processor then stores an entry in the indexed record for each portion under its associated tag. It should be noted that each portion of the medical record may be stored under multiple tags, depending on the implementation. In addition, other methods of associating tags to portions of medical records implemented in examples include utilizing a rule set (rather than simple association, as described above) and/or via machine learning processes. Subsequent to creating an indexed record, the processor stores the indexed record in memory (e.g., the memory 104 of FIG. 1).

Continuing with the process 200, the processor receives 210 one or more medical data indicators. In an implementation, the processor 103 may receive the medical data indicators 135 in a medical data query 195 from a user interface device (e.g., the user interface device 106 in FIG. 1). Additionally or alternatively, the processor 103 may receive the medical data indicators from a source other than the user interface device 106 (e.g., from the medical devices 132 or the CAD system 130). In an implementation, the medical devices 132 and/or the CAD system 130 may include the patient reference code 111 (e.g., as provided by the processor 103) with the medical data indicators. In this case, the user interface device 106 may not generate a medical data query. In an implementation, the processor 103 may receive the medical data indicators from the medical devices 132, the CAD system 130, and/or another platform entity communicatively coupled to the medical record digest system, as shown for example in FIG. 3B. For example, the processor 103 may receive physiological signals or other measurements from the medical device(s) 132. As another example, the processor 103 may recognize the types of medical device(s) 132 in the mobile environment based on a message transmission from the medical device(s) 132 to the digest system 102 exclusive of particular physiological data. For example, if the medical device type is a defibrillator, this may indicate a category of "cardiac" for the medical digest system. As another example, if the medical device type is a ventilator, this may indicate a category of "respiratory conditions" for the medical digest system. As a further example, if the medical device type is a drug delivery device, this may indicate a category of "blood conditions," "medical history," and/or "allergies." As a further example, the processor 103 may receive emergency type and/or location information from the CAD system 130. One or more of these communications with the medical record digest system 102 may indicate the medical status of the patient at a given point in time. In other words, these communications provide or indicate the medical data indicators.

Continuing with the process 200, the processor generates 212 a medical digest (e.g., the medical digest 118 of FIG. 1). For example, the processor can retrieve data from the medical record that is associated with and/or otherwise clinically relevant (and therefore potentially actionable) to the medical data indicators. In some examples, portions of the medical record are indexed with one or more tags associated with one or more medical categories to facilitate easy retrieval by the processor. Further, the processor can store these portions of the medical record in the medical record digest. In addition, in some examples, the processor merges the patient identification data and/or the supplemental data into the medical record digest. For instance, in one example, the processor merges supplemental data from a medical billing system into the medical record digest.

In some examples, to generate clinically actionable medical record digests within the operation 212, the processor accesses the indexed record and retrieves portions thereof that correspond to the medical data indicators. For example, the retrieved portions may correspond to at least one medical category. Like the process of assigning tags to portions of the medical record, the process of determining portions of the medical record that are clinically actionable in a given situation for a particular patient vary between examples. For instance, in one example, the processor identifies one or more categories of medical data to be included in the medical record digest from the medical data indicators (e.g., one or more categories included in a medical data query and/or indications of patient medical status outside of the medical data query) and identifies tags of indexed records associated with the one or more categories (e.g., via a data structure that associates tags of indexed records with categories of medical data). Next, the processor retrieves portions of the medical record associated with the identified tags from the indexed record and generates a medical record digest using the retrieved portions. It should be noted that other methods of associating indexed medical data with medical data indicators are implemented in various examples. For instance, some examples utilize a rule set (rather than simple association, as described above) and/or via-machine learning processes. Processes of indexing medical records and generating medical record digests are further described below, for example, with reference to FIGS. 4A and 4B.

Using the indexing and generation processes described herein, the processor generates medical record digests clinically relevant and actionable to many situations. For instance, in some examples, the processor generates medical record digests with clinically actionable information for responders to EMS calls involving presentations such as cardiac arrest, trauma, sepsis, drug overdose, and lacerations. Further, in some examples, the processor 103 generates medical record digests with potentially clinically actionable information for types of emergency incidents, such as car wrecks, fires, shootings, and the like. In certain examples, the processor generates medical record digests with potentially clinically actionable information for EMS care providers involved with prescheduled EMS transports, such as transports of a critically ill persons from one care facility to another. In some implementations, the processor generates medical record digests with potentially clinically actionable information for EMS care providers based on medical information such as potential health threats to the EMS care provider (e.g., transmittable diseases), existing patient conditions (e.g., chronic conditions), patient allergies, and/or patient medications. Moreover, in some instances, the processor generates medical record digests with potentially clinically actionable information based on values stored in particular field names in an ePCR and/or based on entries stored in a predetermined list. These values may be specific to a particular EMS agency, thereby giving the EMS agency control over the information presented in a medical record digest. The predetermined list may be statistically derived from cumulative records of an EMS agency.

Continuing with the process 200, the processor transmits 214 the medical record digest 118 to the user interface device 106. For example, the processor can control a network interface to transmit a copy of the medical digest to the user interface device. Subsequent to the operation 214, the process 200 ends.

Processes in accord with the process 200 enable a medical record digest system to create medical digests with potentially clinically actionable information that is tailored to the patient and a medical event encountered by the patient.

Figure 2C:
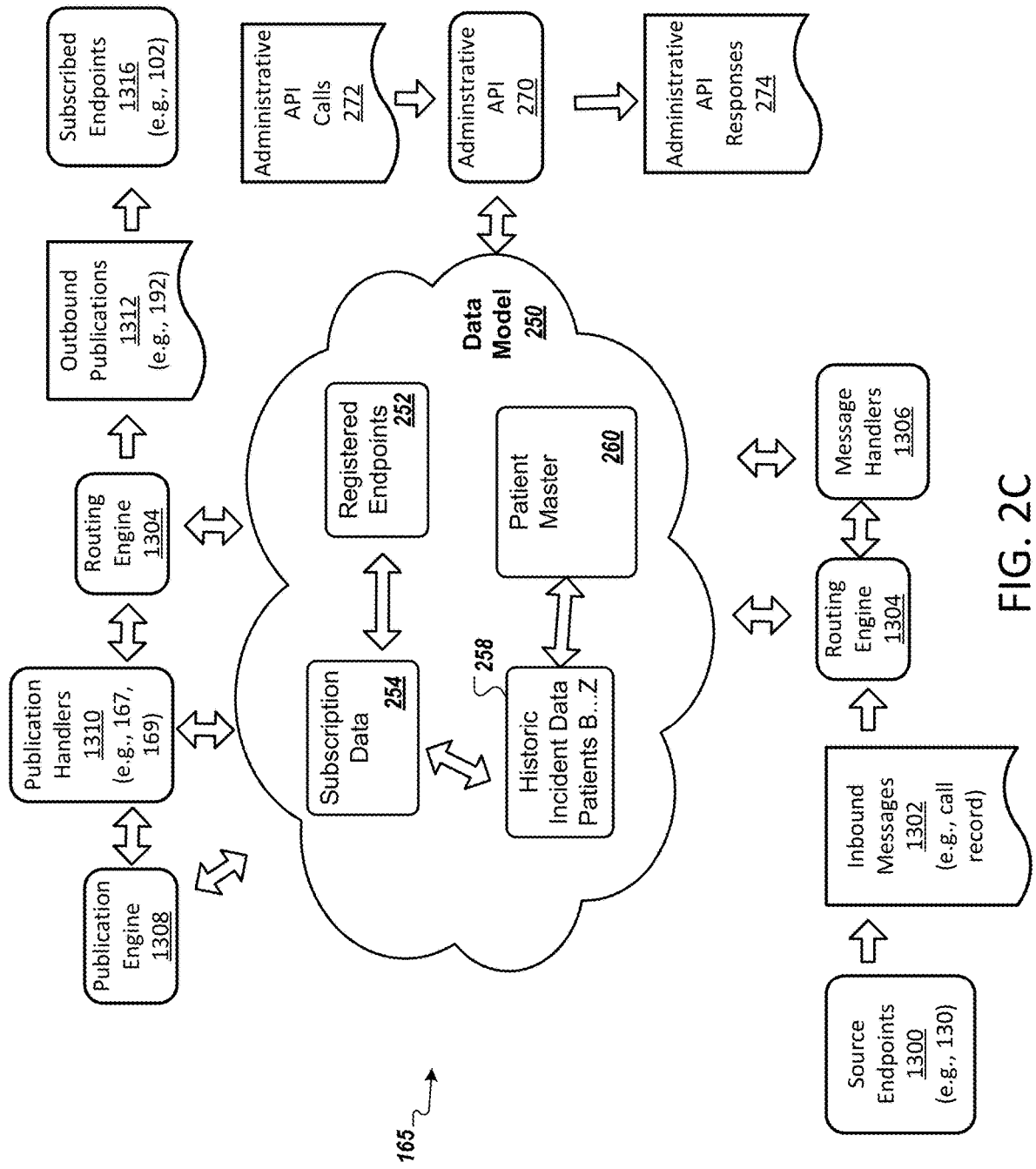
FIG. 2C is a schematic illustration of the exchange system 165 in some examples disclosed herein.

FIG. 2C is a schematic illustration of the exchange system 165 in some examples. As shown in FIG. 2C, the exchange system 165 includes an implemented data model 250, a routing engine 1304, message handlers 1306, a publication engine 1308, publication handlers 1310, and an administrative API 270. The implemented data model 250 includes a registered endpoints data store 252, a subscription data store 254, an historic incident data store 258, and a patient master data store 260, which stores patient identification data for patients involved in previously reported incidents. In some implementations, the patient master data store 260 also stores a cross-reference that associates patient reference codes with patient identifiers used to identify patients within endpoints. The implemented data model 250 may be stored, for example, in the exchange system data store 496 described below with reference to FIG. 3B. Also as shown in FIG. 2C, the administrative API 270 is configured to receive any of a variety of administrative API calls 272 and to process the administrative API calls 272 with reference to the implemented data model 250 to generate administrative API responses 274.

In an implementation, the administrative calls 272 that the administrative API 270 is configured to process include calls to register and deregister endpoints to participate within the exchange system 165. Examples of types of endpoints that can be registered within the exchange system 165 include CAD systems, medical records sources, medical billing systems, medical records repositories, medical digest systems, medical devices, and user interface devices with medical applications to name a few. Registered endpoints can report incidents involving patients and can subscribe to the exchange system 165 to receive publications. The subscriptions offered by the exchange system can limit publications as to the types of data published and to data descriptive of incidents within particular geographic or jurisdictional boundaries. Additionally or alternatively, subscriptions can be limited as to duration and can limit publications to particular update frequencies. One type of subscription offered by the exchange system 165 is a subscription to patient medical records (e.g., patient medical records 192 of FIG. 1). Attributes regarding a registered endpoint that can be communicated via the administrative calls 272 and stored in the registered endpoints data store 252 include one or more API endpoints (addresses) exposed by the registered endpoint, types of incident data offered by the registered endpoint, API calls/standards supported by the registered endpoint, and information identifying the registered endpoint (e.g., certificates or other information asserting authenticity of the endpoint). Responses 274 generated by the administrative API 270 to a registration-related administrative call 272 reflect success or failure of the requested API operation requested in the corresponding administrative API call 272.

It should be noted that, in some examples, the administrative API 270 is extensible in that the administrative API 270 allows for new types of endpoints to be defined and registered with the exchange system 165 via one or more administrative calls 272. For instance, where the manufacturer of a new type of medical device (e.g., a headband that monitors patient temperature, perspiration, and pallor) wishes to enable the medical device to share physiologic data via the exchange system 165, the manufacturers can utilize administrative calls 272 to create a new endpoint type (e.g., headband monitor) for the medical device that enables particular medical devices of the new type to register with the exchange system 165 as source endpoints. In certain implementations, the administrative calls 272 that the administrative API 270 is configured to process include calls to setup or withdraw endpoints from subscriptions. Attributes regarding subscriptions that can be communicated via these administrative calls 272 and stored in the subscription data store 254 include an identifier of the subscribing endpoint and an identifier of the subscription requested. Other subscription parameters that can be communicated and stored include, for example, a subscription termination date, maximum update frequency, geographic/jurisdictional boundaries, and an identification sufficiency criterion (e.g. the identification sufficiency criterion 109 of FIG. 1). Responses 274 generated by the administrative API 270 to a subscription related administrative call 272 reflect success or failure of the requested API operation requested in the corresponding administrative API call 272.

It should be noted that once an endpoint is subscribed to an identified subscription, the exchange system 165 publishes medical data to the subscribed endpoints in accordance with the limitations placed on the subscription by the publisher and the subscriber. It should also be noted that, some examples include a user interface that enables an administrative user to manually configure the exchange system 165 via the administrative API.

In some examples, the routing engine 1304 is configured to receive inbound messages 1302 from registered, source endpoints 1300 and to identify one or more message handlers 1306 to process the inbound messages 1302. In one example, a source endpoint 1300 is a CAD system (e.g., the CAD system 130 of FIG. 1). In this example, the inbound message 1302 received from the CAD system may be a call record. In response to receiving the call record, the routing engine identifies and authenticates the CAD system 130 as the source endpoint (e.g., via a registered endpoint identifier specified within the call record). Next, the routing engine 1304 accesses a cross-reference that associates endpoint identifiers with inbound message handlers 1306 that is stored within the registered endpoints data store 252. The routing engine 1304 identifies records within the cross-reference that include the endpoint identifier of the CAD system and one or more message handlers 1306 that are configured to process inbound messages from the CAD system. Next, the routing engine initiates the identified message handlers 1306 and passes the inbound message 1302 to the identified message handlers 1306 for processing.

In some examples, the message handlers 1306 parse the payload of the inbound message 1302 (e.g., a JSON object, DOM object, BLOB, etc.) and store the incident data specified therein in the incident data store 258. It should be noted that the incident data store 258 may be implemented as one or more data stores having a variety of data structures due to the different data types and relationships to be stored therein. For instance, in at least one example, the incident data store includes a cross-reference table that associates patient identification data (e.g., patient reference codes) with identifiers of registered endpoints that store medical data regarding the patients identified by the patient identification data.

In some examples, the publication engine 1308 loads subscription data from the subscription data store 254 and monitors the incident data store 258 for data manipulation specified as a publication trigger by a subscription specified within the loaded subscription data. For instance, if a digest system (e.g., the medical record digest system 102 of FIG. 1) is subscribed to the exchange system 165 to receive patient medical records (e.g., the patient medical records 192 of FIG. 1), the loaded subscription data may specify (e.g., within a cross-reference) that an incident record added via processing of an inbound message 1302 from a CAD system is a publication trigger for patient medical records. Thus, continuing the example from above, the publication engine 1308 detects a publication trigger associated with a subscription to patient medical records by the digest system in response to the message handler 1306 processing the inbound call record message.

In certain implementations, in response to detection of the publication trigger, the publication engine 1308 initiates one or more publication handlers associated with the publication trigger in the subscription data store 254. For instance, continuing the example from above, the publication engine 1308 identifies the patient identifier 167 and the medical data collector 169 of FIG. 1 within a cross-reference that associates these publication handlers 1310 with the publication trigger described above and, in turn, initiates the publication handlers 1310.

In some examples, the publication handlers 1310 generate publications based on data stored in the incident data store 258, the registered endpoints data store 252, and the subscription data store 254. The complexity of the publication handlers can execute logic that varies from simple string manipulation to more complex flow control, comparison operations, interoperation with other systems/endpoints, and other sorts of data manipulation. For instance, as explained above, the patient identifier 167 and the medical data collector 169 are configured to execute a highly specialized logic when generating publications such as patient medical records. Subsequent to generating publications, the publication handlers pass the generated publications to the routing engine 1304.

In some examples, the routing engine is further configured to receive publications, identify one or more endpoints 1316 subscribed to receive the publications, and generate outbound publications 1312 that are formatted for processing by the subscribed endpoints 1316. In these examples, the routing engine identifies the one or more endpoints via a cross-reference stored in the subscription data 254 that associates the one or more endpoints 1316 with the publication trigger. Next, the routing engine 1304 looks up the endpoints within the registered endpoints data store 252 to determine the address and formatting requirements of each. Finally, the routing engine 1304 formats the publications received from the publication handlers, formats the publications in accordance with a format supported by the subscribed endpoints 1316 to generate the outbound publications 1312, and communicates the outbound publications 1312 to the subscribed endpoints 1316.

Figure 2D:
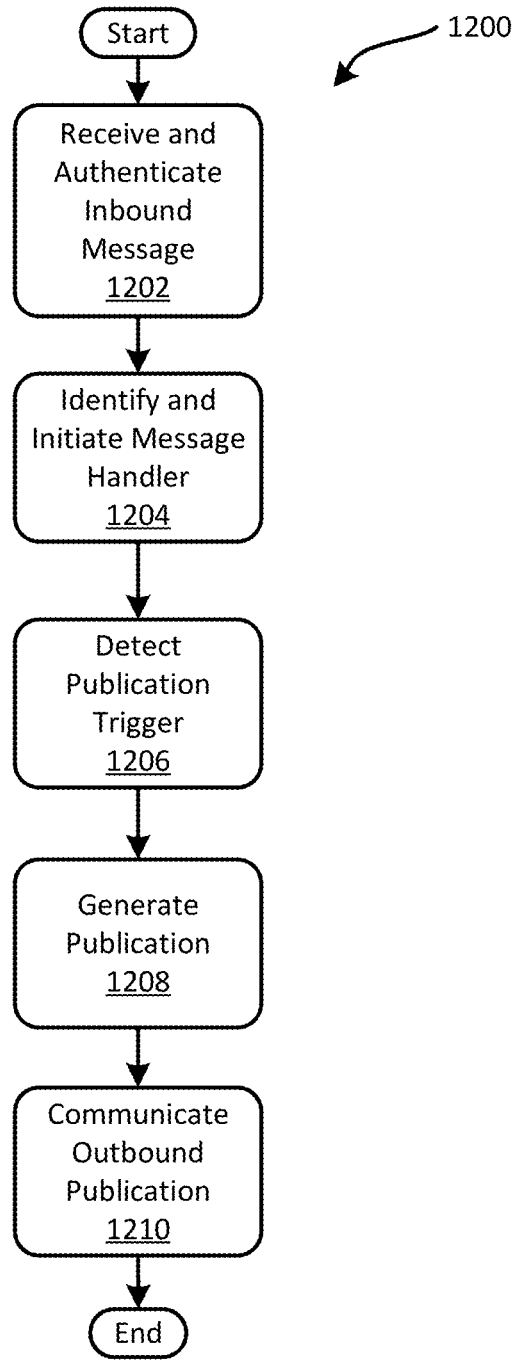
FIG. 2D is a flow diagram of a data gathering process executed by an exchange system in some examples.

FIG. 2D illustrates a process 1200 executed by the exchange system 165 in some examples. As shown in FIG. 2D, the process 1200 starts with a routing engine (e.g., the routing engine 1304 of FIG. 2C) receiving and authenticating 1202 an inbound message (e.g., the inbound message 1302 of FIG. 2C). For instance, the routing engine may receive the message and parse the message to extract an encrypted identifier of the source endpoint that originated the message. The routing engine may authenticate the message by decrypting the encrypted identifier using a symmetric key shared by the exchange system 165 and the registered endpoint and matching the decrypted identifier to an identifier of the registered endpoint stored in registered endpoint data store (e.g., the registered endpoint data store 252).

Continuing with the process 1200, the routing engine may identify and initiate 1204 one or more message handlers (e.g., the message handlers 1306 of FIG. 2C) to process the inbound message. For instance, in some examples, the routing engine identifies the message handlers in a cross-reference that associates registered endpoints with message handlers. This cross-reference may be stored in the registered endpoints data store.

Continuing with the process 1200, a publication engine (e.g. the publication engine 1308 of FIG. 2C) detects 1206 a publication trigger within an implemented data model of the exchange system (e.g., the implemented data model 250 of FIG. 2C). For instance, in some examples, the publication engine loads a set of publication triggers stored in a subscription data store (e.g., the subscription data store 254 of FIG. 2C). The publication triggers may specify that particular changes in the implemented data model indicate that a new publication of medical data is required. In one particular example, the addition of an incident record within an incident data store (e.g., the incident data store 258 of FIG. 2C) is specified as a publication trigger for patient medical records (e.g., the patient medical records 192 of FIG. 1) of a patient identified in the incident record. In response to the detection of a publication trigger, the publication engine initiates one or more publication handlers (e.g., the publication handlers 1310 of FIG. 2C) associated with the publication trigger within a cross-reference stored in the subscription data store.

Continuing with the process 1200, the one or more publication handlers generate 1208 one or more publications based on data stored in the incident data store 258, the registered endpoints data store 252, the subscription data store 254, and, potentially, stored outside the exchange system 165 (e.g., medical data store in an HIE or EHR, etc.). For instance, continuing the example from above, the one or more publication handlers for patient medical records can include the patient identifier 167 and the medical data collector 169 of FIG. 1).

Continuing with the process 1200, the routing engine creates and communicates 1210 outbound publications using data stored in the registered endpoints data store. For instance, in one example, the routing engine identifies supported formats and addresses of endpoints subscribed to the publications from a cross-reference stored in the registered endpoints data store that associates registered endpoint identifiers of the subscribed endpoints with data identified the supported formats and addresses. Next, the routing engine processes the publications to ensure they comport with the supported formats and to generate outbound publications. Finally, the routing engine communicates the outbound publications to the addresses, and the process 1200 ends. Continuing the example from above, the routing engine communicates patient medical records to the digest system.

FIG. 3A illustrates another platform 426 in which the incident data exchange system 165 assembles combined identification data to uniquely identify a patient (e.g., the patient 114 of FIG. 1). As illustrated in FIG. 3A, the platform 426 includes several features of the platform 100 illustrated in FIG. 1. These features include the digest system 102, the CAD system 130, the repository 105, the user interface device 106, and the medical device(s) 132. The exchange system 165 illustrated in FIG. 3A interoperates with the repository 105 and the CAD system 130 using the same techniques and interfaces as described with reference to FIG. 1. However, the platform 426, which is specially configured as a cloud-based software as a service (SaaS) platform, further includes a demographic verifier 499, a medical billing system 425, a navigation system 428, and an EMS patient charting system 429.

As shown in FIG. 3A, the billing system 425, the demographic verifier 499, the navigation system 428, the charting system 429, the interface device 106, and the medical device(s) 132 constitute a group 481 of platform systems as referred to above with reference to the operation 308 of FIG. 2B. As such, the exchange system 165 is configured to interoperate (e.g., per the operations 308 and 312 of FIG. 2B) with the platform systems in the group 481 to collect supplemental identification data where the patient identification data sourced from the CAD system 130 is insufficient to uniquely identify a patient and to identify or generate a patient reference code using the combination identification data. Further, in the example illustrated in FIG. 3A, the query service 113 generates a records query 190 for the medical record 192 using combined identification data for the patient.

The exchange system 165 can be configured to query for and receive different types of supplemental information, depending on the platform system that is the target of the query. For instance, in some examples, the exchange system 165 requests, and the billing system 425 supplies, supplemental identification data in the form of medical billing data including insurance information of the patient, healthcare provider information of the patient, and/or billing codes from previous EMS encounters with the patient. In some examples, the exchange system 165 requests, and the charting system 429 supplies, supplemental identification data in the form of patient medical data and/or patient demographic data. In some examples, the exchange system 165 requests, and the navigation system 428 supplies, supplemental identification data in the form of location data, such as the location of an emergency scene and/or the location of an EMS transport destination. In some examples, the exchange system 165 requests, and the medical device(s) 132 supplies, supplemental identification data in the form of patient medical information.

In some examples, the exchange system 165 requests, and the user interface device 106 supplies, confirmation of the patient identification data received from the CAD system 130. In this example, the user interface device 106 is configured to prompt a user (e.g., the care provider 112) via the user interface 115 to enter a confirmation of the patient identification data and to transmit a received confirmation to the exchange system 165. In this example, the exchange system 165 is configured to accept the patient identification data as sufficient in response to reception of the confirmation and to proceed accordingly. It should be noted that any of the information requested by the exchange system 165 may be requested by, and supplied to, the digest system 102 via the exchange system 165.

FIG. 3B illustrates a physical architecture of the SaaS platform 426 of FIG. 3A. As shown in FIG. 3B, the platform 426 includes a cloud environment 402 and a mobile EMS environment 404. The devices within these environments interoperate with a variety of external systems that include public safety answering points (PSAPs) 410, EMS agencies 412, and global positioning systems/cellular position systems 414. The cloud environment 402 hosts the platform 426. The platform 426 includes a CAD system server 430, a navigation system server 428, a patient charting system server 422, a medical billing system server 467, a case data store 424, a medical record digest system server 418, an incident data exchange server 497, a digest system data store 420, and an exchange system data store 496. The mobile EMS environment 404 includes a navigation device 436, a user interface device 434, and one or more medical device(s) 132. The navigation device 436 hosts a navigation application 444. The mobile EMS environment may also include an emergency vehicle, such as an ambulance, a fire engine, an EMS crew transport vehicle, and/or a helicopter. It should be noted that one or more organizations may own one or more of the devices illustrated in FIG. 3B.

In an implementation, the shared platform enables sharing of medical digest information between entities of the platform and enables various initiation points for the medical digest query. For example, initiation of a call by the CAD 430 and communication to the medical digest system 418 of the initiated call via the exchange server 497 may enable the medical digest system 418 to query and generate one or more medical digests and provide them to the charting system 422 and/or the billing system server 467. Alternatively, the CAD 430 may communicate with the charting system 422 and the charting system 422 may then communicate with the digest system 418 to query and generate the medical digest(s). The medical billing system server 467 may receive the digest information during or after the medical event via communications with one or more of the CAD, the charting system, or the digest system.

In some examples, the user interface device 434 hosts a medical digest application 440 and/or a charting application 438 (e.g., the ePCR 116). The medical digest application 440 includes a medical digest graphical user interface (GUI) 442. In some examples, the medical digest application 440 and/or the charting application 438 are configured to execute natively on the user interface device 434. In other examples, the medical digest application 440 and/or the charting application 438 are configured to execute within a browser and are served to the user interface device 434 by the digest server 418 and/or the charting server 422. In either case, the medical digest application 440 and/or the charting server 422 can include a control configured to render medical record digests. For instance, in one example, the control is configured to render medical record digests with a problems, allergies, and medication structure. The control can also be configured to render medical record digests chronologically. The control can also be configured to render medical record digests according to a relative severity of clinical impact.

In some examples, the digest application 440 is configured to interoperate with the charting application to communicate portions of medical record digests received by the digest application 440 to the charting application 438. In these examples, the charting application 438 can, for example, update or start an ePCR specific to a patient encounter. In an implementation, the charting application 438 includes an ePCR user interface configured to interact with a user to receive patient medical information, such as charting information. The charting application 438 can upload this information in the form of ePCRs to the charting server 422.

As shown in FIG. 3B, the cloud environment 402 may be implemented within a data center or other high capacity computing facility with high speed internet connectivity. The platform 426 may include a plurality of dedicated servers (e.g., a farm or cluster of computer systems) within the data center that are interconnected via a high speed, private network. Each of the servers illustrated within the platform 426 may be one or more physical and/or one or more virtual servers. The servers can include one or more application servers, web servers, and/or data base servers. The servers can include enterprise servers configured to support an organization as a single tenant and/or cloud servers configured to support multiple organizations as multiple tenants.

It should be noted that the software applications hosted by servers within the platform 426 are configured to expose application programming interfaces (APIs) that enable the software applications to communicate with one another. These APIs are configured to receive, process, and respond to commands issued by software applications hosted on the same server or a different server in the platform. For instance, these APIs enable any of the servers in the platform 426 to transmit a medical data query to the digest server 418 and to receive a response thereto. Similarly the APIs enable the digest server 418 to transmit patient reference codes to the other servers in the platform 426.

The APIs may be implemented using a variety of interoperability standards and architectural styles. For instance, in one example, the APIs are web services interfaces implemented using a representational state transfer (REST) architectural style. In this example, the APIs communicate with a client process using Hypertext Transfer Protocol (HTTP) along with JavaScript Object Notation and/or extensible markup language. In some examples, portions of the HTTP communications can be encrypted to increase security. Alternatively or additionally, in some examples, the APIs are implemented as a .NET web API that responds to HTTP posts to particular uniform resource locators. Alternatively or additionally, in some examples, the APIs are implemented using simple file transfer protocol commands and/or a proprietary application protocol accessible via a transmission control protocol socket. Thus, the APIs described herein are not limited to a particular implementation.

The network within the cloud environment 402 and the local network with the mobile EMS environment 404 can include one or more communication networks through which the computing devices within these environments send, receive, and/or exchange data. In various implementations, the network can include a cellular communication network and/or a computer network. In some examples, the network includes and supports wireless network and/or wired connections. For instance, in these examples, the network may support one or more networking standards such as GSM, CMDA, USB, BLUETOOTH®, CAN, ZigBee®, Wireless Ethernet, Ethernet, and TCP/IP, among others. The network may include both private networks, such as local area networks, and public networks, such as the Internet. It should be noted that, in some examples, the network may include one or more intermediate devices involved in the routing of packets from one endpoint to another. However, in other examples, the network can involve only two endpoints that each have a network connection directly with the other.

Continuing with FIG. 3B, the digest server 418 and data store 420 implement the digest system 102 of FIG. 1. The data store 420 can be implemented by, for example, a database (e.g., a relational database) and stored on a non-transitory storage medium. The data store 420 is configured to store medical records (e.g., the medical record 110 of FIG. 1) in association with patient reference codes (e.g., the patient reference code 111 of FIG. 1). The medical records stored in the data store 420 may be indexed or otherwise organized (e.g., for more efficient and accurate generation of the medical record digest 118 by the digest server 418). The organization may group portions of records by medical category (e.g., as described above with reference to the operation 210 of FIG. 2A).

As also shown in FIG. 3B, the exchange server 497 and data store 496 implement the exchange system 165 of FIG. 1. The data store 496 can be implemented by, for example, a database (e.g., a relational database) and stored on a non-transitory storage medium. The data store 496 is configured to store medical records (e.g., the medical record 110 of FIG. 1) in association with patient reference codes (e.g., the patient reference code 111 of FIG. 1). The medical records stored in the data store 496 may be indexed or otherwise organized (e.g., for more efficient and accurate generation of the patient medical records 192 by the exchange server 497). The organization may group portions of records by patient. The data store 496 is also configured to store associations between endpoints (e.g., source of medical data) and patients. These associations may be stored, for example, as rows within one or more relational database tables. In some examples, the data store 496 stores the implemented data model 250 of FIG. 2C. Further, in an implementation, the data store 496 can couple to and be accessed by the other processes hosted in the cloud environment 402 and the mobile EMS environment 404. In another implementation, the data store 496 can only couple to and be accessed by the other processes hosted in the cloud environment 402. It should be noted that the data store 496 can, in some examples, store medical record digests generated by the digest system 102 of FIG. 1, as the medical record digests can be subject to subscription and publication via the incident data exchange system 165 of FIG. 1.

In some examples, the exchange server 497 is configured to interoperate with the CAD server 430, the navigation server 428, the charting server 422, the billing server 467, the digest server 418, and/or the case data store 424 to acquire patient identification data and supplemental identification data as described above with reference to the process 300 of FIG. 2B. Further, in these examples, the digest server 418 and/or the exchange server 497 is configured to interoperate with the CAD server 430, the charting server 422, the case data store 424, and the billing server 467, via the exchange server 497, to gather medical records for patients. It should be noted that, in some examples, the digest server 418 and/or the exchange server 497 is configured to periodically update medical records by interoperating with the other servers in the platform 426 and/or devices within the mobile EMS environment 404. For instance, in one example, the digest server 418 and/or the exchange server 497 periodically requests updated billing codes from the billing server 467 and updates medical records stored in the data store 420 and/or the data store 496 accordingly. These billing codes are a source of information for previous medical treatments. For instance, billing codes can indicate that a patient received treatment for asthma, treatment for cardiac arrest, treatment for a drug overdose, prescription information, and/or recent surgeries. This information may be clinically actionable and relevant. For example, stitches from recent surgeries could reopen. Devices implanted during surgery may need to be addressed. Treatments for drug overdose may indicate a need to avoid opioids. Repeated treatments and prescriptions could indicate chronic conditions and/or contraindications.

In some examples, the digest server 418 is also configured to generate medical record digests (e.g., the medical record digest 118 of FIG. 1) and transmit the medical record digests to the digest application 440 for display via the digest GUI 442. The digest application 440 is configured to generate and render notifications to users in response to receiving a medical record digest, as described above.

Continuing with FIG. 3B, the CAD server 430 implements the CAD system 130 of FIG. 1. As shown in FIG. 3B, the CAD server 430 receives a request to record calls from the PSAP and processes the requests to generate and store call records. The CAD server 430 transmits dispatch requests to the EMS agency 412 to dispatch EMS personnel (e.g., the care provider 112 of FIG. 1) to service calls. The CAD server 430 transmits addresses to call locations to the navigation application 444 so that the navigation application 444 can acquire routes to call locations by interoperating with the navigation server 428. The navigation device 436, in turn, interoperates with the positioning system 414 to provide real time, step by step directions to call locations via the routes.

Continuing with FIG. 3B, the charting server 422 and the charting application 438 implement an EMS patient charting application (e.g., the patient charting system 429 of FIG. 3A). In one example, the charting application 438 receives input from EMS personnel and/or the medical devices 132 that specifies medical information regarding the patient and stores the medical information in an ePCR. The charting application 438 uploads ePCRs to the charting server 422.

Continuing with FIG. 3B, case data store 424 receives case files uploaded by the medical devices 132. The case data store 424 can be implemented by, for example, a database (e.g., a relational database) and stored on a non-transitory storage medium. In an implementation, the case data store 424 includes a plurality of records that store case data derived from case files from a plurality of medical devices used to treat patients during encounters. Moreover, in some examples, the case data store 424 can store complete copies of the case files themselves (e.g., as large binary objects). The case data stored in the case data store 424 can document patient encounters from the point of view of medical devices. As such, case data generated by a medical device during a patient encounter can include an identifier of the medical device, physiologic parameter values of the patient recorded by the medical device during the encounter, characteristics of treatment provided by the medical device to a patient during the encounter, actions taken by care providers during the encounter, and timestamps associated with medical device case data. For instance, where the medical device is a defibrillator, the case data can include patient physiological parameters such as ECG data for the patient, as well as characteristics of therapeutic shocks delivered by the defibrillator to the patient, CPR performance data, and timestamps reflecting a power-on time for the defibrillator and associated with recorded case data, among other information.

The data stores 420, 496, and 424 can be organized according to a variety of physical and/or logical structures.

In at least one example, the data stores 420, 496, and 424 are implemented within a relational database having a highly normalized schema and accessible via a structured query language (SQL) engine, such as ORACLE or SQL-SERVER. This schema can, in some implementations, include columns and data that enable the data stores 420, 496, and 424 to house data for multiple tenants. In addition, although the description provided above illustrates the data stores 420, 496, and 424 as relational databases, the examples described herein are not limited to that particular physical form. Other databases may include flat files maintained by an operating system and including serialized, proprietary data structures, hierarchical database, xml files, NoSQL databases, document-oriented databases and the like. Thus, the data stores 420, 496, and 424 as described herein are not limited to a particular implementation.

Continuing with FIG. 3B, the billing server 467 implements a medical billing system (e.g., the medical billing system 425 of FIG. 3A). The billing server 467 can store patient identification data, information regarding claims involving patients, payments status of the claims, and the like. Insurance claims may include procedure codes, for example, may include Current Procedural Terminology (CPT®) codes and/or Healthcare Common Procedure Coding System (HCPCS) codes. Rather than or in addition to the procedure codes, in some implementations, the claim information includes reference codes or identifiers not included in the CPT and/or HCPCS listings such as, in some examples, medical equipment and/or supply identifiers, prosthetics and/or orthotics devices and supplies identifiers, home health services identifiers, and/or prescription drug identifiers. The patient identification data stored in the billing server 467 can include, for example, patient provider and insurance information. In some implementations, the billing server 467 also hosts the demographic verifier 499 of FIG. 3A.

In various implementations, the medical device(s) 132 can include a patient treatment device, or another kind of device that includes patient monitoring and/or patient treatment capabilities, according to examples of the present disclosure. For example, the medical device(s) 132 include a defibrillator and can be configured to deliver therapeutic electric shocks to the patient. In some examples, the medical device(s) 132 can deliver other types of treatments, such as ventilation, operating a respirator, and/or administering drugs or other medication. Additional examples of the medical device(s) 132 are described further below with reference to FIG. 11. In combination, the systems illustrated in FIG. 3B can produce accurate and comprehensive documentation that improves continuity of patient care and overall patient health outcomes. More specifically, continuity of care may benefit from a record that thoroughly describes symptoms, physiological scores, and treatments provided.

Figure 4A:
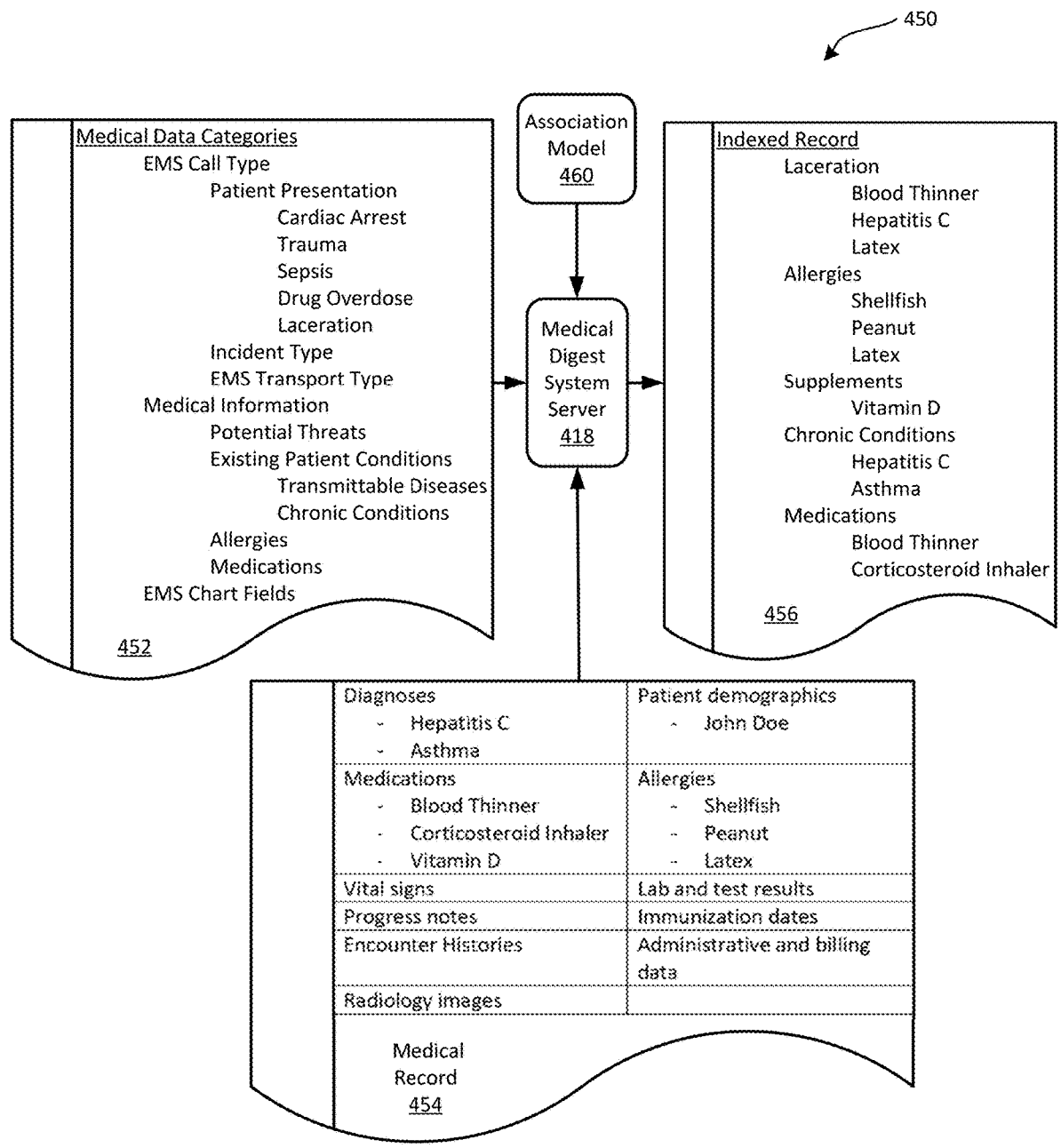
FIG. 4A is a schematic block diagram illustrating an indexing data flow in accordance with at least one example disclosed herein.

FIG. 4A illustrates a data flow and process 450 used to generate an indexed record 456. The data processed according to the example of FIG. 4A includes a list of medical data categories 452, a medical record 454, an association model 460, and the indexed record 456. As shown in FIG. 4A, the digest server 418 opens the list 452 and the medical record 454. Next, the digest server 418 loads the association model 460 that enables the digest server 418 to assign tags corresponding to one or more medical categories in the list 452 to portions of the medical record 454. For example, the association model 460 may be a cross-reference data structure that associates medical data categories with types of data found in portions of medical records. For instance, such a data structure may include a record that associates blood thinners with a laceration medical category. In this instance, the digest server 418 tags any portion of the medical record 454 reciting a blood thinner with a "laceration" tag and stores the resulting combination in the indexed record 456.

However, other approaches to indexing the medical record 454 are possible. For instance, the association model 460 may include a set of rules that associate medical data categories with types of data found in portions of medical records. Such rules sets enable more logically complex associations to be established. For example, a rule set can require that a particular portion of the medical record 454 be associated with every EMS call type via a tag. For instance, such a rule set may require that a Covid-19 diagnosis appearing in the medical record 454 be tagged for all EMS call types. Further still, machine learning models can be used to index records where the complexity of the desired associations and/or temporal dynamics make a machine learning model appropriate.

Continuing with the example data flow 450, the digest server 418 stores tagged portions of the medical record 454 in the indexed record 456. In this particular example, the indexed record 456 includes tags for laceration, allergies, supplements, chronic conditions, and medications. The laceration tag is assigned to (and groups) portions of the medical record 456 disclosing the patient's use of a blood thinning medication, the patient's diagnosis of hepatitis C, and the patient's allergy to latex. The allergies tag is assigned to portions of the medical record 456 disclosing the patient's allergies to shellfish, peanuts, and latex. The supplements tag is assigned to portions of the medical record 456 disclosing the patient's use of Vitamin D as a supplement. The chronic conditions tag is assigned to portions of the medical record 456 disclosing the patient's diagnosis of hepatitis C and asthma. The medications tag is assigned to portions of the medical record 456 disclosing the patient's use of blood thinners and a corticosteroid inhaler.

Figure 4B:
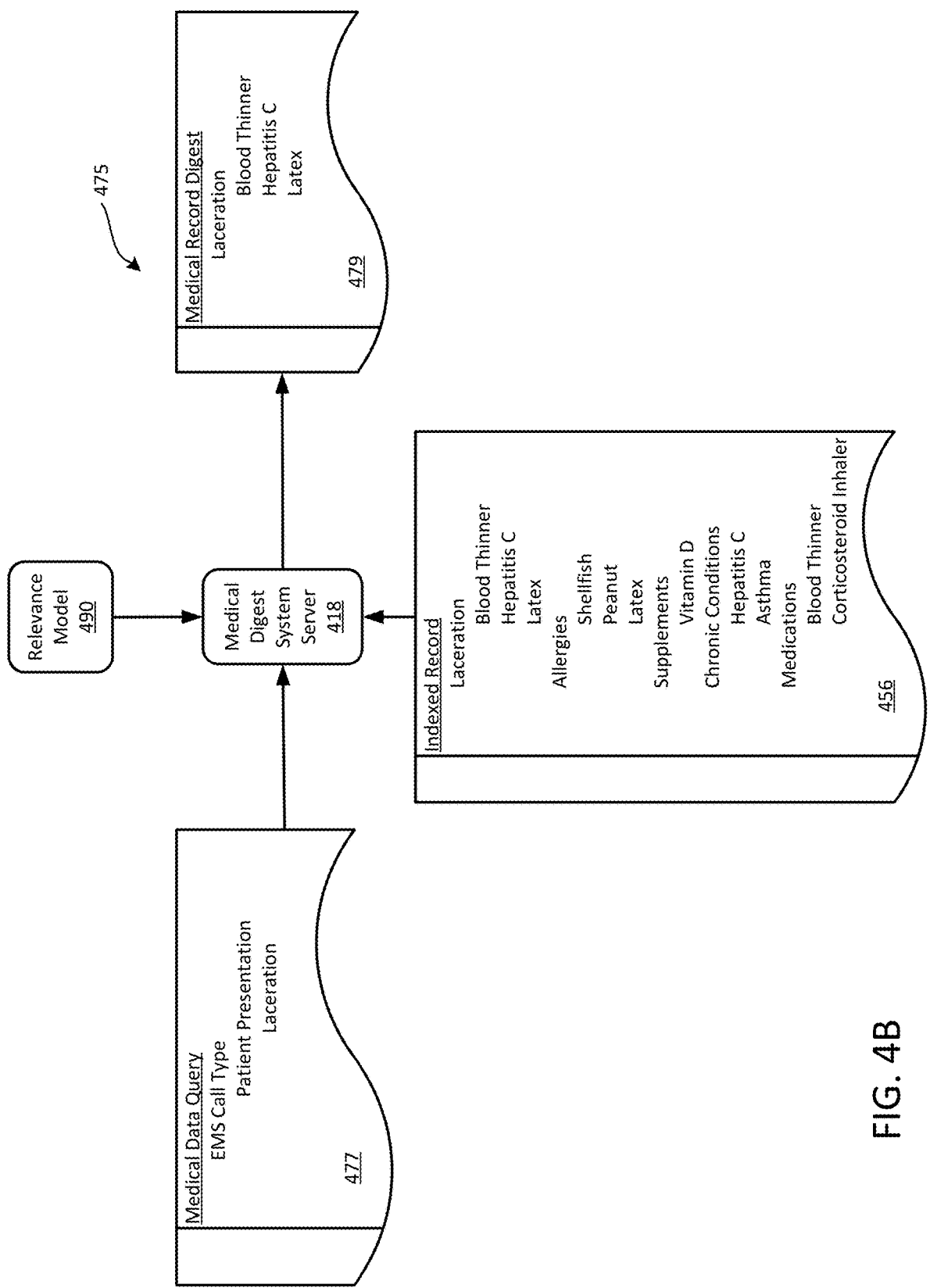
FIG. 4B is a schematic block diagram illustrating a digest generation data flow in accordance with at least one example disclosed herein.

FIG. 4B illustrates a data flow and process 475 used to generate a medical record digest 479. The data processed according to the example of FIG. 4B includes medical data query 477, an indexed record 456, a relevance model 490, and the digest 479. As shown in FIG. 4B, the digest server 418 opens the query 477 and the indexed record 456. Next, the digest server 418 loads the relevance model 490 that enables the digest server 418 to identify portions of medical data to include in the digest 479. For example, the relevance model 490 may be a cross-reference data structure that associates medical data categories from the query 477 with tags found in index records. For instance, such a data structure may include a record that associates a laceration tag with a laceration medical category identified in the query. In this instance, the digest server 418 parses the query 477, identifies the laceration medical category, identifies the laceration tag in the data structure as being associated with the laceration medical category, identifies the laceration tag in the indexed record 456, and stores the laceration medical data in the digest 479.

However, other approaches to generating the digest 479 are possible. For instance, the relevance model 490 may include a set of rules that associate medical data categories with tags found in indexed records. Such rules sets enable more logically complex associations to be established. For example, a rule set can require that a particular portion of the indexed record 456, when present, be included in every digest 479. For instance, such a rule set may require that a Covid-19 diagnosis appearing in the indexed record 456 be included in all digests. Further still, machine learning models can be used to generate digests where the complexity of the desired associations and/or temporal dynamics make a machine learning model appropriate. These models may further benefit from the predictive nature of some machine learning processes.

Figure 5B:
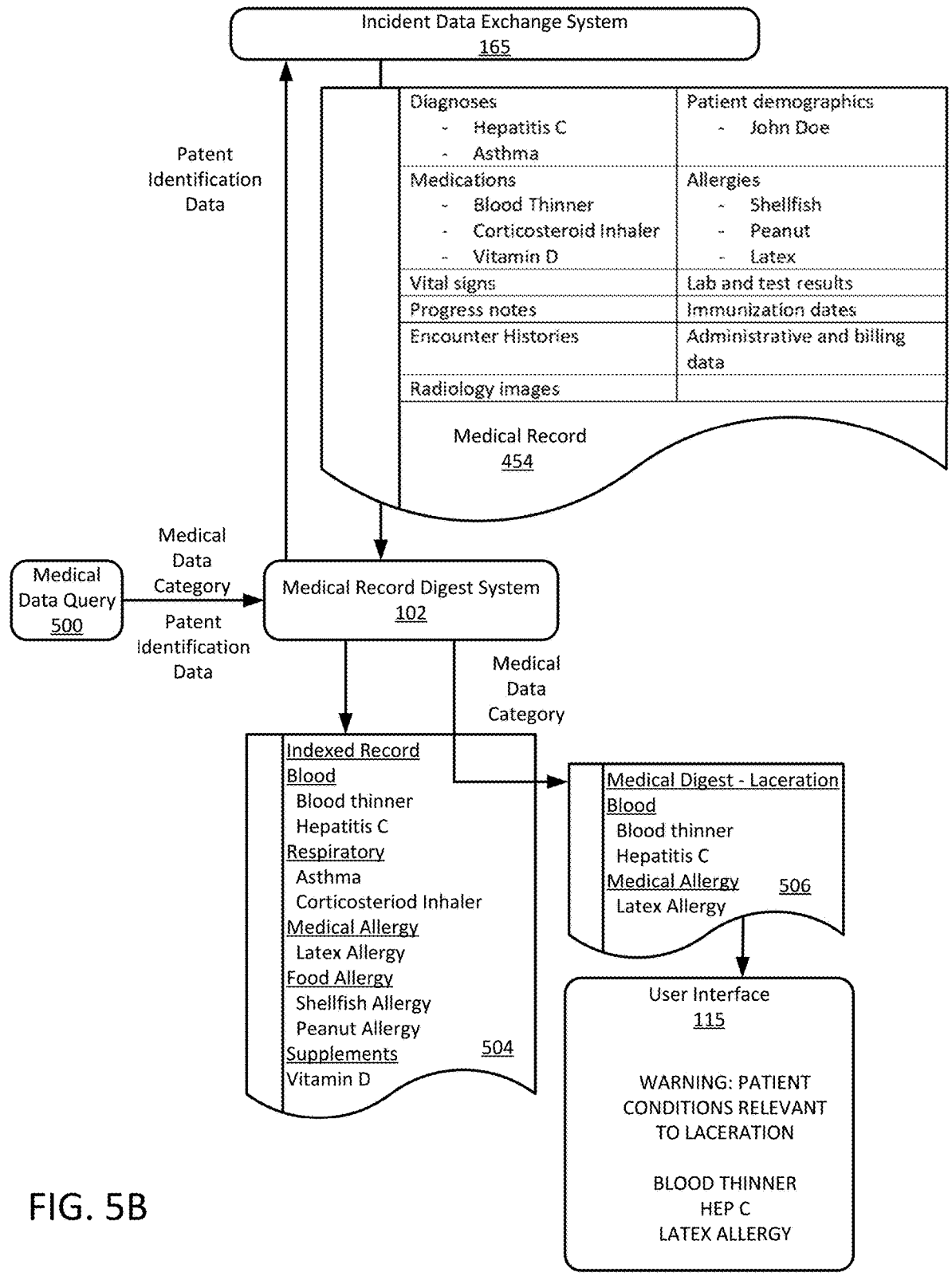
FIG. 5B is a schematic block diagram illustrating select data flows within a SaaS platform in accordance with at least one example disclosed herein.

To aid the reader's understanding of the capabilities of the systems and processes described herein, several detailed examples will now be described with reference to FIGS. 5A-5D. It should be noted that these examples are not presented for purposes of limitation but rather to illustrate by example. FIG. 5A illustrates a relatively simple medical record 501. As shown in FIG. 5A, the record 501 includes sections regarding patient details, alerts, diagnosis, care providers, medications, encounter history, immunizations, and diabetic indices. Each of these sections include further details that will not be recited here for purposes of brevity. However, it should be noted that, as illustrated by the record 501, the medical records processed by the examples described herein may be voluminous and difficult to comprehend quickly.

FIG. 5B depicts one selected example flow of data generated by a SaaS platform (e.g., the platform 100 of FIG. 1) including the digest system 102 of FIG. 1. As shown in FIG. 5B, the digest system 102 receives a medical data query 500. The medical data query 500 specifies the medical data category and patient identification data. In response to receiving the medical data query 500, the digest system 102 queries the exchange system 165 of FIG. 1 for a medical record associated with the patient identification data.

Continuing with the data flow illustrated in FIG. 5B, the exchange system 165 returns a medical record 454 associated with the patient identification data to the digest system 102. An example of the medical record 454 includes a list of known allergies (shellfish, peanut, and latex), a list of known ailments (hepatitis C and asthma), and a list of known medications/supplements (blood thinner, corticosteroid inhaler, and vitamin D). In response to receiving the medical record 454, the digest system 102 converts the medical record 454 into the indexed record 504 to facilitate more rapid access to its contents. As shown in FIG. 5B, the record 504 is indexed using tags into the following medical data categories: Blood, Respiratory, Medical Allergy, Food Allergy, and Supplements. The tag related to blood includes entries for blood thinner and hepatitis C. The tag related to respiratory includes entries for asthma and corticosteroid inhaler. The tag related to medical allergy includes an entry for latex allergy. The tag related to food allergy includes entries for shellfish allergy and peanut allergy. The tag related to supplements includes an entry for vitamin D.

Continuing with the data flow illustrated in FIG. 5B, the digest system 102 may extract a medical data category from the medical data query 500. In this example, the medical data category is laceration. The digest system 102 identifies tags of the indexed record 504 associated with the medical data category of laceration by accessing a data structure that associates medical data categories with tags. This data structure includes an association between the laceration and blood and between laceration and medical allergy. The digest system 102 retrieves, from the indexed record 504, the entries related to blood (i.e., blood thinner and hepatitis C) and medical allergy (i.e., latex allergy). The digest system 102 generates a medical digest record 506 that contains the retrieved entries within a helpful message—"WARNING: PATIENT MEDICAL CONDITIONS RELEVANT TO LACERATION: BLOOD THINNER, HEP C, LATEX ALLERGY". The digest system 102 transmits the medical digest record 506 to a user interface device (e.g., the user interface device 106 of FIG. 1). The user interface device renders the medical digest record via the user interface 115.

Figure 5C:
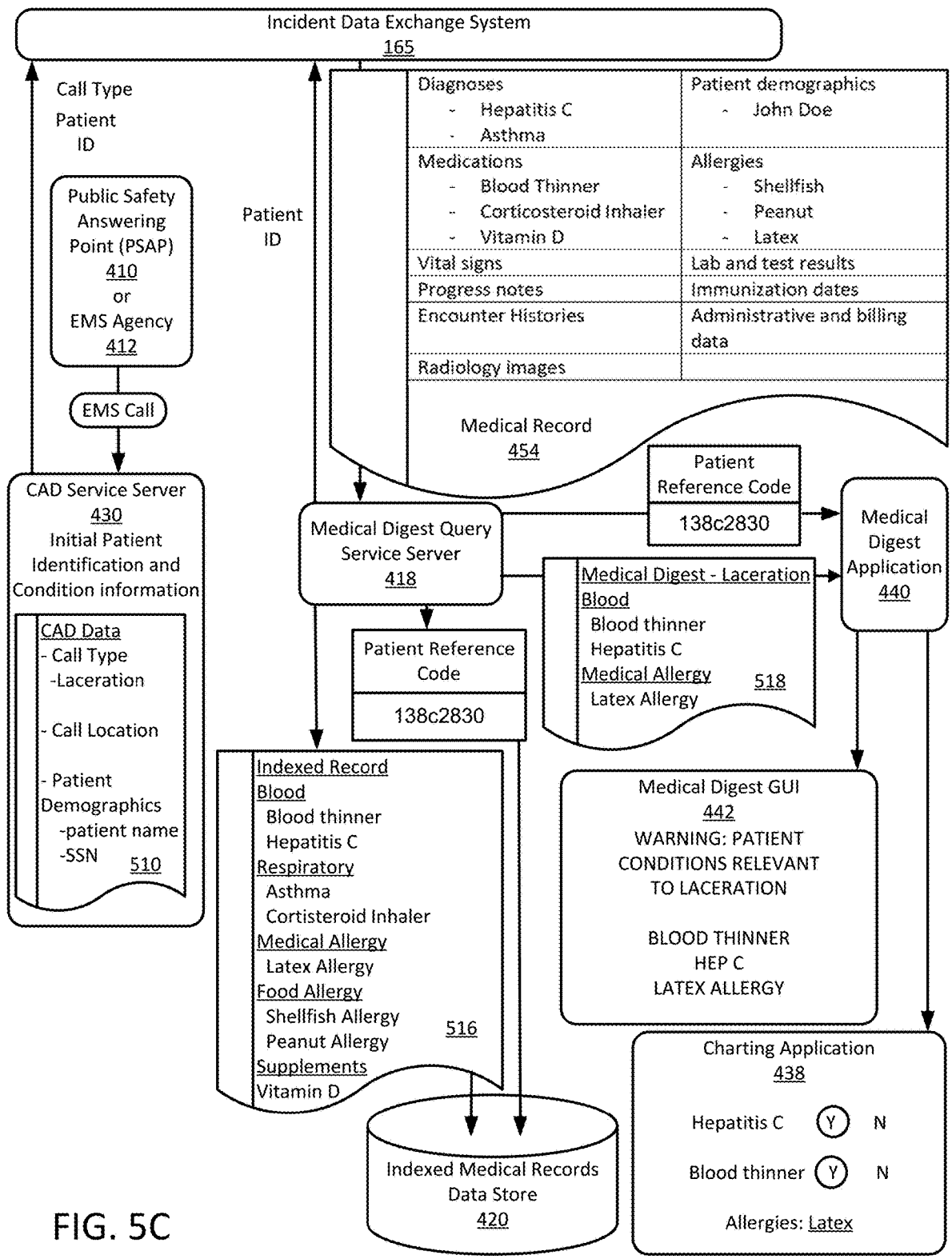
FIG. 5C is a schematic block diagram illustrating additional select data flows within a SaaS platform in accordance with at least one example disclosed herein.

FIG. 5C illustrates an example flow of data generated by a SaaS platform (e.g., the SaaS platform 426 of FIG. 3B) including the digest server 418 and exchange server 497 of FIG. 3B. As shown in FIG. 5C, the PSAP 410 or EMS agency 412 of FIG. 3B enters a call into the CAD server 430 of FIG. 3B. A record 510 for the call specifies initial patient identification (e.g., location, demographics, name, social security number, etc.) and condition information (e.g., the call type is laceration). The CAD server transmits the call type and initial patient identification to the exchange server 497. In response to receiving the call type and initial patient identification, the exchange server 497 queries a repository for a medical record associated with the patient identification data and generates a patient reference code 138c2830. The repository can be, for example, a HIE system or an EHR system (e.g., one of the systems 105 of FIG. 1).

Continuing with the data flow illustrated in FIG. 5C, the repository returns a medical record 454 associated with the patient identification data to the exchange server 497 and the exchange server 497 publishes the medical record 454, including the patient reference code, to the digest server 418. The medical record 454 includes a list of known allergies (shellfish, peanut, and latex), a list of known ailments (hepatitis C and asthma), and a list of known medications/supplements (blood thinner, corticosteroid inhaler, and vitamin D). In response to receiving the medical record 454, the digest server 418 converts the medical record 454 into an indexed record 516. As shown in FIG. 5C, the record 516 is indexed into the following medical data categories: Blood, Respiratory, Medical Allergy, Food Allergy, and Supplements. The tag related to blood includes entries for blood thinner and hepatitis C. The tag related to respiratory includes entries for asthma and corticosteroid inhaler. The tag related to medical allergy includes an entry for latex allergy. The tag related to food allergy includes entries for shellfish allergy and peanut allergy. The tag related to supplements includes an entry for vitamin D. The digest server 418 stores the patient reference code 138c2830 and the indexed record 516 in the data store 420 of FIG. 3B.

Continuing with the data flow illustrated in FIG. 5C, the digest server 418 identifies the call type of laceration as a medical data category for the medical record digest. The digest server 418 identifies tags within the indexed record 516 that are associated with the medical data category of laceration by accessing a data structure that associates medical data category with tags. This data structure includes an association between laceration and blood and between laceration and medical allergy. The digest server 418 retrieves, from the indexed record 516, the entries related to blood (i.e., blood thinner and hepatitis C) and medical allergy (i.e., latex allergy) and stores these entries in a medical digest record 518. The digest server 418 transmits the medical digest record 518 and the patient reference code 138c2830 to the medical digest application 440 of FIG. 3B. The medical digest application 440 generates a helpful message from the medical digest record 518. The message recites "WARNING: PATIENT MEDICAL CONDITIONS RELEVANT TO LACERATION: BLOOD THINNER, HEP C, LATEX ALLERGY". The medical digest application 440 renders the message via a display of the user interface device 434 of FIG. 3B. The medical digest application 440 also interoperates with the charting application 438 of FIG. 3B to populate fields within an ePCR associated with the patient reference code 138c2830. The populated values indicate that the patient takes blood thinner, has hepatitis C, and is allergic to latex, within a problems, medications, and allergies format.

Figure 5D:
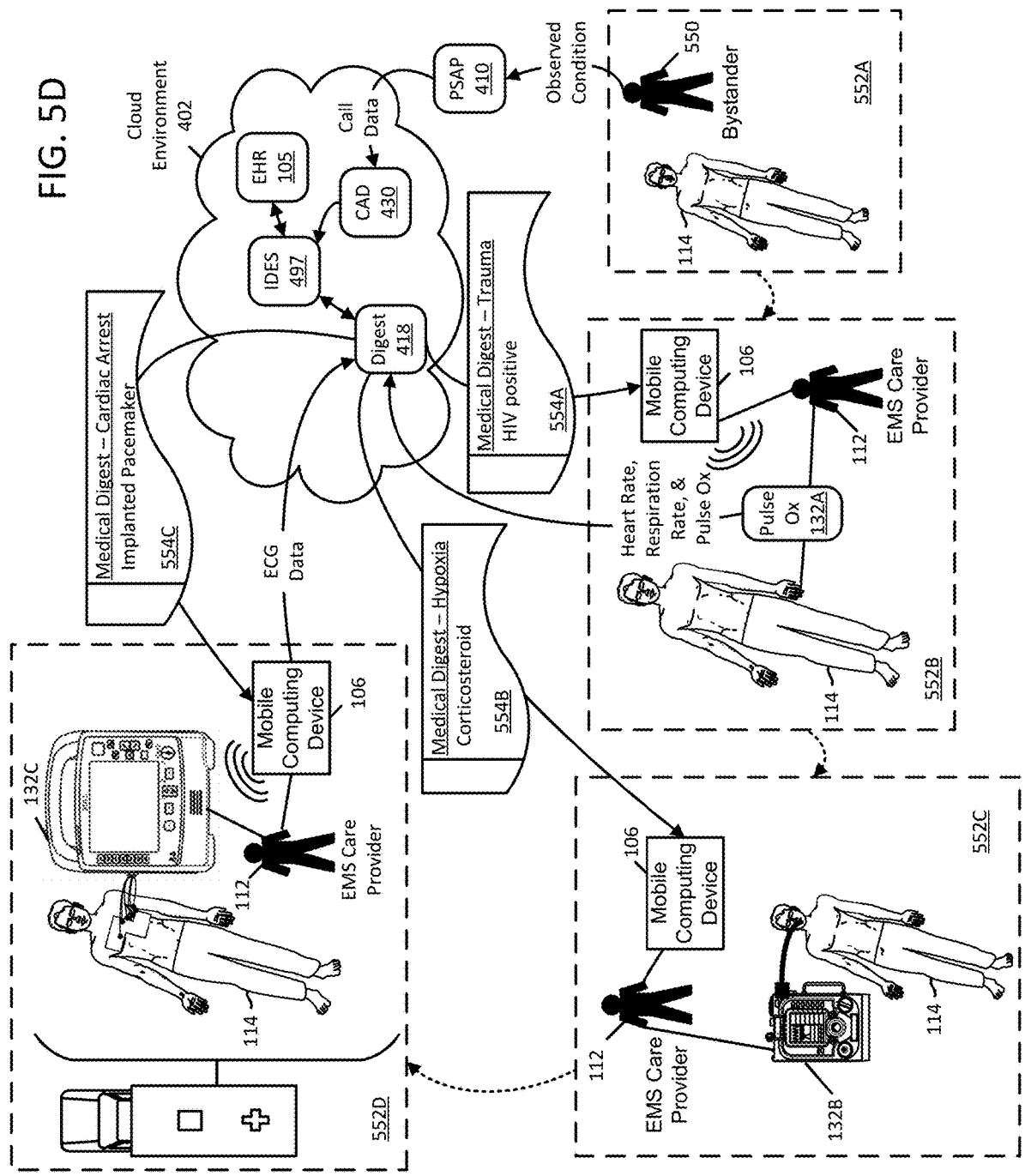
FIG. 5D is a schematic block diagram illustrating an example medical record digest generation process using a SaaS platform in accordance with at least one example disclosed herein.

FIG. 5D illustrates an example of a patient encounter in which the systems and processes described herein support continuity of patient care. With reference to FIG. 5D, a bystander 550 happens upon the scene 552A of a trauma involving a patient 114. The bystander calls PSAP 410 to request assistance. PSAP personnel gather information from the bystander 550 regarding the patient 114. This information includes the patient's observable condition and patient identification data. In this example, the bystander 550 communicates patient identification data sufficient to uniquely identify the patient 114 (e.g., a driver's license) and that the patient 114 is bleeding.

The PSAP 410 enters call data based on the information provided by the bystander 550 into the CAD server 430. The PSAP dispatches an EMS care provider 112 to assist the patient 114. The CAD server 430 autonomously provides a call record to the exchange server 497. The exchange server 497, in response, generates a patient reference code and queries a medical record repository 105 (e.g., an ERR system and/or a HIE system) for the patient's medical record(s). The repository 105 transmits, and the exchange server 497 receives, a copy of the patient's medical record(s) including and in association with the patient reference code. The exchange server 497 publishes the copy of the patient's medical record(s) to the digest server 418. The digest server 418 generates an indexed record from the received medical record(s). The digest server 418 generates a first medical digest 554A based on the EMS call type listed in the call record (trauma). The digest server 418 transmits the medical digest 554A to a user interface device 106 associated with the EMS care provider. The medical digest 554A includes the patient reference code.

Upon his arrival, the EMS care provider 112 glances at the user interface device 106 to determine whether any additional information has been rendered thereon. The EMS care provider 112 discovers that sometime prior to his arrival at scene 552B the digest server 418 generated and transmitted the medical digest 554A, which is focused on trauma involving bleeding. The medical digest 554A warns the EMS care provider 112 that the patient 114 has been diagnosed as being HIV positive. As such, the EMS care provider 112 takes extra precautions when caring for the patient 114.

While administering assistance to the patient 114, the EMS care provider 112 realizes that the patient's pallor indicates that he may be suffering from hypoxia. As such, the EMS care provider 112 fits the patient 114 with a pulse oximetry medical device 132A. In this example, the device 132A is configured to communicate with a variety of network capable devices, including user interface device 106 and the digest server 418. Being unable to uniquely identify the patient 114, the device 132A queries locally connected devices for a patient reference code. The user interface device 106 receives this query and responds with the patient reference code it previously received from the digest server 418. Next, the device 132A transmits physiologic data including heart rate, respiratory rate, and blood oxygenation information to the digest server 418. This physiologic data can be included in a medical data query. Thus as the EMS care provider confirms that the patient is suffering hypoxia by reading the display of the device 132A, the digest server 418 receives telemetry indicating the same issue in conjunction with the patient reference code.

The digest server 418 generates a second medical digest 554B from the indexed record. The second medical digest 554B is directed to hypoxia. The digest server 418 transmits the digest 554B to the device 106. The device 106 displays the digest 554B to the EMS care provider 112, and the EMS care provider learns that the patient 114 has been prescribed a corticosteroid inhaler in the recent past, which indicates the patient 114 suffers from asthma. Given the seriousness of the patient's condition, in scene 552C the EMS care provider 112 intubates the patient 114 and treats the patient with a portable ventilator 132B to increase the patient's blood oxygen level.

Subsequently, the EMS care provider 112 loads the patient onto an ambulance in scene 552D. Unfortunately, the patient 114 enters cardiac arrest, forcing the EMS care provider 112 to fit the patient 114 with a defibrillator 132C. The defibrillator 132C immediately begins to monitor the patient's ECG. In this example, the defibrillator 132C is configured to automatically establish a network connection with the user interface device 106 and to transmit ECG data to the user interface device 106. The user interface device 106, in turn, transmits the ECG data and the patient reference code to the digest server 418. In this example, the digest server 418 receives this telemetry, generates a third medical digest 554C (which is directed to cardiac arrest), and transmits the digest 554C to the user interface device 106. The user interface device 106 renders the digest 554C, thereby informing the EMS care provider that the patient was fitted with an implanted pacemaker last month. The EMS care provider is able to take this important fact into consideration when determining next steps in caring for the patient 114.

As illustrated by the example described above, the medical record digest systems and processes described herein can aid or enable the provision of situationally dependent medical record(s) distillations that provide guidance for the care provider in a context based workflow.

Figure 6:
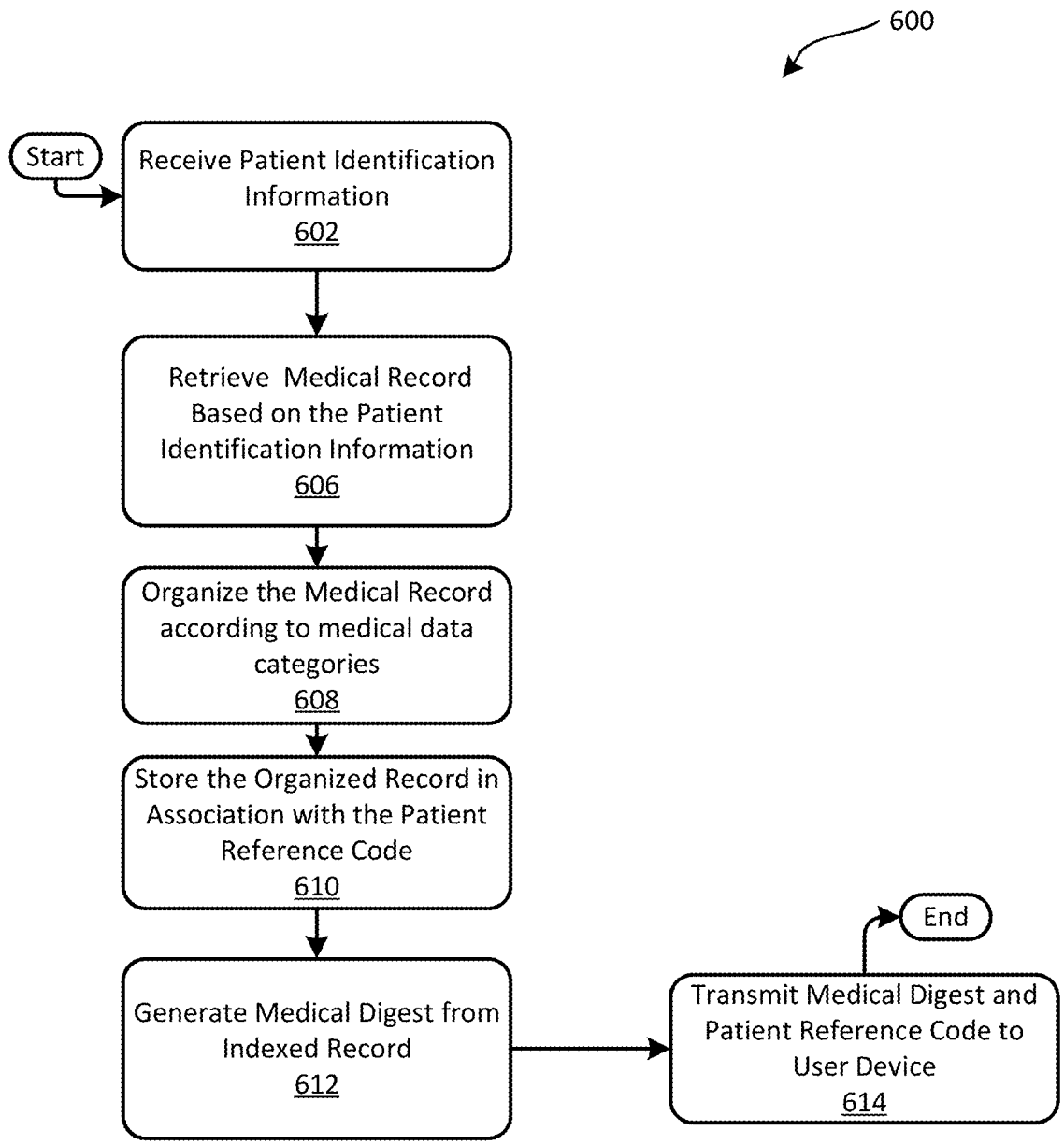
FIG. 6 is a flow diagram of a digest generation process executed by a medical record digest system in accordance with at least one example disclosed herein.

FIG. 6 illustrates one example of a digest generation process 600 that at least some implementations of the digest system 102 of FIG. 1 and the digest server 418 are configured to execute. As shown in FIG. 6, the process 600 starts with a processor (e.g., the processor 103 of FIG. 1) receiving 602 information identifying a patient. For example, the processor can receive an incident record from an exchange system (e.g., the exchange system 165 of FIG. 1) that includes a patient's first and last name, date of birth, social security number, and a patient reference code. For example, the patient reference code can be a hash based on the values included in the patient identification data.

Continuing with the process 600, the processor retrieves 606 a medical record for the patient based on the information received in the operation 602. For instance, in one example, the processor generates a query that adheres to the HL7 standard that includes the patient identification data. In this example, the processor transmits the query to the exchange system, which supports the HL7 standard. Further, in this example, the processor receives and parses a response to the query that includes the medical record for the patient.

Continuing with the process 600, the processor organizes the medical record according to one or more categories of medical data. In an implementation, the processor organizes and/or sorts the medical record according the categories of medical data by converting the medical record into an indexed record. Examples of indexing operations are described above with reference to the operation 208 of FIG. 2A.

Continuing with the process 600, the processor stores 610 the organized record in association with the patient reference code. For instance, in one example, the processor stores the indexed record in a database and creates an entry within a data structure that associates the patient reference code with an identifier of the indexed record.

Continuing with the process 600, the processor generates 612 a medical record digest from the indexed record. For instance, in one example, the processor identifies one or more categories of medical data to be included in a medical record digest (e.g., one or more categories included in a medical data query) and identifies tags of indexed records associated with the one or more categories (e.g., via a data structure that associates tags of indexed records with categories of medical data). Next, the processor retrieves entries of the identified tags from the indexed record and generates a medical record digest using the retrieved entries. In some examples, the processor further structures the medical record digest to increase its human readability via a natural language generation process/grammar checker.

Continuing with the process 600, the processor transmits 614 the medical record digest and the patient reference code to a user device (e.g., the user interface device 106 of FIG. 1). For instance, the processor can control a network interface to transmit the medical record digest to a client application hosted on the user device.

Figure 7A:
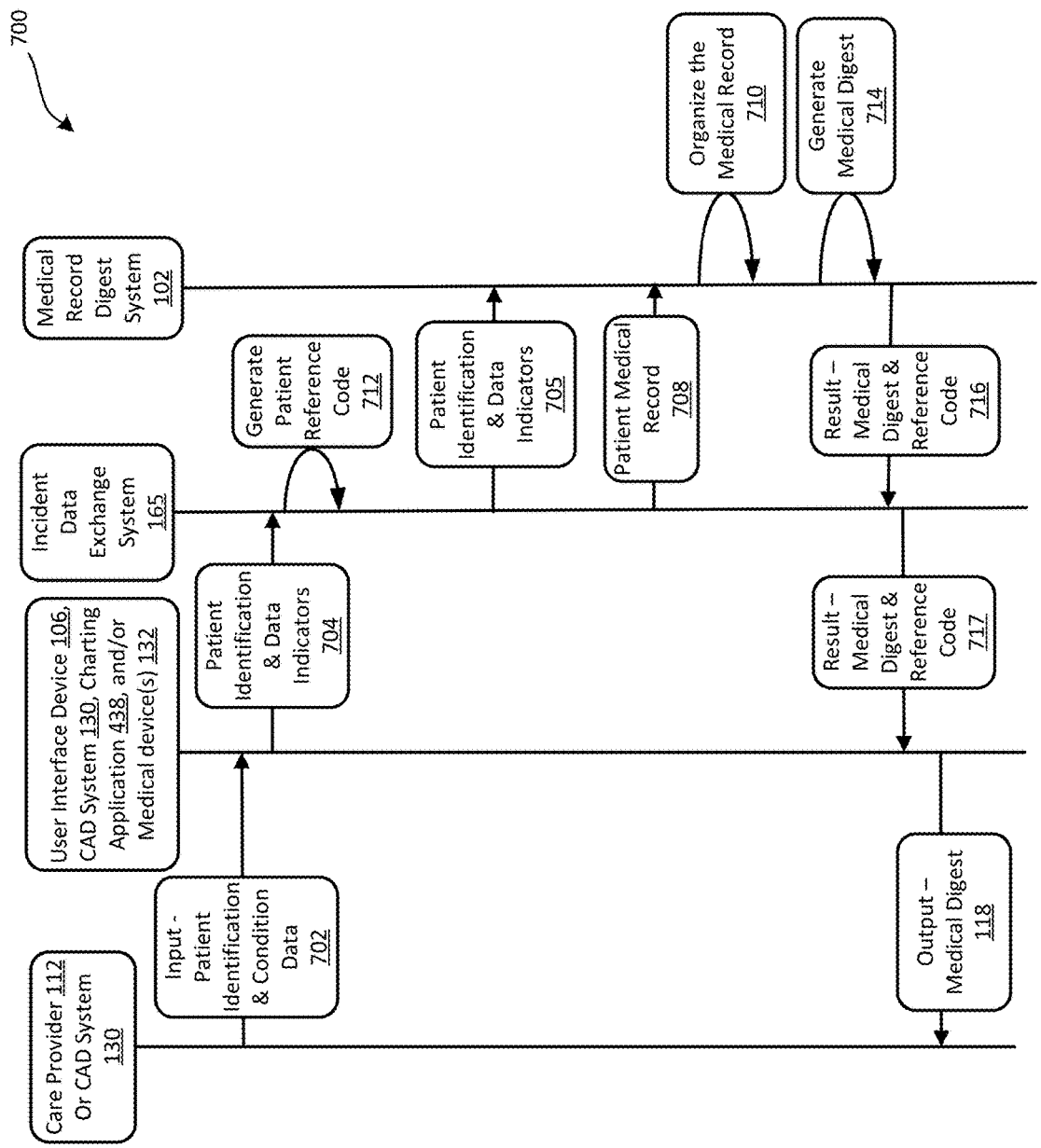
FIG. 7A is a sequence diagram of a digest generation process in accordance with at least one example disclosed herein.

FIG. 7A is a sequence diagram illustrating process and data flows of a digest generation process 700 in accordance with some examples. As shown in FIG. 7A, the process 700 begins with a care provider (e.g., the care provider 112 of FIG. 1) or user of a CAD system (e.g., the CAD system 130 of FIG. 1) entering input 702 identifying a patient and/or a patient's medical condition into a computing device (e.g., the user interface device 106 or the CAD system 130 of FIG. 1 or the charting application 438 of FIG. 3B). One or more of the recipients of the input 702 generate an exchange system input 704 and transmit the input 704 to an exchange system (e.g., the exchange system 165 of FIG. 1). For example, the exchange system input 704 may be the medical data query 195 or a call record. The exchange system input 704 specifies the patient identification and/or medical data indicators. The exchange system processes the digest system input 704, generates 712 a patient reference code, and aggregates medical records 709 for the patient identified in the patient identification data (interoperating with medical records repositories as needed). The exchange system passes the patient identification data and the medical data indicators 705 and the patient's medical records to a digest system (e.g., the digest system 102 of FIG. 1).

The digest system organizes 710 the medical record, for example, to generate an indexed record using processes previously described herein (e.g., the operation 208 of FIG. 2A and the operation 608 of FIG. 6). The digest system generates 714 a medical record digest using processes previously described herein (e.g., the operation 612 of FIG. 6). The digest system transmits a result 716 to the exchange system. The exchange system processes the result 716 and transmits a result 717 based thereon to a digest recipient (e.g., one or more of the user interface device 106, the CAD system 130, the charting application 438, and/or the medical devices 132). In an implementation, the digest recipient may be the sender of the exchange system input 704. The result includes the medical record digest and the patient reference code. The digest recipient processes the result 717 and renders the medical record digest 118 as output to a digest recipient (e.g., the care provider 112 and/or the CAD system 130). In an implementation, the digest recipient may be the originator of the input 702. After the medical record digest 118 is rendered, the process 700 ends.

Figure 7B:
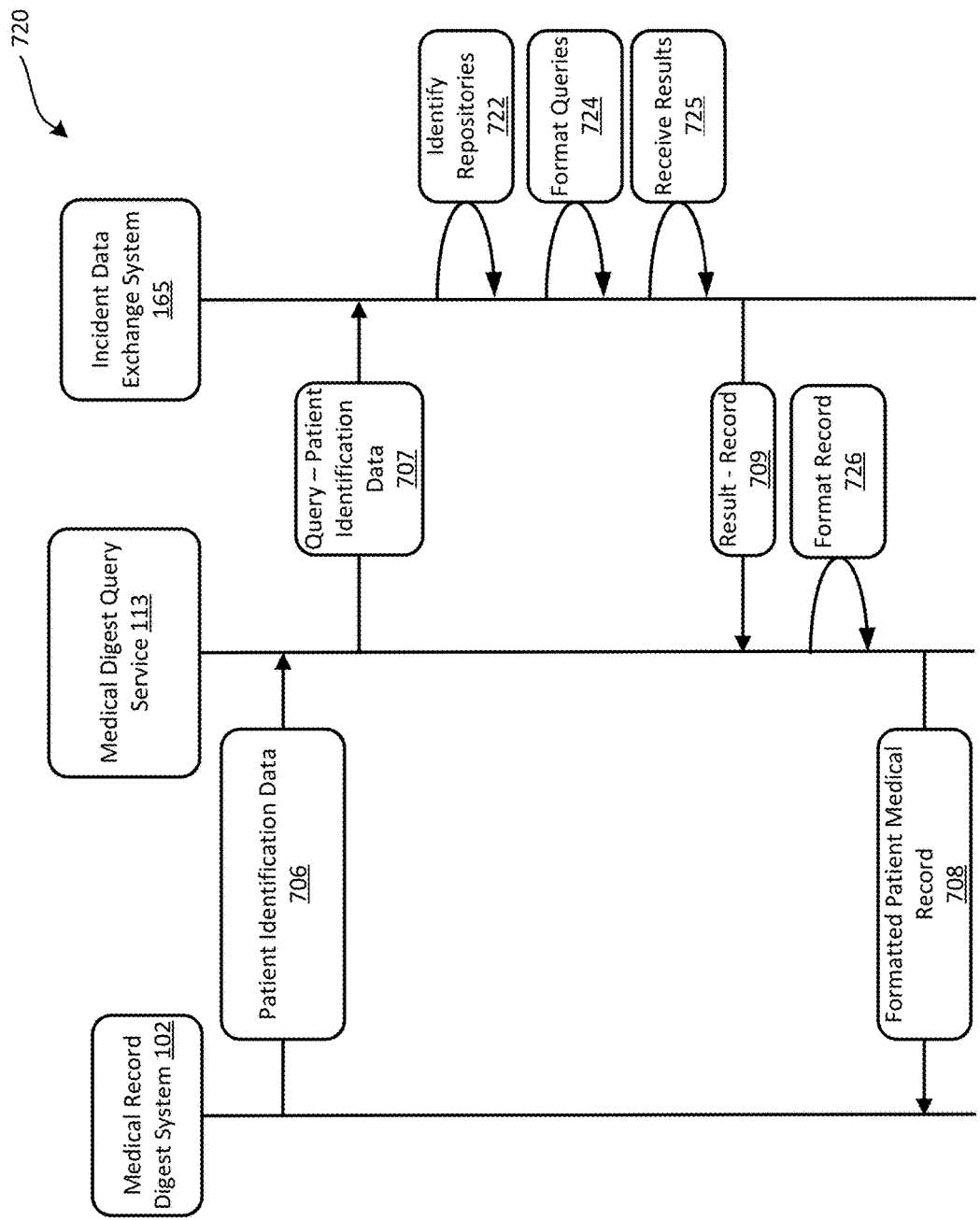
FIG. 7B is a sequence diagram of a medical record query process in accordance with at least one example disclosed herein.

FIG. 7B is a sequence diagram illustrating process and data flows of a medical record(s) process 720 in accordance with some examples. As shown in FIG. 7B, the process 720 begins with the digest system passing the patient identification data 706 to a query service (e.g., the medical digest query service 113 of FIG. 1). The query service receives the patient identification data 706 and formats 724 a query 707 for medical record(s) of the patient that complies with a communication standard supported by an exchange system (e.g., the exchange system 165 of FIG. 1). The query 707 includes the patient identification data. The query service transmits the query 707 to the exchange system. The exchange system, operating in ad-hoc mode, receives the query 707 and identifies 722 a repository (e.g., the medical records repository 105 of FIG. 1) that stores the patient's medical record(s), or a portion thereof, using processes previously described herein (e.g., in relation to the exchange system 165 of FIG. 1). The exchange system identifies a communication standard supported by the repository using processes previously described herein (e.g., in relation to the exchange system 165 of FIG. 1). The exchange system formats 724 a query for the medical record(s) of the patient to comply with the communication standard supported by the repository. The query includes the patient identification data. The query service transmits the query to the repository. The repository receives the query and processes the query to generate a result including the patient's medical record(s).

Continuing with the process 720, the repository transmits the result to the exchange system. The exchange system receives 725 the result, processes (e.g., parses, validates, and/or reformats) the result to generate a result record 709, and transmits the result record 709 to the query service. The query service receives the result record 709 and processes the result record 709 to extract the patient's medical record(s). The query service formats or organizes 726 the patient's medical record(s) to create a formatted medical record 708. In an implementation, the formatted medical record 708 may be the indexed medical record discussed above. The query service passes the formatted medical record 708 to the digest service, and the process 720 ends.

Figure 7C:
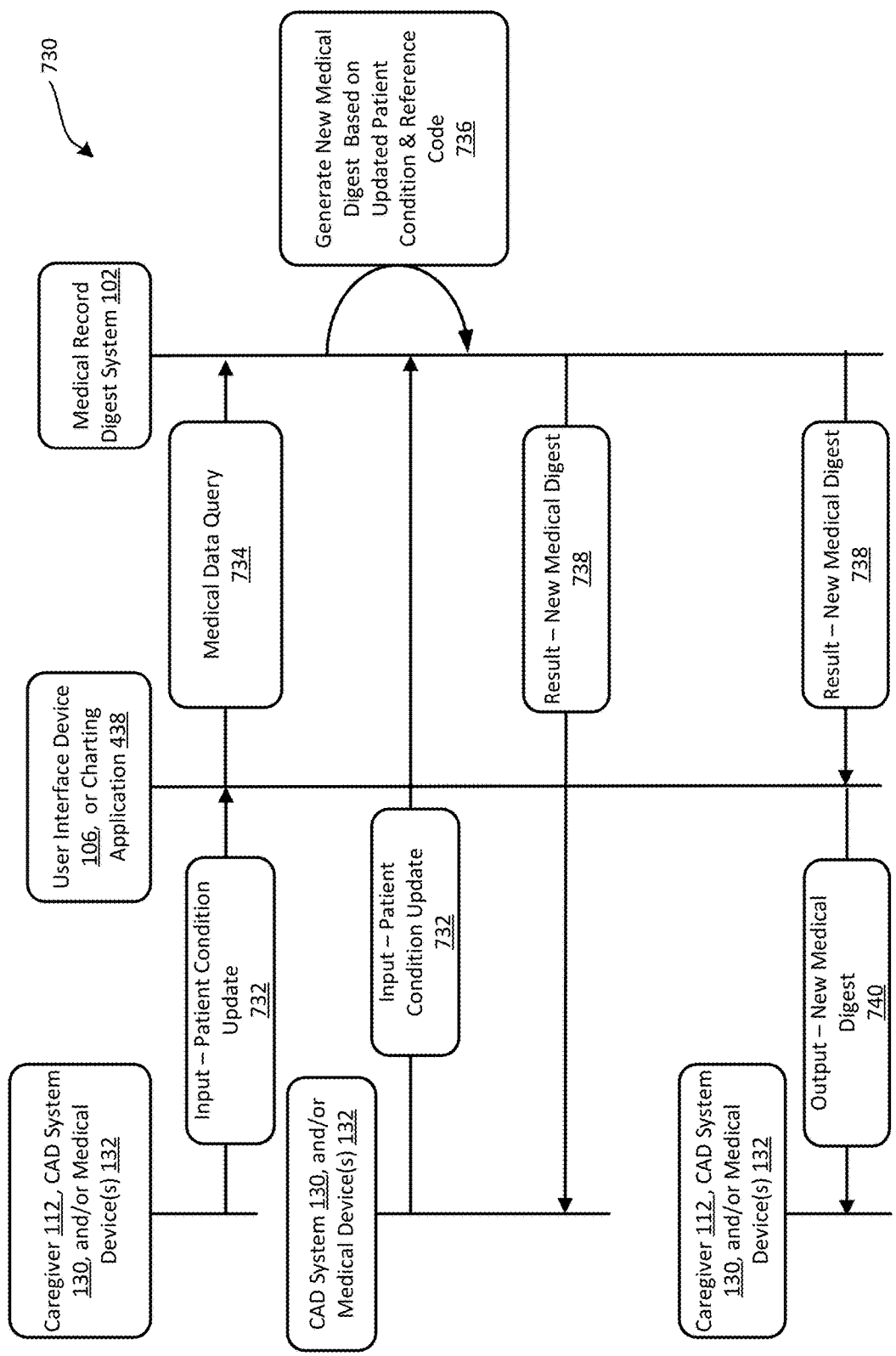
FIG. 7C is a sequence diagram of a digest update process in accordance with at least one example disclosed herein.

FIG. 7C is a sequence diagram illustrating process and data flows of a digest update process 730 in accordance with some examples. As shown in FIG. 7C, in an implementation, the process 730 begins with a care provider (e.g., the care provider 112 of FIG. 1), the CAD system (e.g., the CAD system 130 of FIG. 1), and/or the medical devices 132 providing input 732 updating a patient's medical condition to the user interface device 106 and/or the charting application 438. In turn, the user interface device 106 and/or the charting application 438 may generate an updated medical data query 734 and transmit this query 734 to a digest system (e.g., the digest system 102 of FIG. 1). The query 734 specifies the previously identified or generated patient reference code and the patient's updated medical condition. Additionally or alternatively, one or more of the CAD system 130 and the medical device(s) 132 may provide patient condition update information to the medical record digest system. The patient condition update information may include the patient reference code. Additionally or alternatively, one or more of the CAD system 130 and the medical device(s) 132 may communicate patient condition update information to an exchange system (e.g., the exchange system 165 of FIG. 1) operating in subscription/publication mode. In this event, the exchange system may process the patient condition update information and publish patient medical records including the patient update information to the digest system.

The digest system processes the query 734 to generate 736 an updated medical record digest using processes previously described herein (e.g., the operation 612 of FIG. 6). In an implementation, the digest system transmits a result 738 to the query 734 to the sender of the query 734 (e.g., the user interface device 106 and/or the charting application 438). The result 738 includes the medical record digest and the patient reference code. The sender of the query 734 processes the result 738 and renders the updated medical record digest as output 740 to the originator of the input 702. Additionally or alternatively, the digest system may transmit the result 738 to one or more of the CAD system 130, and/or the medical device(s) 132. After the updated digest results are received, the process 700 ends.

Figure 8:
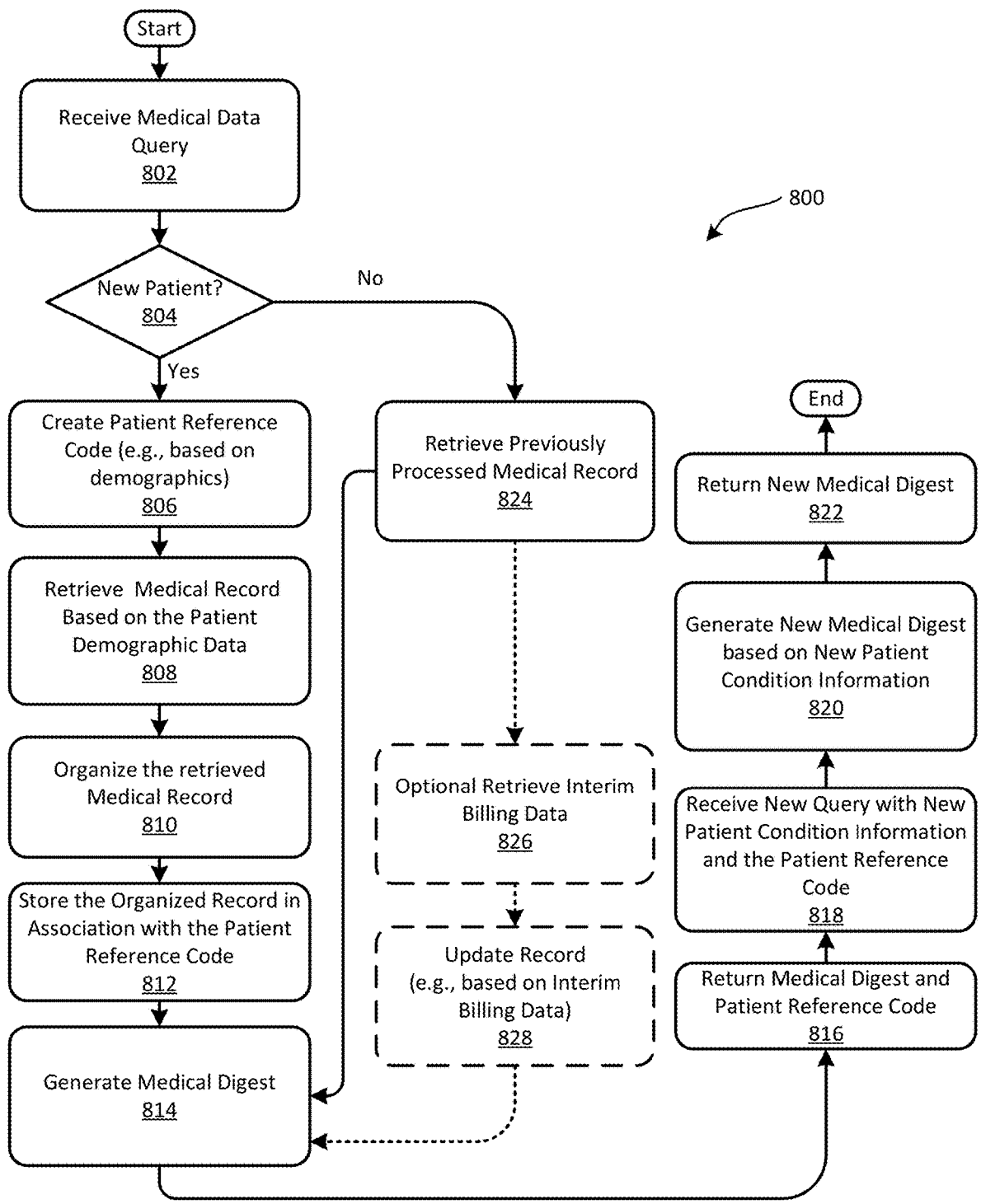
FIG. 8 is a flow diagram of a digest generation and update process in accordance with at least one example disclosed herein.

FIG. 8 is a flow diagram illustrating a digest generation and update process 800 executed by some examples of a digest system (e.g., the digest system 102 of FIG. 1) and an exchange system (e.g., the exchange system 165 of FIG. 1). As shown in FIG. 8, the process 800 starts with a processor of the digest system (e.g., the processor 103 of FIG. 1) receiving 802 a medical data query. The medical data query may include demographic data identifying the patient and a category of medical data. The processor parses the medical data query to extract the patient identification data and the medical data category.

Continuing with the process 800, the processor interoperates with the exchange system to determine 804 whether the patient identified by the demographic data is new to the digest system. For example, the processor can generate and transmit a patient identification query to the exchange system, which may be operating in ad-hoc and/or publication/subscription mode. The exchange system can search a data structure storing demographic data of previously analyzed patients for a record storing a copy of the demographic data. Where the exchange system finds such a record, the exchange system determines 804 that the patient is not new. Where the exchange system does not find such a record, the exchange system determines 804 that the patient is new. Where the exchange system determines 804 that the patient is not new, the exchange system proceeds to operation 824. Where the exchange system determines 804 that the patient is new, the exchange system proceeds to operation 806.

Continuing with the process 800, the exchange system creates 806 a patient reference code to uniquely identify the patient. For instance, in one example, the exchange system compresses and encrypts demographic data of the patient to generate 806 the patient reference code. Sequentially or concurrently, the exchange system retrieves 808 a medical record of the patient based on the demographic data. For instance, in one example, the exchange system interoperates with a repository (e.g., the medical data repository 105 of FIG. 1) to retrieve the medical record. In response to receiving the medical record from the repository, the exchange system transmits the medical record (e.g., the patient medical record 192 of FIG. 1) to the processor of the digest system.

Continuing with the process 800, the processor organizes 810 the medical record (e.g., converts the medical record into an indexed record). In one implementation, the processor identifies a tag associated with each medical data item in the medical record and creates entries within an indexed record for each item under its associated tag. The processor stores 812 (in memory) the organized record in association with the patient reference code.

Continuing with the process 800, the processor generates 814 a medical record digest. For instance, in one implementation, the processor identifies tags from an indexed medical record that are associated with the category of medical data specified in the query received in operation 802 and includes entries from the identified tags in the medical record digest. In an implementation, the indexed medical record may be an updated record as described below with regard to the stage 828.

Continuing with the process 800, the processor returns 816 the medical record digest to the sender of the medical data query. For example, in one implementation, the processor controls a network interface to transmit a copy of the medical record digest (which may include the patient reference code) to a device (e.g., the user interface device 106 of FIG. 1) associated with a care provider (e.g., the care provider 112 of FIG. 1).

Continuing with the process 800, the processor receives 818 a new medical data query. The new query may include the patient reference code and an updated medical condition of the patient. The processor parses the new query to extract the patient reference code and the new medical condition information.

Continuing with the process 800, the processor generates 820 a new medical record digest based on the new patient medical condition information. For instance, in one example, the processor identifies one or more tags of an indexed medical record associated with the patient medical condition and generates a new medical record digest that includes one or more entries from the one or more tags.

Continuing with the process 800, the processor returns 822 the new medical record digest to the sender of the medical data query. For example, in one implementation, the processor controls a network interface to transmit a copy of the new medical record digest (which may include the patient reference code) to a device (e.g., the user interface device 106 of FIG. 1) associated with a care provider (e.g., the care provider 112 of FIG. 1). After the processor returns 822 the new medical record digest, the process 800 ends.

Returning to the operation 824, the exchange system returns patient identification data (including a patient reference code and confidence score) to the processor of the digest system, and the processor retrieves 824 a previously processed (e.g., previously organized and stored) record associated with the patient and proceeds to the operation 814. Optionally, in some examples, the processor may proceed to retrieve interim billing data 826 by, for example, interoperating with a medical billing system (e.g., the medical billing system 425 of FIG. 3A) directly or indirectly via the exchange system. In these examples, the processor may also update 828 the medical record associated with the patient based on the interim billing data before proceeding to the operation 814.

Figure 9:
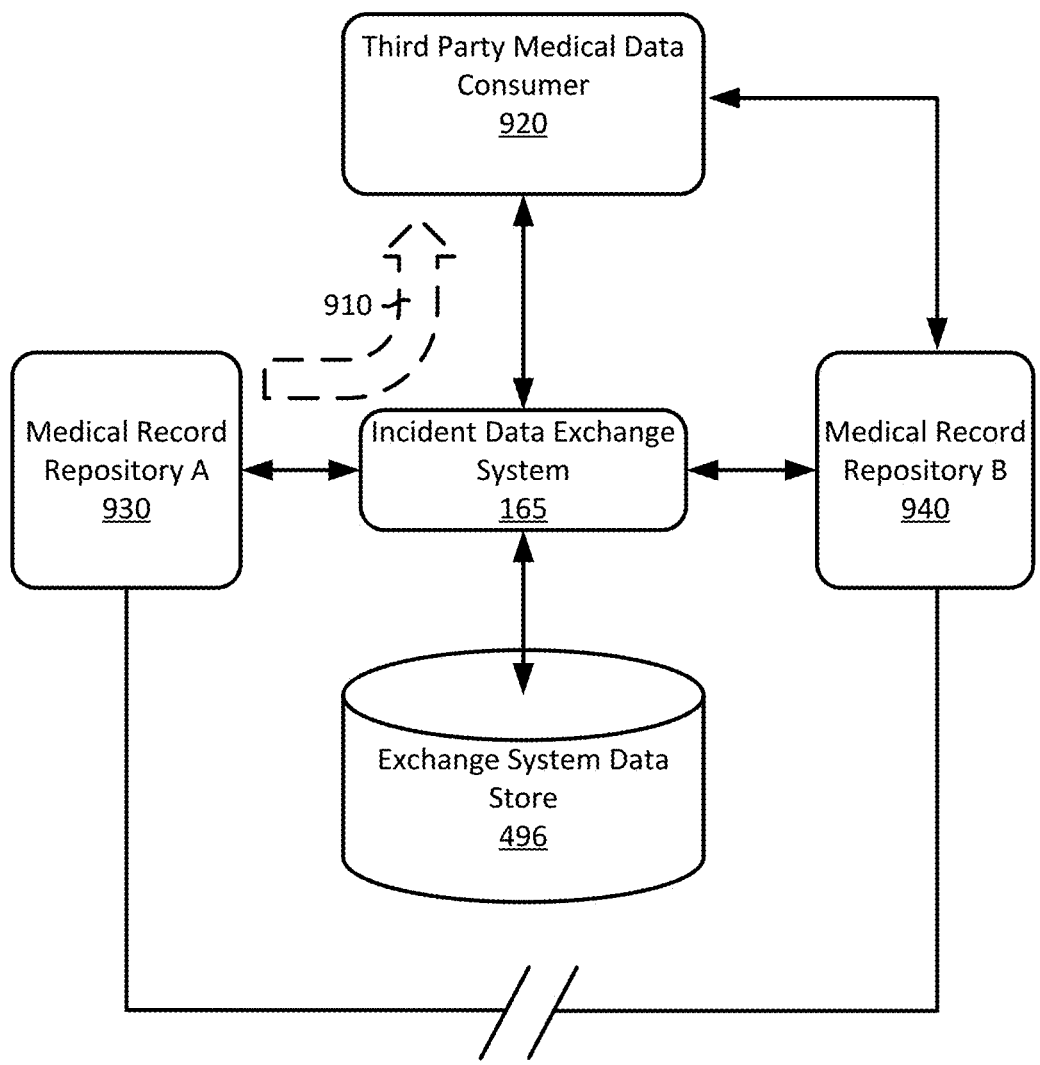
FIG. 9 is a context diagram including an incident data exchange system interoperating with multiple medical records repositories as a hub in accordance with at least one example disclosed herein.

FIG. 9 illustrates an example in which the incident data exchange system 165 advantageously provides a data repository hub between disparate medical data repositories. Medical record repository A 930 and medical record repository B 940 may not interoperate with one another. For example, these two repositories may be owned by competing hospitals or hospital systems or these two repositories may be associated with different geographic regions (e.g., the repositories may be associated with different municipalities, counties, states, etc.). Additionally or alternatively, the repositories may not interoperate because they may store medical data and/or communicate data according to different patient identification standards, and/or different messaging standards (e.g., a hospital information system may use a different messaging standard than an electronic medical record or a lab information system). Like the medical records repository 105, the repositories 930 and 940 may be for example, a HIE, a hospital records database, a health system database, a pharmacy system database, a business-to-business entity, or a combination thereof. The incident data exchange system 165 and data store 496 may interoperate with both repository A and repository B. As such, the incident data exchange system 165 is able to translate between the various patient identification standards and/or messaging standards of the disparate repositories. In an example scenario, a third party medical data consumer 920 may interoperate with the incident data exchange system 165 and with the medical record repository B 940 but may not interoperate with the medical record repository A. For example, the data consumer 920 may include a physician's office, a clinic, a hospital or hospital system, an urgent care center, an EMS agency, a pharmacy or pharmacy system, a prescription medical device supplier, a medical billing service, and/or another entity that utilizes, receives and/or generates patient medical data. However, it may be advantageous for the data consumer 920 to access medical records from the repository A 930. Due to the interoperability of the incident data exchange system 165 with both of the repositories 930 and 940, the data consumer 920 may receive medical records via the incident data exchange system 165 (e.g., as indicated by the arrow 910). For example, a patient may reside and receive regular care from a physician in Florida associated with repository A 930. The same patient may be a victim of a traffic accident during travel to Georgia. The EMS agency and hospital treating this patient in Georgia may interoperate with the repository B 940. Thus, these entities would not have direct access to the repository A 930. However, the medical history records from repository A 930 may enable more efficient and efficacious care of the victim, perhaps to a life-saving degree. Advantageously, the EMS agency and hospital may subscribe to or otherwise retain access to the incident data exchange system 165 which accesses both repositories A and B. As a hub between the repositories, the incident data exchange system 165 may provide the medical record information from repository A 930 to the medical data consumer 920.

Figure 10A:
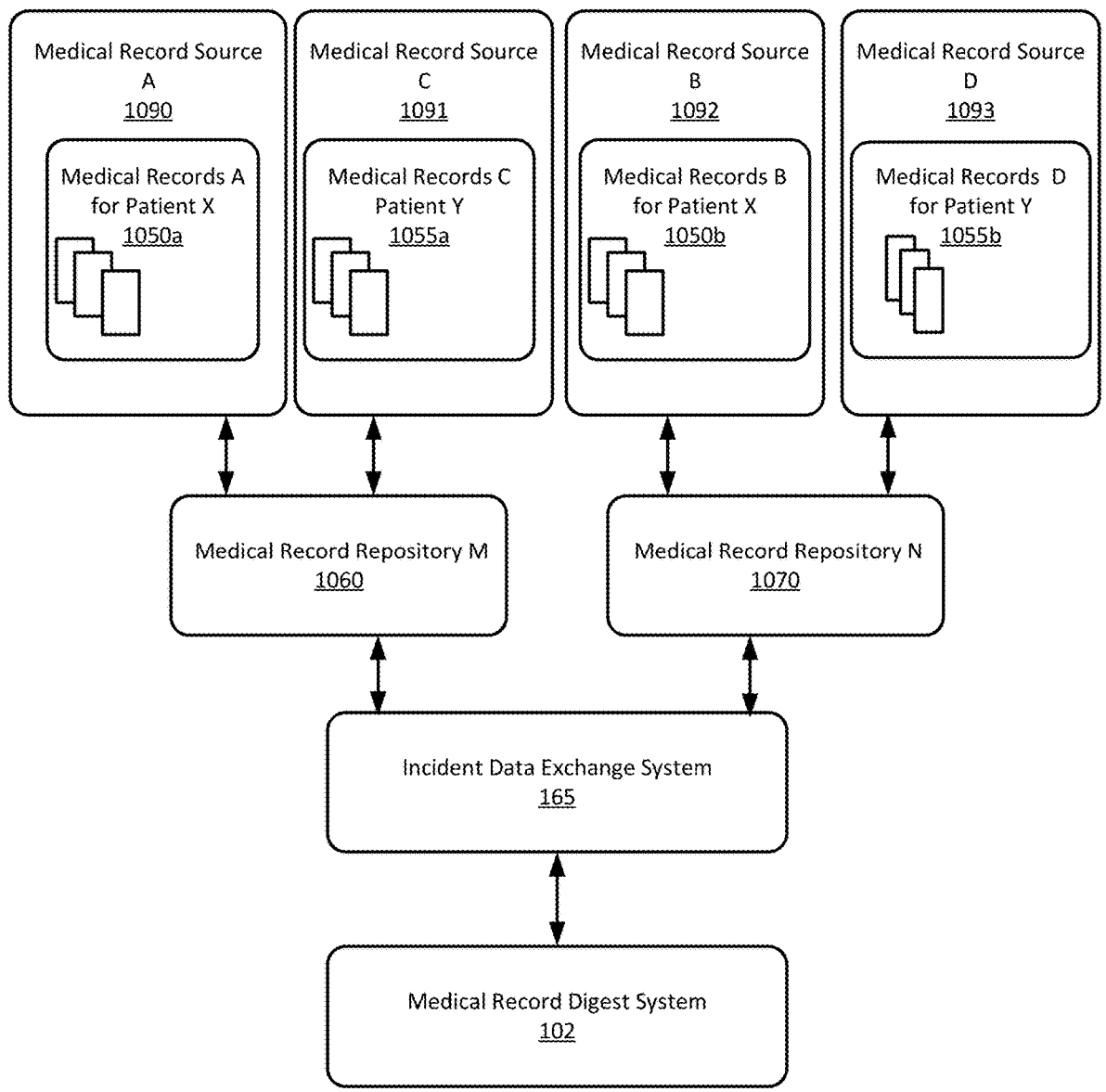
FIGS. 10A and 10B show a system and process for digest generation and update in accordance with at least one example disclosed herein.
Figure 10B:
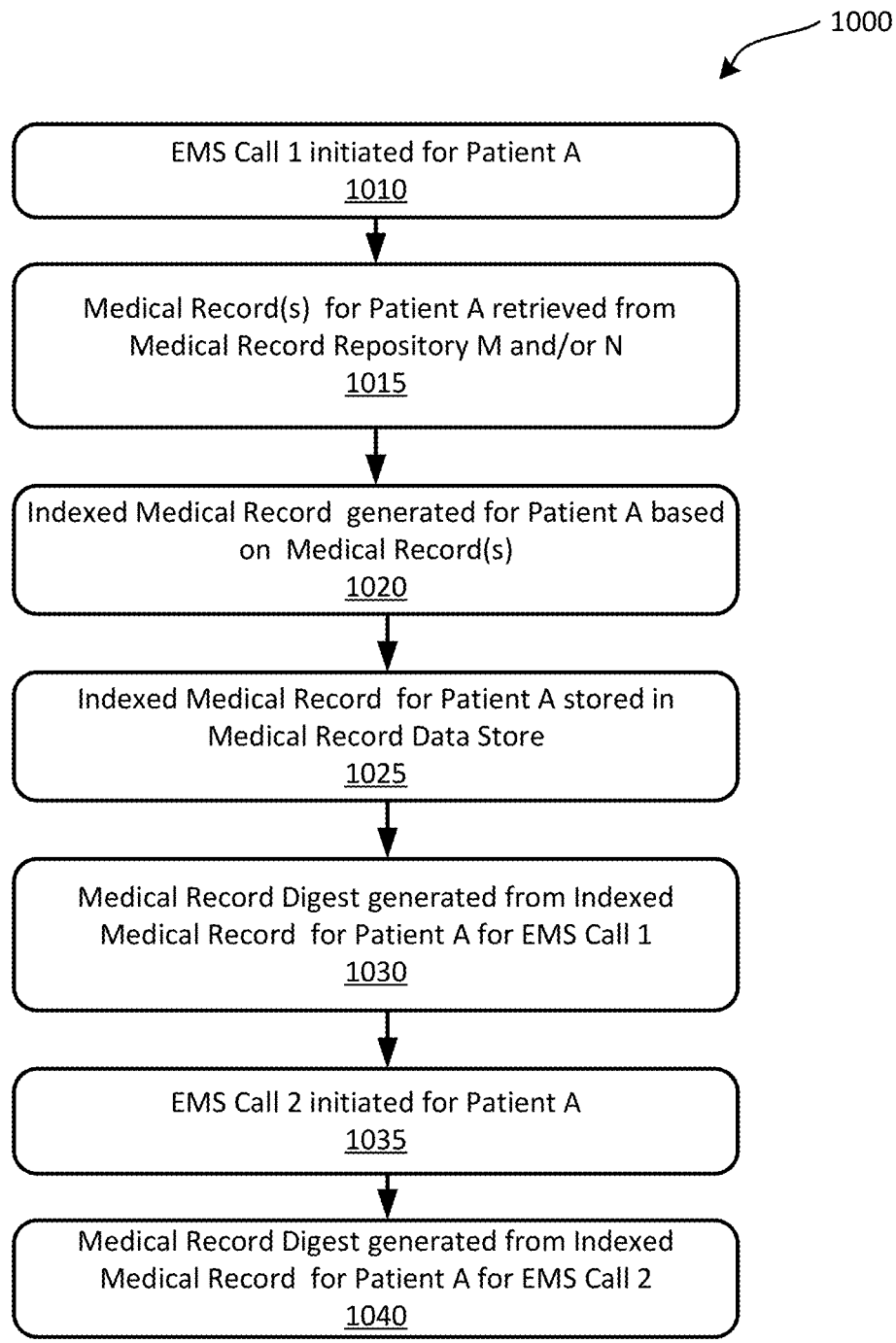

FIGS. 10A and 10B illustrate an exemplary implementation of a digest generation and update system and process that some implementations of a digest system (e.g., the digest system 102 of FIG. 1) and an exchange system (e.g., the exchange system 165 of FIG. 1) are configured to execute. As shown in FIG. 10A, the exchange system may be configured to interoperate with a medical record repository M 1060 and a medical record repository N 1070. The repository M 1060 interoperates with medical record sources A 1090 and C 1091 and the repository N 1070 interoperates with medical record sources B 1092 and D 1093. Like the medical records repository 105, the repositories 1060 and 1070 may be for example, a HIE, a hospital records database, a health system database, a pharmacy system database, a business-to-business entity, or a combination thereof. Like the source(s) 198, the medical record source(s) 1090, 1091, 1092, and 1093 may be one or more of a physician's office, a clinic, a hospital or hospital system, an urgent care center, an EMS agency, a pharmacy or pharmacy system, a prescription medical device supplier, a medical billing service, and/or another entity that utilizes, receives and/or generates patient medical data and may be data consumers as discussed in FIG. 9. In some examples, the record sources A and B have no overlapping members, respectively, with record sources C and D. However, sources A and B have overlapping members (e.g., patient X) and sources C and D have overlapping members (e.g., patient Y). The repository 1060 stores medical records 1050*a* generated for patient X and medical records 1055*a* generated for patient Y. The repository 1070 stores medical records 1050*b* generated for patient X and medical records 1055*b* generated for patient Y.

As shown in FIG. 10B, the process 1000 starts with the exchange system receiving a call record (e.g., as described above with regard to FIG. 1) indicating that an EMS call for Patient A has been initiated 1010. For example, a CAD system (e.g., the CAD system 130 of FIG. 1) may receive input from an EMS agency (e.g., the EMS agency 412 of FIG. 3B) specifying fields of the call record. The CAD system may transmit the call record to the exchange system.

Continuing with the process 1000, the exchange system interoperates with the repository 1060 and/or the repository 1070 to retrieve 1015 one or more medical records for the patient A. For example, the exchange system may generate and transmit a query to one or both of the repositories 1060 and 1070 and receive responses with the one or more medical records for the patient A. Upon receiving the responses, the exchange system may process the responses and transmit the medical records specified therein to the digest system.

Continuing with the process 1000, the digest system indexes 1020 the one or more medical records for the patient A to generate an indexed medical record for the patient A. For example, the digest system can identify data items within the one or more medical records and store each data item as an entry under an associated tag within the indexed medical record. The digest system stores 1025 the indexed medical record in an indexed record data store (e.g., the data store 420 of FIG. 3B).

Continuing with the process 1000, the digest system generates 1030, from the indexed medical record, a medical digest record for patient A that includes patient medical information relevant to the patient A's condition as reported in the call record received in operation 1010. The digest system may also transmit the medical digest record to EMS personnel working the call.

Continuing with the process 1000, the exchange system receives another call record indicating that an EMS call for Patient A has been initiated 1035. For example, the CAD system may receive input from an EMS agency specifying fields of the call record. The CAD system may transmit the call record to the exchange system. In response to receiving the call record, the exchange system bypasses any interoperations with the repositories 1060 and 1070 that would otherwise occur because a current medical record already exists for Patient A. As such, the exchange system simply transmits an incident record based on the call record to the digest system, and the digest system generates another medical record digest for Patient A that is relevant to the condition of Patient A as recorded in the call and incident records. The digest system may also transmit the medical digest record to EMS personnel working the call. Upon completion of the operation 1040, the process 1000 ends.

The preceding disclosure describes several features that may be implemented with one or more computing devices. For example, any of the user interface device 106, the CAD system 130, the digest system 102, the exchange system 165, and the repository 105 of FIG. 1 may be implemented using one or more computing devices as described further below with reference to FIG. 11. In addition, the medical billing system 425, the navigation system 428, the demographic verifier 499, and the patient charting system 429 of FIG. 3A may be implemented using one or more computing devices. Moreover, the CAD server 430, the navigation server 428, the digest server 418, the charting server 422, the incident data exchange server 497, the case data store 424, the medical billing server 467, the data stores 420 and 496, the navigation device 436, and the user interface device 434 may be implemented using one or more computing devices. An example of such a computing device includes a laptop computer, a mobile device (e.g., a computer tablet, smartphone, or wearable device such as a headset, glasses, or watch), a server in the data center, and the like.

Figure 11:
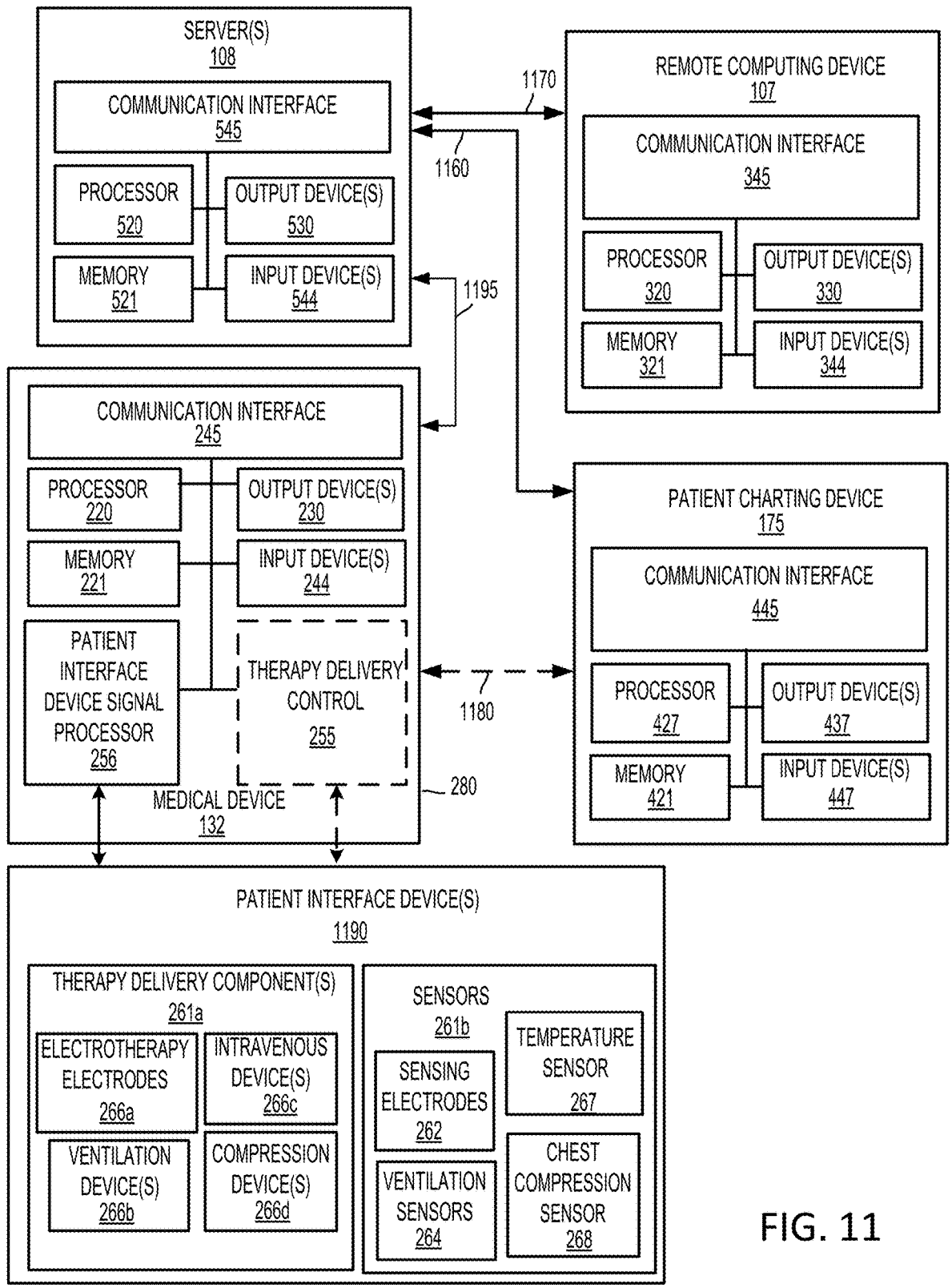
FIG. 11 is a schematic block diagram of examples of computing and medical device components with which at least one example disclosed herein may be implemented.

Referring to FIG. 11, a block diagram of examples of computing and medical device components are shown schematically.

The medical device 132 can include a processor 220, a memory 221, one or more output devices 230, one or more user input devices 244, and a communications interface 245. The communications interface 245 can include any of a variety of transmitters and/or receivers. For instance, in some examples, the communications interface 245 includes one or more of an NFC tag, an RFID tag, a barcode, and a QR code.

In various implementations, the medical devices 132 can include a defibrillator, patient monitor, defibrillator/monitor, an automated compression device, a therapeutic cooling device, an extracorporeal membrane oxygenation (ECMO) device, a ventilation device, combinations thereof, or another type of medical device configured to couple to one or more therapy delivery components to provide therapy to the patient. In an implementation, the medical devices 132 can include an integrated therapy delivery/monitoring device within a single housing 280. The single housing 280 can surround, at least in part, a patient interface device signal processor 256 and/or a therapy delivery control 255.

The patient interface devices 1190 can include one or more therapy delivery component(s) 261*a* and/or one or more sensor device(s) 261*b*. The medical device 132 can be configured to couple to the one or more therapy delivery component(s) 261*a*. In combination, the medical device 132 and the one or more therapy delivery components can provide therapeutic treatment to a patient (e.g., the patient 114 of FIG. 1). In an implementation, the medical device 132 can include or incorporate the therapy delivery component(s) 261*a*. The therapy delivery component(s) 261*a* are configured to deliver therapy to the patient and can be configured to couple to the patient. For example, the therapy delivery component(s) 261*a* can include one or more of electrotherapy electrodes including defibrillation electrodes and/or pacing electrodes, chest compression devices (e.g., one or more belts or a piston), ventilation devices (e.g., a mask and/or tubes), drug delivery devices, etc. The medical device 132 can include the one or more therapy delivery component(s) 261*a* and/or can be configured to couple to the one or more therapy delivery component(s) 261*a* in order to provide medical therapy to the patient. The therapy delivery component(s) 261*a* can be configured to couple to the patient. For example, a care provider (e.g., the care provider 112) may attach the electrodes to the patient, and the medical device 132 (e.g., a defibrillator or defibrillator/patient monitor) may provide electrotherapy to the patient via the defibrillation electrodes. These examples are not limiting of the disclosure as other types of medical devices, therapy delivery components, sensors, and therapy are within the scope of the disclosure.

The medical devices 132 can include, for example, a therapeutic medical device capable of delivering a medical therapy. For example, the medical therapy can be electrical therapy (e.g. defibrillation, cardiac pacing, synchronized cardioversion, diaphragmatic or phrenic nerve stimulation) and the medical devices 132 can include a defibrillator, a defibrillator/monitor and/or another medical device configured to provide electrotherapy. As another example, the medical therapy can be chest compression therapy for treatment of cardiac arrest and the medical device 132 can be a mechanical chest compression device such as a belt-based chest compression device or a piston-based chest compression device. As other examples, the medical therapy can be ventilation therapy, therapeutic cooling or other temperature management, invasive hemodynamic support therapy (e.g. Extracorporeal Membrane Oxygenation (ECMO)), etc. and the medical device 132 can be a device configured to provide a respective therapy. In an implementation, the medical device 132 can be a combination of one or more of these examples. The therapeutic medical device can include patient monitoring capabilities via one or more sensors. These types of medical therapy and devices are examples only and not limiting of the disclosure.

The medical devices 132 can include, incorporate, and/or be configured to couple to the one or more sensor(s) 261*b* which can be configured to couple to the patient. The sensor(s) 261*b* are configured to provide signals indicative of sensor data to the medical device 132. The sensor(s) 261*b* can be configured to couple to the patient. For example, the sensor(s) 261*b* can include cardiac sensing electrodes, a chest compression sensor, and/or ventilation sensors. The one or more sensors 261*b* can generate signals indicative of physiological parameters of the patient. For example, the physiological parameters can include one or more of at least one vital sign, an ECG, blood pressure, heart rate, pulse oxygen level, respiration rate, heart sounds, lung sounds, respiration sounds, tidal CO2, saturation of muscle oxygen (SMO2), arterial oxygen saturation (SpO2), cerebral blood flow, electroencephalogram (EEG) signals, brain oxygen level, tissue pH, tissue fluid levels, physical parameters as determined via ultrasound images, parameters determined via near-infrared reflectance spectroscopy, pneumography, and/or cardiography, etc. Additionally or alternatively, the one or more sensors 261*b* can generate signals indicative of chest compression parameters, ventilation parameters, drug delivery parameters, fluid delivery parameters, etc.

In addition to delivering therapy to the patient, the therapy delivery component(s) 261*a* can include, be coupled to, and/or function as sensors and provide signals indicative of sensor data (e.g., second sensor data) to the medical device 132. For example, the defibrillation electrodes can be configured as cardiac sensing electrodes as well as electrotherapy delivery devices and can provide signals indicative of transthoracic impedance, electrocardiogram (ECG), heart rate and/or other physiological parameters. As another example, a therapeutic cooling device can be an intravenous cooling device. Such a cooling device can include an intravenous (IV) device as a therapy delivery component configured to deliver cooling therapy and sense the patient's temperature. For example, the IV device can be a catheter that includes saline balloons configured to adjust the patient's temperature via circulation of temperature controlled saline solution. In addition, the catheter can include a temperature probe configured to sense the patient's temperature. As a further example, an IV device can provide therapy via drug delivery and/or fluid management. The IV device can also monitor and/or enable monitoring of a patient via blood sampling and/or venous pressure monitoring (e.g., central venous pressure (CVP) monitoring).

The medical devices 132 can be configured to receive the sensor signals (e.g., from the therapy delivery component(s) 261*a* and/or the sensor(s) 261*b*) and to process the sensor signals to determine and collect the patient data. The patient data can include patient data which can characterize a status and/or condition of the patient (e.g., physiological data such as ECG, heart rate, respiration rate, temperature, pulse oximetry, non-invasive hemoglobin parameters, capnography, oxygen saturation (SpO2), end tidal carbon dioxide (EtCO2), invasive blood pressure (IBP), non-invasive blood pressures (NIBP), tissue pH, tissue oxygenation, Near Infrared Spectroscopy (NIRS) measurements, etc.). Additionally or alternatively, the patient data can characterize the delivery of therapy (e.g., chest compression data such as compression depth, compression rate, etc.) and/or the patient data can characterize a status and/or condition of the medical equipment used to treat the patient (e.g., device data such as shock time, shock duration, attachment of electrodes, power-on, etc.).

In some examples, the components of 220, 221, 230, 244, 245, and 255 of the medical device 132 are communicatively coupled (directly and/or indirectly) to each other for bi-directional communication.

Although shown as separate entities in FIG. 11, the one or more of the components of the medical device 132 can be combined into one or more discrete components and/or can be part of the processor 220. The processor 220 and the memory 221 can include and/or be coupled to associated circuitry to perform the functions described herein.

In an implementation, the medical devices 132 can include a therapeutic medical device configured to deliver medical therapy to the patient. Thus, the medical devices 132 can optionally include the therapy delivery control module 255. For example, the therapy delivery control module 255 can be an electrotherapy delivery circuit that includes one or more capacitors configured to store electrical energy for a pacing pulse or a defibrillating pulse. The electrotherapy delivery circuit can further include resistors, additional capacitors, relays and/or switches, electrical bridges such as an H-bridge (e.g., including a plurality of insulated gate bipolar transistors or IGBTs), voltage measuring components, and/or current measuring components. As another example, the therapy delivery control module 255 can be a compression device such as an electro-mechanical controller configured to control a mechanical compression device. As a further example, the therapy delivery control module 255 can be an electro-mechanical controller configured to control drug delivery, temperature management, ventilation, and/or other type of therapy delivery. Alternatively, some examples of the medical devices 132 may not be configured to deliver medical therapy to the patient 114 but can be configured to provide patient monitoring and/or diagnostic care. As shown in FIG. 11, in some examples, the therapy delivery control 255 exchanges messages 1180 with the charting device 175 (e.g., the patient charting device). These messages can include patient data descriptive of therapy provided to the patient or other patient data stored on the medical devices 132. This patient data can be used by an ePCR application in generating an ePCR documenting a dispatched EMS event.

The medical devices 132 can incorporate and/or be configured to couple to one or more patient interface devices 1190. The patient interface devices 1190 can include one or more therapy delivery component(s) 261*a* and one or more sensor(s) 261*b*. The one or more therapy delivery component(s) 261*a* and the one or more sensor(s) 261*b* sensor can provide one or more signals to the medical devices 132 via wired and/or wireless connection(s).

The one or more therapy delivery component(s) 261*a* can include electrotherapy electrodes (e.g., the electrotherapy electrodes 266*a*), ventilation device(s) (e.g., the ventilation devices 266*b*), intravenous device(s) (e.g., the intravenous devices 266c), compression device(s) (e.g., the compression devices 266d), etc. For example, the electrotherapy electrodes can include defibrillation electrodes, pacing electrodes, and/or combinations thereof. The ventilation devices can include a tube, a mask, an abdominal and/or chest compressor (e.g., a belt, a cuirass, etc.), etc. and combinations thereof. The intravenous devices can include drug delivery devices, fluid delivery devices, and combinations thereof. The compression devices can include mechanical compression devices such as abdominal compressors, chest compressors, belts, pistons, and combinations thereof. In various implementation, the therapy delivery component(s) 261a can be configured to provide sensor data and/or be coupled to and/or incorporate sensors. For example, the electrotherapy electrodes can provide sensor data such as transthoracic impedance, ECG, heart rate, etc. Further the electrotherapy electrodes can include and or be coupled to a chest compression sensor. As another example, the ventilation devices can be coupled to and/or incorporate flow sensors, gas species sensors (e.g., oxygen sensor, carbon dioxide sensor, etc.), etc. As a further example, the intravenous devices can be coupled to and/or incorporate temperature sensors, flow sensors, blood pressure sensors, etc. As yet another example, the compression devices can be coupled to and/or incorporate chest compression sensors, patient position sensors, etc. The therapy delivery control module 255 can be configured to couple to and control the therapy delivery component(s) 261a.

In various implementations, the sensor(s) 261b can include one or more sensor devices configured to provide sensor data that includes, for example, but not limited to electrocardiogram (ECG), blood pressure, heart rate, pulse oxygen level, respiration rate, heart sounds, lung sounds, respiration sounds, tidal CO2, saturation of muscle oxygen (SMO2), arterial oxygen saturation (SpO2), cerebral blood flow, electroencephalogram (EEG) signals, brain oxygen level, tissue pH, tissue fluid levels, images and/or videos via ultrasound, laryngoscopy, and/or other medical imaging techniques, near-infrared reflectance spectroscopy, pneumography, cardiography, and/or patient movement. Images and/or videos can be two-dimensional or three-dimensional.

The sensor(s) 261b can include sensing electrodes (e.g., the sensing electrodes 262), ventilation sensors (e.g., the ventilation sensors 264), temperature sensors (e.g., the temperature sensor 267), chest compression sensors (e.g., the chest compression sensor 268), etc. For example, the sensing electrodes can include cardiac sensing electrodes. The cardiac sensing electrodes can be conductive and/or capacitive electrodes configured to measure changes in a patient's electrophysiology, for example to measure the patient's ECG information. In an implementation, the sensing electrodes can be configured to measure the transthoracic impedance and/or a heart rate of the patient. The ventilation sensors can include spirometry sensors, flow sensors, pressure sensors, oxygen and/or carbon dioxide sensors such as, for example, one or more of pulse oximetry sensors, oxygenation sensors (e.g., muscle oxygenation/pH), O2 gas sensors and capnography sensors, and combinations thereof. The temperature sensors can include an infrared thermometer, a contact thermometer, a remote thermometer, a liquid crystal thermometer, a thermocouple, a thermistor, etc. and can measure patient temperature internally and/or externally. The chest compression sensor can include one or more motion sensors including, for example, one or more accelerometers, one or more force sensors, one or more magnetic sensors, one or more velocity sensors, one or more displacement sensors, etc. The chest compression sensor can be, for example, but not limited to, a compression puck, a smart phone, a hand-held device, a wearable device, etc. The chest compression sensor can be configured to detect chest motion imparted by a rescuer and/or an automated chest compression device (e.g., a belt system, a piston system, etc.). The chest compression sensor can provide signals indicative of chest compression data including displacement data, velocity data, release velocity data, acceleration data, compression rate data, dwell time data, hold time data, blood flow data, blood pressure data, etc. In an implementation, the sensing electrodes and/or the electrotherapy electrodes can include or be configured to couple to the chest compression sensor.

Continuing with FIG. 11, examples of components of the charting device 175 are shown schematically. In an implementation, the charting device 175 can be configured as a charting device. The charting device 175 can include a processor 427, a memory 421, one or more output devices 437, one or more user input devices 447, and a communications interface 445. FIG. 11 also illustrates schematically examples of components of the computing device 107. As shown in FIG. 11, the computing device 107 can include a processor 320, a memory 321, one or more output devices 330, one or more user input devices 344, and a communications interface 345. FIG. 11 further illustrates schematically examples of components of the server(s) 108. As shown in FIG. 11, the server(s) 108 can include a processor 520, a memory 521, one or more output devices 530, one or more user input devices 544, and a communications interface 545.

Each of the charting device 175 (e.g., the charting device) and the computing device 107 can be a computer system, such as a desktop, notebook, mobile, portable, or other type of computing system. Each of these devices 175 and 107 can include server(s) and/or access server(s) via a monitor and/or other connected user interface device. Although described as server(s), the server(s) 108 can be another type of computing system including for example a desktop, notebook, mobile, portable, or other type of computing system.

As shown in FIG. 11, each of the devices 175 and 107, along with the server(s) 108 and the medical devices 132, includes a bus or other interconnection mechanism that communicably couples the processor, memory, output devices, input devices, and communication interface included therein. The bus can include a PCI/PCI-X or SCSI based system bus depending on the storage devices used, for example.

The processors 220, 320, 427, and 520 can each include a processor, such as, but not limited to, an Intel® Itanium® or Itanium 2® processor(s), or AMD® Opteron® or Athlon MP® processor(s), or Motorola® lines of processors. The communication interfaces 245, 345, 445, and 545 can each be any of an RS-232 port for use with a modem-based dialup connection, a 10/100 Ethernet port, or a Gigabit port using copper or fiber, for example. The communication interfaces 245, 345, 445, and 545 may be chosen depending on a network(s) such a Local Area Network (LAN), Wide Area Network (WAN), or any network to which the medical devices 132, the charting device 175, the computing device 107, and/or the server(s) 108 may connect. The memories 221, 321, 421, and 521 can be Random Access Memory (RAM), Read Only Memory (ROM), Flash memory, and/or another dynamic volatile and/or non-volatile storage device(s). The memories 221, 321, 421, and 521 can be used to store information and instructions. For example, hard disks such as the Adaptec® family of SCSI drives, an optical disc, an array of disks such as RAID (e.g. the Adaptec family of RAID drives), or any other mass storage devices may be used. The components described above are meant to exemplify some types of possibilities. In no way should the aforementioned examples limit the scope of the disclosure. The memories 221, 321, 421, and 521 can further include removable storage media such as external hard-drives, floppy drives, flash drives, IOMEGA® Zip Drives, Compact Disc-Read Only Memory (CD-ROM), Compact Disc-Re-Writable (CD-RW), or Digital Video Disk-Read Only Memory (DVD-ROM), for example.

Continuing with FIG. 11, the server(s) 108 can include, for example, the one or more storage server(s) and one or more application server(s). In some examples, the server(s) 108 are configured to exchange messages 1170 with the computing device 107. These messages can include charting and/or case data as described above. In some examples, the server(s) 108 are configured to exchange messages 1160 with the charting device 175 via an ePCR API. These messages can include data descriptive of ePCRs generated by the charting device 175. In some examples, the server(s) 108 are configured to exchange messages 1195 with the medical devices 132. These messages can include data descriptive of a patient (e.g., the patient 114 of FIG. 1) being treated via by the medical device and/or treatment being delivered by the medical devices 132.

Some examples of the present disclosure include various steps, some of which can be performed by hardware components or can be embodied in machine-executable instructions. These machine-executable instructions can be stored on a non-transitory data storage medium and can be used to cause a general-purpose or a special-purpose processor programmed with the instructions to perform the steps. The non-transitory data storage medium can further store an operating system and the machine-executable instructions can be included within one or more software applications or programs, such as the ePCR application. These programs can implement the features disclosed herein and the methods that they execute. Alternatively, the steps can be performed by a combination of hardware, software, and/or firmware, on one device and/or distributed across multiple devices and/or processors. In addition, some examples of the present disclosure can be performed or implemented, at least in part (e.g., one or more modules), on one or more computer systems, mainframes (e.g., IBM mainframes such as the IBM zSeries, Unisys ClearPath Mainframes, HP Integrity NonStop server(s), NEC Express series, and others), or client-server type systems. In addition, specific hardware aspects of examples of the present disclosure can incorporate one or more of these systems, or portions thereof.

Having thus described several aspects of at least one example, it is to be appreciated that various alterations, modifications, and improvements will readily occur to those skilled in the art. For instance, examples disclosed herein can also be used in other contexts. Such alterations, modifications, and improvements are intended to be part of this disclosure and are intended to be within the scope of the examples discussed herein. Accordingly, the foregoing description and drawings are by way of example only.

The invention claimed is:

1. An emergency medical services (EMS) medical record acquisition system for providing medical record information to an EMS rescuer for an encounter with a patient in a mobile EMS environment, the system comprising:

a user interface device comprising:
at least one user interface device processor; and
a non-transitory user interface device memory having stored therein instructions, that when executed by the at least one user interface device processor, cause the at least one user interface device processor to:
provide a user interface,
prompt, via the user interface, the EMS rescuer to request a medical record digest,
receive the medical record digest from a medical record digest system, and
present, via the user interface, the received medical record digest;
the medical record digest system, wherein the medical record digest system is in a cloud environment and is configured to communicatively couple to an incident data exchange system and the user interface device, the medical record digest system comprising:
at least one medical record digest system processor; and
a non-transitory medical record digest system memory having stored therein instructions, that when executed by the at least one medical record digest system processor, cause the at least one medical record digest system processor to:
generate, by a query service, a first medical record query for a medical record for the patient, and
transmit, by the query service, the generated first medical record query to the incident data exchange system;
one or more patient identification data sources; and
the incident data exchange system, wherein the incident data exchange system is in the cloud environment and is configured to communicatively couple to (a) the medical record digest system and to at least one medical record repository as an intermediary between the medical record digest system and the at least one medical record repository and (b) the one or more patient identification data sources, the incident data exchange system comprising:
one or more exchange system processors; and
a non-transitory incident data exchange system memory having stored therein instructions, that when executed by the one or more exchange system processors, cause the one or more exchange system processors to:
receive patient identification data from the one or more patient identification data sources for an EMS call for the patient,
generate a second medical record query for the medical record for the patient, wherein the second medical record query includes at least a first portion of the patient identification data,
send the second medical record query to the at least one medical record repository,
receive the medical record for the patient from the at least one medical record repository,
generate a patient reference code based on at least a second portion of the patient identification data,
store the medical record with the patient reference code in the incident data exchange system memory, and
transmit the medical record and the patient reference code to the medical record digest system,
wherein the instructions stored in the medical record digest system memory, when executed by the at least one medical record digest system processor, cause the at least one medical record digest system processor to;

receive the medical record and the patient reference code from the incident data exchange system, store the medical record with the patient reference code in the medical record digest system memory, select a portion of the medical record based on clinical relevance to the encounter with the patient, generate the medical record digest that comprises the selected portion of the medical record, and transmit the medical record digest with the patient reference code to the user interface device in the mobile EMS environment.

2. The EMS medical record acquisition system of claim 1, wherein the one or more patient identification data sources comprise one or more of a computer-aided dispatch system or a patient charting system.

3. The EMS medical record acquisition system of claim 1, wherein:

the incident data exchange system memory comprises a predetermined patient identification criterion; and the instructions stored in the incident data exchange system memory, when executed by the one or more exchange system processors, cause the one or more exchange system processors to determine whether the patient identification data from the one or more patient identification data sources satisfies the predetermined patient identification criterion.

4. The EMS medical record acquisition system of claim 3, wherein the predetermined patient identification criterion comprises a list of identification data items necessary to include in the second medical record query to distinguish between multiple patients represented in the at least one medical record repository.

5. The EMS medical record acquisition system of claim 4, wherein the list of identification data items comprises patient demographic data comprising one or more of a first name of the patient, a last name of the patient, a date of birth of the patient, a government issued identifier of the patient, a telephone number of the patient, or a gender of the patient.

6. The EMS medical record acquisition system of claim 3, wherein the instructions stored in the incident data exchange system memory, when executed by the one or more exchange system processors, cause the one or more exchange system processors to:

request supplemental patient identification data from one or more supplemental patient identification data sources in response to a determination that the predetermined patient identification criterion is unsatisfied by the patient identification data from the one or more patient identification data sources; and generate combined patient identification data comprising the supplemental patient identification data from the one or more supplemental patient identification data sources and the patient identification data from the one or more patient identification data sources, wherein the predetermined patient identification criterion is satisfied by the combined patient identification data.

7. The EMS medical record acquisition system of claim 6, wherein:

the one or more patient identification data sources comprise a computer-aided dispatch (CAD) system;

the one or more supplemental patient identification data sources comprise an EMS patient charting system;

the patient identification data comprises one or more of patient medical data or patient demographic data from the CAD system; and the supplemental patient identification data comprises one or more of patient medical data or patient demographic data from the EMS patient charting system.

8. The EMS medical record acquisition system of claim 6, wherein the one or more patient identification data sources, the one or more supplemental patient identification data sources, the incident data exchange system, and the medical record digest system form a cloud-based platform.

9. The EMS medical record acquisition system of claim 6, wherein the one or more supplemental patient identification data sources comprise the user interface device.

10. The EMS medical record acquisition system of claim 9, wherein the instructions stored in the medical record digest system memory, when executed by the at least one medical record digest system processor, cause the at least one medical record digest system processor to:

provide a prompt, via the user interface, for for a user-entered confirmation of the patient identification data;

receive the user-entered confirmation of the patient identification data; and transmit the generated first medical record query to the incident data exchange system in response to receipt of the user-entered confirmation.

11. The EMS medical record acquisition system of claim 1, wherein the instructions stored in the incident data exchange system memory, when executed by the one or more exchange system processors, cause the one or more exchange system processors to generate the patient reference code based on a hash and/or encryption of the at least the second portion of the patient identification data.

12. The EMS medical record acquisition system of claim 1, wherein the at least one medical record repository comprises one or more of a health information exchange, a hospital records database, or a health system database.

13. The EMS medical record acquisition system of claim 1, wherein the instructions stored in the medical record digest system memory, when executed by the at least one medical record digest system processor, cause the at least one medical record digest system processor to:

serve the user interface to the user interface device.

14. The EMS medical record acquisition system of claim 13, wherein the user interface is one or more of a visual user interface, an audio user interface, or an augmented reality user interface.

15. The EMS medical record acquisition system of claim 1, wherein the mobile EMS environment comprises at least one emergency medical vehicle comprising one or more of an ambulance, a fire engine, an EMS crew transport vehicle, or a helicopter.

16. The EMS medical record acquisition system of claim 1, wherein the medical record digest system memory, the user interface device, and the at least one medical record digest system processor are disposed in a mobile computing device.

17. The EMS medical record acquisition system of claim 1, wherein:

the medical record digest system memory and the at least one medical record digest system processor are disposed in a cloud server configured to communicatively couple to the user interface device; and the medical record digest system provides a medical record digest application at the user interface device.

18. The EMS medical record acquisition system of claim 1, wherein the one or more patient identification data sources comprise one or more of a hospital information system, a medical billing system, a case data store, a charting system, a computer-aided dispatch system, a navigation system, a medical device, or the medical record digest system.

19. The EMS medical record acquisition system of claim 18, wherein the instructions stored in the incident data exchange system memory, when executed by the one or more exchange system processors, cause the one or more exchange system processors to maintain, within the incident data exchange system memory, a cross-reference that relates the patient reference code with patient identifiers generated by one or more of the hospital information system, the medical billing system, the case data store, the charting system, the computer-aided dispatch system, the navigation system, the medical device, the medical record digest system, or a demographic verifier.

20. The EMS medical record acquisition system of claim 1, wherein the instructions stored in the incident data exchange system memory, when executed by the one or more exchange system processors, cause the one or more exchange system processors to identify at least one subscription to receive the medical record of the patient, the at least one subscription identifying the medical record digest system.

21. The EMS medical record acquisition system of claim 1, wherein the instructions stored in the medical record digest system memory, when executed by the at least one medical record digest system processor, cause the at least one medical record digest system processor to select the portion of the medical record based at least in part on a predetermined list of medical data specific to an EMS agency.

22. The EMS medical record acquisition system of claim 1, wherein the instructions stored in the medical record digest system memory, when executed by the at least one medical record digest system processor, cause the at least one medical record digest system processor to select the portion of the medical record based at least in part on an attribute of the mobile EMS environment.

23. The EMS medical record acquisition system of claim 1, wherein the instructions stored in the medical record digest system memory, when executed by the at least one medical record digest system processor, cause the at least one medical record digest system processor to select the portion of the medical record based at least in part on a category of medical data included in the medical record.

24. The EMS medical record acquisition system of claim 1, wherein the instructions stored in the medical record digest system memory, when executed by the at least one medical record digest system processor, cause the at least one medical record digest system processor to select the portion of the medical record based at least in part on EMS call type data.

25. The EMS medical record acquisition system of claim 24, wherein the EMS call type data includes physiological signals from the patient received from a medical device that is in the mobile EMS environment and that is coupled to the patient.

26. The EMS medical record acquisition system of claim 24, wherein the EMS call type data includes billing information for the patient.

* * * * *